(12) United States Patent
Ardito et al.

(10) Patent No.: US 10,905,441 B2
(45) Date of Patent: Feb. 2, 2021

(54) SURGICAL GUIDE FOR USE IN LIGAMENT REPAIR PROCEDURES

(71) Applicant: Medos International Sàrl, Le Locle (CH)

(72) Inventors: Lauren Ardito, Boston, MA (US); Gary Fernandes, Assonet, MA (US); Michael S. Varieur, Portsmouth, RI (US); Kevin J. Zylka, Taunton, MA (US); Scott Presbrey, Slatersville, RI (US)

(73) Assignee: MEDOS INTERNATIONAL SÀRL, Le Locle (CH)

( * ) Notice: Subject to any disclaimer, the term of this patent is extended or adjusted under 35 U.S.C. 154(b) by 148 days.

(21) Appl. No.: 16/129,138

(22) Filed: Sep. 12, 2018

(65) Prior Publication Data

US 2019/0008530 A1    Jan. 10, 2019

Related U.S. Application Data

(62) Division of application No. 14/503,178, filed on Sep. 30, 2014, now Pat. No. 10,098,646.

(51) Int. Cl.
*A61B 17/16* (2006.01)
*A61B 17/17* (2006.01)
*A61B 90/00* (2016.01)

(52) U.S. Cl.
CPC ...... *A61B 17/1675* (2013.01); *A61B 17/1714* (2013.01); *A61B 17/1764* (2013.01);
(Continued)

(58) Field of Classification Search
CPC ............ A61B 17/1714; A61B 17/1764; A61B 2090/062; A61B 5/1076; A61B 5/1075; A61B 8/0858; A61C 13/00
See application file for complete search history.

(56) References Cited

U.S. PATENT DOCUMENTS

| 750,449 A | 1/1904 | Gillard |
|---|---|---|
| 2,823,563 A | 2/1958 | Nipken |

(Continued)

FOREIGN PATENT DOCUMENTS

| CN | 103025253 A | 4/2013 |
|---|---|---|
| EP | 1 374 784 A1 | 1/2004 |

(Continued)

OTHER PUBLICATIONS

Japanese Office Action for Application No. 2015-190870, dated Jul. 1, 2019 (10 pages).

(Continued)

*Primary Examiner* — Matthew J Lawson

(57) ABSTRACT

Devices, systems, and methods are provided for ligament repair procedures, and can be used to establish a location and trajectory for forming a bone tunnel in bone. One exemplary embodiment of a surgical guide for using in a ligament repair procedure includes a guide arm and a carriage that can be selectively locked along the guide arm to define an angle of the bone tunnel. The guide arm also defines a location of a distal end of the bone tunnel. In some embodiments the carriage is configured to have a bullet side-loaded into it, and the bullet can be used to define a location of a proximal end of the bone tunnel. The present disclosure also provides for a gage that limits the distance a drill pin that drills the bone tunnel can travel. A variety of other, devices, systems, and methods are also provided.

30 Claims, 25 Drawing Sheets

(52) U.S. Cl.
CPC ... *A61B 2090/034* (2016.02); *A61B 2090/062* (2016.02); *A61B 2090/067* (2016.02)

(56) References Cited

U.S. PATENT DOCUMENTS

| | | | |
|---|---|---|---|
| 3,838,517 A | 10/1974 | Michnick | |
| 4,037,592 A | 7/1977 | Kronner | |
| 4,314,406 A | 2/1982 | Barnes | |
| 4,535,768 A | 8/1985 | Hourahane et al. | |
| 4,672,957 A | 6/1987 | Hourahane | |
| 4,708,139 A | 11/1987 | Dunbar, IV | |
| 4,722,331 A | 2/1988 | Fox | |
| 4,781,182 A | 11/1988 | Purnell et al. | |
| 4,883,048 A | 11/1989 | Purnell et al. | |
| 4,901,711 A | 2/1990 | Goble et al. | |
| 4,993,679 A | 2/1991 | Urai et al. | |
| 5,112,337 A | 5/1992 | Paulos et al. | |
| 5,122,146 A | 6/1992 | Chapman et al. | |
| 5,139,520 A | 8/1992 | Rosenberg | |
| 5,163,940 A * | 11/1992 | Bourque | A61B 17/1714 606/103 |
| 5,180,388 A | 1/1993 | DiCarlo | |
| 5,312,412 A | 5/1994 | Whipple | |
| 5,314,429 A | 5/1994 | Goble | |
| 5,330,468 A | 7/1994 | Burkhart | |
| 5,350,383 A * | 9/1994 | Schmieding | A61B 17/1714 606/103 |
| 5,374,269 A | 12/1994 | Rosenberg | |
| 5,382,120 A | 1/1995 | Parsons | |
| 5,385,567 A | 1/1995 | Goble | |
| 5,409,493 A | 4/1995 | Greenberg | |
| 5,458,602 A | 10/1995 | Goble et al. | |
| 5,514,144 A | 5/1996 | Bolton | |
| 5,562,664 A | 10/1996 | Durlacher et al. | |
| 5,613,971 A | 3/1997 | Lower et al. | |
| 5,643,273 A | 7/1997 | Clark | |
| 5,671,695 A | 9/1997 | Schroeder | |
| 5,688,284 A | 11/1997 | Chervitz et al. | |
| 5,785,709 A | 7/1998 | Kummer et al. | |
| 5,891,150 A | 4/1999 | Chan | |
| 5,895,389 A | 4/1999 | Schenk et al. | |
| 5,918,604 A | 7/1999 | Whelan | |
| 5,968,050 A | 10/1999 | Torrie | |
| 6,120,511 A | 9/2000 | Chan | |
| 6,132,433 A | 10/2000 | Whelan | |
| 6,162,226 A | 12/2000 | DeCarlo, Jr. et al. | |
| 6,187,011 B1 | 2/2001 | Torrie | |
| 6,200,323 B1 | 3/2001 | Pierson, III | |
| 6,254,606 B1 | 7/2001 | Carney et al. | |
| 6,342,056 B1 | 1/2002 | Mac-Thiong et al. | |
| 6,517,546 B2 | 2/2003 | Whittaker et al. | |
| 6,666,340 B2 | 12/2003 | Basinger et al. | |
| 6,739,872 B1 | 5/2004 | Turri | |
| 6,755,838 B2 | 6/2004 | Trnka | |
| 6,918,916 B2 | 7/2005 | Gobel et al. | |
| 6,958,067 B2 | 10/2005 | Whittaker et al. | |
| 7,066,956 B2 | 6/2006 | Schmieding et al. | |
| 7,077,863 B2 | 7/2006 | Schmieding et al. | |
| 7,131,974 B2 | 11/2006 | Keyer et al. | |
| 7,160,305 B2 | 1/2007 | Schmieding | |
| 7,192,432 B2 | 3/2007 | Wetzler et al. | |
| 7,201,756 B2 | 4/2007 | Ross et al. | |
| 7,299,561 B2 | 11/2007 | Castaneda | |
| 7,306,626 B2 | 12/2007 | Whelan | |
| 7,309,115 B2 | 12/2007 | Blum et al. | |
| 7,575,578 B2 | 8/2009 | Wetzler et al. | |
| 7,588,595 B2 | 9/2009 | Miller et al. | |
| 7,594,917 B2 | 9/2009 | Whittaker et al. | |
| 7,655,011 B2 | 2/2010 | Whittaker et al. | |
| 7,674,290 B2 | 3/2010 | McKernan et al. | |
| 7,753,914 B2 | 7/2010 | Ruhling et al. | |
| 7,842,042 B2 | 11/2010 | Reay-Young et al. | |
| 7,988,697 B2 | 8/2011 | Miller et al. | |
| 8,080,013 B2 | 12/2011 | Whittaker et al. | |
| 8,128,634 B2 | 3/2012 | Whittaker et al. | |
| 8,137,360 B2 | 3/2012 | Whittaker et al. | |
| 8,226,716 B2 | 7/2012 | McKernan et al. | |
| 8,292,894 B2 | 10/2012 | Re | |
| 8,313,492 B2 | 11/2012 | Wong et al. | |
| 8,317,862 B2 | 11/2012 | Troger et al. | |
| 8,491,595 B2 | 7/2013 | Volpi et al. | |
| 8,617,168 B2 | 12/2013 | Bourque et al. | |
| 8,617,176 B2 | 12/2013 | Lizardi et al. | |
| 8,986,314 B1 | 3/2015 | Jordan et al. | |
| 10,010,333 B2 | 7/2018 | Ardito et al. | |
| 10,045,789 B2 | 8/2018 | Ardito et al. | |
| 10,098,646 B2 | 10/2018 | Ardito et al. | |
| 10,307,173 B2 | 6/2019 | Ardito et al. | |
| 2003/0051591 A1 | 3/2003 | Gobel et al. | |
| 2003/0216742 A1 | 11/2003 | Wetzler et al. | |
| 2004/0092936 A1 | 5/2004 | Miller et al. | |
| 2004/0193172 A1 | 9/2004 | Ross et al. | |
| 2006/0069394 A1 | 3/2006 | Weiler et al. | |
| 2006/0264947 A1 | 11/2006 | Orbay et al. | |
| 2008/0103506 A1 | 5/2008 | Volpi et al. | |
| 2008/0171301 A1 | 7/2008 | Verban | |
| 2008/0188935 A1 | 8/2008 | Saylor et al. | |
| 2009/0030417 A1 | 1/2009 | Takahashi | |
| 2009/0163766 A1 | 6/2009 | Torrie et al. | |
| 2009/0171360 A1 | 7/2009 | Whelan | |
| 2009/0228015 A1 | 9/2009 | Ellis et al. | |
| 2009/0306675 A1 | 12/2009 | Wong et al. | |
| 2010/0049196 A1 | 2/2010 | Re | |
| 2010/0049197 A1 | 2/2010 | Re | |
| 2010/0049198 A1 | 2/2010 | Re | |
| 2010/0121338 A1 | 5/2010 | Pandya | |
| 2010/0145340 A1 | 6/2010 | Phan et al. | |
| 2010/0241106 A1 | 9/2010 | Torrie | |
| 2011/0034933 A1 | 2/2011 | Paulos | |
| 2011/0125159 A1 | 5/2011 | Hanson et al. | |
| 2011/0166581 A1 | 7/2011 | Van Der Merwe et al. | |
| 2011/0208198 A1 | 8/2011 | Anderson et al. | |
| 2011/0282350 A1 | 11/2011 | Kowarsch et al. | |
| 2011/0313478 A1 | 12/2011 | Herdrich et al. | |
| 2012/0059382 A1 | 3/2012 | Paulos | |
| 2012/0109132 A1 | 5/2012 | Ellis et al. | |
| 2012/0109136 A1 | 5/2012 | Bourque et al. | |
| 2012/0123417 A1 | 5/2012 | Smith | |
| 2012/0197259 A1 | 8/2012 | Smith | |
| 2012/0253352 A1 | 10/2012 | Smith | |
| 2012/0330323 A1 | 12/2012 | Lizardi et al. | |
| 2013/0030442 A1 | 1/2013 | Pilgeram et al. | |
| 2013/0090658 A1 | 4/2013 | Kam | |
| 2015/0351777 A1 | 12/2015 | Lizardi et al. | |
| 2016/0089159 A1 | 3/2016 | Ardito et al. | |
| 2016/0089160 A1 | 3/2016 | Ardito et al. | |
| 2016/0089161 A1 | 3/2016 | Ardito et al. | |
| 2016/0089162 A1 | 3/2016 | Ardito et al. | |
| 2018/0296229 A1 | 10/2018 | Ardito et al. | |
| 2018/0333161 A1 | 11/2018 | Ardito et al. | |
| 2019/0262014 A1 | 8/2019 | Ardito et al. | |

FOREIGN PATENT DOCUMENTS

| | | |
|---|---|---|
| EP | 1 917 921 A2 | 5/2008 |
| FR | 2 716 364 A1 | 8/1995 |
| FR | 2 948 551 A1 | 2/2011 |
| JP | H05277129 A | 10/1993 |
| JP | 2014-171892 A | 9/2014 |
| JP | 2014-180564 A | 9/2014 |
| WO | 2005/037065 A2 | 4/2005 |
| WO | 2009/052294 A1 | 4/2009 |
| WO | 2012/061733 A1 | 5/2012 |

OTHER PUBLICATIONS

Japanese Office Action for Application No. 2015-190969, dated Jul. 18, 2019 (9 pages).

Chinese Office Action for Application No. 201510642039.8, dated May 14, 2019.

Japanese Office Action for Application No. 2015-190884, dated Nov. 13, 2019 (8 pages).

(56) References Cited

OTHER PUBLICATIONS

[No Author Listed] Kreg Too Company website; Instruction page for Micro Pocket™ Drill Guide; https://www.kregtool.com/webres/Files/KJMICRODGB-Instructions.pdf; accessed Jul. 1, 2015 (2 pages).

[No Author Listed] L.S.Starrett Company website for 252-14 Height Transfer Gage; http://www.starrett.com/metrology/product-detail/Precision-Measuring-Tools/Precision-Hand-Tools/Height-Gages/Other-Height-Gages/252Z-14; accessed Jul. 1, 2015 (3 pages).

[No Author Listed] WonderHowTo website; Instructions for making drill bit depth gauge; http://home-tools.wonderhowto.com/how-to/make-easy-drill-bit-depth-gauge-233680/; accessed Jul. 1, 2015 (4 pages).

Partial European Search Report for Application No. 15187725.5, dated Feb. 9, 2016 (7 pages).

Partial European Search Report for Application No. 15187734.7, dated Feb. 3, 2016 (6 pages).

Partial European Search Report for Application No. 15187739.6, dated Feb. 9, 2016 (7 pages).

Extended European Search Report for Application No. 15187755.2, dated Feb. 5, 2016 (7 pages).

Japanese Office Action for Application No. 2015-190884, dated Jul. 4, 2019 (3 pages).

Chinese Office Action for Application No. 201510640568.4, dated Feb. 26, 2020 (19 pages).

National Intellectual Property Administration, P.R. China Search Report for Application No. 201510640568.4, dated Feb. 16, 2020 (3 pages).

\* cited by examiner

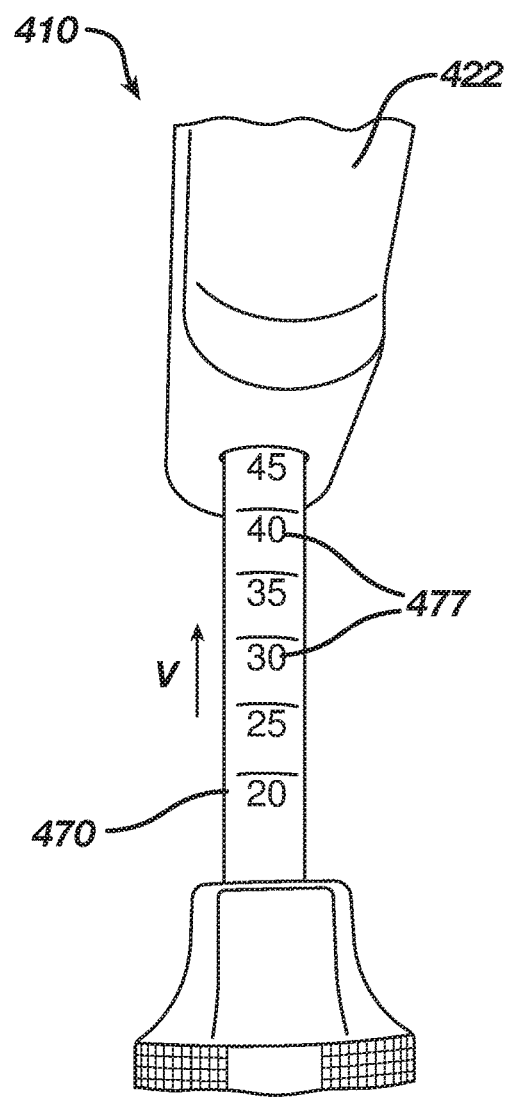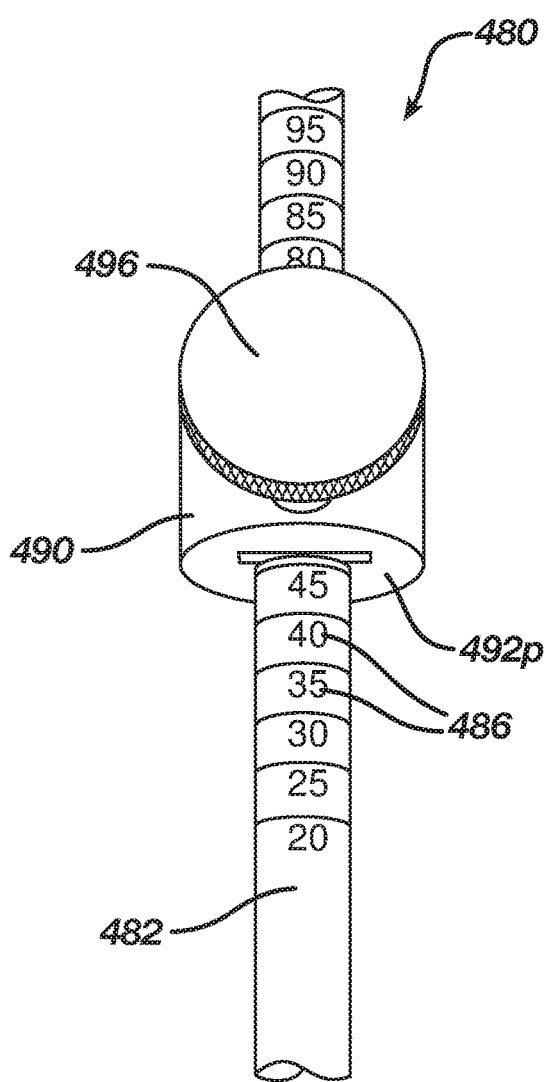
FIG. 23B
FIG. 23C

SURGICAL GUIDE FOR USE IN LIGAMENT REPAIR PROCEDURES

CROSS-REFERENCE TO RELATED APPLICATION

This application is a divisional of U.S. patent application Ser. No. 14/503,178, filed Sep. 30, 2014, and entitled "Surgical Guide for Use in Ligament Repair Procedures," which is hereby incorporated by reference in its entirety.

FIELD

The present disclosure relates to systems, devices, and methods for forming a tunnel or bore in bone, and more particularly relates to a ligament (e.g., ACL and PCL) modular guide, a drill pin depth gage, and components used in conjunction with the guide and gage.

BACKGROUND

Ligaments are tough bands of tissue that serve to connect the articular extremities of bones or to support or retain organs in place within the body. Ligaments are typically composed of coarse bundles of dense white fibrous tissue which are disposed in a parallel or closely interlaced manner, with the fibrous tissue being pliant and flexible, but not significantly extensible. Two well-known ligaments are the anterior and posterior cruciate ligaments (i.e., the ACL and PCL), which extend between the proximal end of the tibia and the distal end of the femur. The ACL and PCL cooperate, together with other ligaments and soft tissue, to provide both static and dynamic stability to the knee.

Ligaments such as the ACL and PCL can tear or rupture for a variety of reasons, including as a result of accidents or overexertion. In fact, the injury of an ACL or PCL is a common sports-related injury. Consequently, various surgical devices and procedures have been developed for reconstructing ACLs and PCLs to restore normal function to the knee. In many instances, the ACL or PCL may be reconstructed by replacing the ruptured ligament with a graft ligament. More particularly, with such procedures, bone tunnels are typically formed in the proximal end of the tibia and the distal end of the femur, with one end of the graft ligament being positioned in the femoral tunnel and the other end of the graft ligament being positioned in the tibial tunnel. The two ends of the graft ligament are anchored in place in various ways known in the art so that the graft ligament extends between the femur and the tibia in substantially the same way, and with substantially the same function, as the original ligament. This graft ligament then cooperates with the surrounding anatomical structures so as to restore normal function to the knee.

Modular guides can be used to help form the bone tunnels in an ACL or PCL graft ligament procedure. The guides help to define a location of the tunnel to be formed in bone and subsequently direct one or more tools for drilling through the bone at the desired tunnel location. One embodiment of a modular guide 10 is provided for in FIGS. 1A and 1B. As shown, the guide 10 includes a frame 12 for receiving both a translatable arm 14 and a bullet 16. The location at which the frame 12 receives the bullet 16 is stationary, while the arm 14 is configured to translate through the frame 12 to set an angle or trajectory of one or more desired bone tunnels, as shown a tibial tunnel 6 and a femoral tunnel 8. As shown, a distal tip 16d of the bullet 16 can be positioned at a desired location for a proximal end 6p, 8p of the bone tunnel 6, 8 and an end 14d of the arm 14 can be positioned at a desired location of a distal end 6d, 8d of the same bone tunnel 6, 8. A thumb screw 18 can be provided to allow a user to lock the location of the translatable arm 14 with respect to the frame 12, thereby setting the angle or trajectory of the desired bone tunnel 6, 8.

Guides of the nature illustrated in FIGS. 1A and 1B can suffer from a number of different problems. For example, a surgeon may end up missing the predetermined target with a drill pin, which is sometimes referred to as divergence. Divergence can occur for a host of reasons. In some instances, divergence occurs because the arm of the modular guide is not securely locked in position with respect to the frame, and thus the intended angle or trajectory moves, causing the drill to miss its intended mark. Alternatively, a surgeon may accidentally disengage the thumb screw because his or her hand is holding the frame near that location in use. Still further, if a change in the intended angle or trajectory needs to be made by the surgeon intra-operatively (as opposed to pre-setting the trajectory), the surgeon may accidentally shift the distal tip of the bullet and/or the end of the arm when adjusting his or her grip to loosen and then tighten the thumb screw. Having the portion of the device that the user operates to define the trajectory coincide with the portion of the device gripped by the user during operation of the device creates and compounds these problems.

In some instances, the tunnel is formed using a retrograde reamer 19 such that after a pilot tunnel is drilled, the retrograde reamer 19 is operated from the distal end 6d, 8d to the proximal end 6p, 8p of the tunnel 6, 8 to enlarge the tunnel. Such a procedure typically involves drilling a pilot hole using the guide and bullet and then disassociating the guide from the reamer before operating the reamer so that the guide does not constrict the surgeon operating the reamer. In order to disassociate the guide from the reamer though, the bullet must first be removed by sliding it up the shaft of the retrograde reamer. Then the guide is removed and the bullet can be slid back down the shaft of the reamer so that the bullet can assist with keeping the desired trajectory of the reamer during cutting. Because of this set-up, the shaft of the retrograde reamer must be longer than would be necessary just for cutting because extra length is needed to allow the bullet to be slid far enough up the reamer 19 that the distal tip 16d of the bullet 16 is proximal of the frame 12 while still keeping the reamer at the distal end of the bone tunnel. This, in turn, allows the frame 12 to be disassociated from the bullet 16 so that the frame 12 and arm 14 can be removed from the surgical site. Of course, the extra length of the reamer can increase the likelihood of divergence due to flexing of the long retrograde reamer shaft. When divergence does occur, the surgeon will typically have to re-drill or make further adjustments to the implant, related components, and/or the surgical procedure to account for the incorrectly located bone tunnel. Such adjustments are typically less desirable than correctly drilling the tunnel to start.

Guides of the nature illustrated in FIGS. 1A and 1B are further deficient because they are not universal. A right-handed surgeon and a left-handed surgeon typically need different guides so that controls such as the thumb screw are appropriately located for the various procedures with which the guides can be used. Likewise, the configuration of existing guides do not lend themselves to be used from any side of either knee with either the right hand or left hand without modifying the device or having the surgeon contort his or her body to use the guide.

A further problem that plagues surgeons during ACL and PCL reconstruction procedures is over-drilling, i.e., extending the dill pin further distally than the desired distal end of the bone tunnel. In either procedure, but particularly during PCL repairs, it can be crucial to insure that the drill pin is not over-drilled to prevent undesirable damage to the surrounding tissue and the like. For example, during a PCL repair, over-drilling can risk damage to the femoral articular cartilage and/or can puncture the neurovascular structure in the posterior portion of the knee.

Accordingly, there remains a need for improved systems, devices, and methods for use in performing ligament repairs that decrease the risk of divergence and/or over-drilling and improve the ability for such systems, devices, and methods to be used universally, i.e., such that the same systems, devices, and methods can be used with either hand, on either knee to form tibial and femoral tunnels, while sitting or standing in the same location.

SUMMARY

Devices, systems, and methods are generally provided for ligament repair procedures such as procedures performed in ligament (e.g., ACL and PCL) reconstruction surgeries. The devices and systems provided for relate to surgical guides used to establish a location and trajectory for forming a bone tunnel in bone. The surgical guides provided for afford a number of advantages, including limiting the risk of divergence to improve the accuracy of bone tunnel formation. The disclosures herein also provide for various embodiments of carriages, which can be a component of a surgical guide and can be used to receive a bullet for use in various repair procedures. The carriages provided for also afford a number of advantages, including allowing for shorter drilling tools, which decreases the risk of divergence. They also allow for the portion of the device involved in setting the angle or trajectory of the bone tunnel formation to be separate from the portion of the device gripped by the user during operation. Still further, the devices and systems provided for herein include a drill pin depth gage that can be used to help set a length of a drill pin to prevent the pin from traveling further than desired when drilling a bone tunnel in bone. This, in turn, decreases a risk of damaging surrounding tissue, nerves, and other aspects of the body.

In one exemplary embodiment, a surgical instrument includes a guide arm and a carriage. The guide arm has a first portion that is configured to define an angle at which a bore is to be drilled into bone and a second portion that is configured to define a location of a distal end of the bore to be drilled into bone. An angle extending between the first and second portions can be approximately 110 degrees or less. The carriage can be disposed on the first portion of the guide arm. The carriage can have a length that is greater than a width or a thickness thereof, and the length of the carriage can extend substantially transverse to a length of the first portion of the guide arm. The carriage can be configured to translate along a length of the first portion. Further, the carriage can be configured to be selectively located at different locations along the length of the first portion to set the angle or trajectory at which a bore is to be drilled into bone.

The carriage can include a bullet-receiving opening formed therein that is configured to receive a bullet. In some embodiments, the surgical instrument can include a bullet. The bullet can be configured to be removably coupled to the carriage and, when coupled to the carriage, the bullet can be configured to define a location of a proximal end of the bore to be drilled into bone. The bullet can be tapered towards its distal end. It can also be cannulated. A proximal face of the bullet can have a width that is greater than a diameter of a distal portion of the bullet, and the proximal face can be concave to facilitate insertion of tools into a bore extending through the bullet.

The first portion of the guide arm can include opposed first and second flat surfaces and first and second sidewalls that extend between the first and second flat surfaces. The surface areas of the flat surfaces can be substantially larger than the surface areas of the sidewalls. The carriage can include first and second facial surfaces, as well as first and second side surfaces that extend between the first and second facial surfaces. The first and second flat surfaces of the guide arm can extend substantially parallel to the first and second facial surfaces, with the first facial surface of the carriage facing away from the first flat surface of the first portion of the guide arm. The bullet-receiving opening can be formed in the first facial surface of the carriage. The carriage can be configured such that a bullet received by the bullet-receiving opening is held at an angle with respect to the second flat surface such that a drill pin extending through a bullet disposed in the bullet-receiving opening is configured to engage a distal end of the second portion of the guide arm that defines the location of the distal end of the bore to be drilled into bone. The second portion of the guide arm can include a distal tip disposed at a terminal end of the second guide arm. The distal tip can be configured to engage bone at an intended location of the distal end of the bore to be drilled into bone.

In some embodiments, the first portion of the guide arm is not movable with respect to the second portion of the guide arm when the first and second arms are coupled together. The first portion of the guide arm can include a plurality of slots formed therein, with each slot being indicative of an intended angle at which the bore is to be drilled into bone. Each slot of the plurality of slots can be disposed at locations such that the intended angles are at intervals of five degrees along the first portion. The carriage can include a passive locking mechanism that is configured to passively engage a slot of the plurality of slots to set the angle at which the bore is to be drilled into bone. The passive locking mechanism can include a selectively deployable key having a configuration that is complementary to the plurality of slots such that when the selectively deployable key is disposed in a slot, the location of the carriage is fixed with respect to the first portion of the guide arm. The passive locking mechanism can also include a button configured to disengage the selectively deployable key from a slot of the plurality of slots to allow the carriage to translate a long a length of the first portion. The selectively deployable key can be disposed on a bar that extends between a proximal end and a distal end of the carriage. The bar can have an opening formed therein that allows indicia associated with the plurality of slots to be viewable.

In another exemplary embodiment, a surgical guide for use in conjunction with drilling a bore in bone includes a first arcuate arm, a second arm, and a bullet configured to be removably associated with the first arcuate arm. The first arcuate arm can have a first end, a second end, and an intermediate portion extending therebetween, with the intermediate portion having indicia formed on it to indicate an intended angle at which a bore is to be drilled into bone. The second arm can also have a first end, a second end, and an intermediate portion extending therebetween. The first end of the second arm can be directly connected to the second end of the first arm to form a unitary construction of the guide such that the second arm is substantially stationary with respect to the first arm, and an angle extending between the first and second arms is approximately 110 degrees or less. The removable association between the bullet and the first arm can be such that a location of the bullet with respect to the indicia formed on the arm reflects an intended angle at which a distal tip of the bullet is to form with the bone in which the bore is to be drilled, which in turn defines the intended angle or trajectory of the bore to be drilled into the bone.

The first arm can include opposed first and second flat surfaces and first and second sidewalls that extend between the first and second flat surfaces. The surface areas of the flat surfaces can be substantially larger than the surface areas of the sidewalls. In some embodiments, the indicia can also include a plurality of slots formed on a surface of the first arcuate arm. Each slot of the plurality of slots can be disposed at locations such that the intended angles are at intervals of five degrees along the first arm. The second end of the second arm can include a distal tip that is configured to engage bone at an intended location of a distal end of the bore to be drilled into the bone.

The bullet can be tapered towards its distal end. It can also be cannulated. A proximal face of the bullet can have a width that is greater than a diameter of a distal portion of the bullet, and the proximal face can be concave to facilitate insertion of tools into a bore extending through the bullet.

In some embodiments, the guide can include a carriage that is configured to receive the bullet. The carriage can translate along a length of the first arm, and can be selectively locked with respect to the indicia to set the intended angle formed by the distal tip of the bullet with the bone in which the bore is to be drilled. This, in turn, sets the intended angle or trajectory of the bore to be drilled in the bone. The carriage can include first and second opposed facial surfaces and first and second side surfaces extending between the first and second facial surfaces. The first facial surface of the carriage can face away from the first arcuate arm. The carriage can be configured such that the bullet received by the carriage is held at an angle with respect to the first arcuate arm such that a distal tip of a drill pin extending through the bullet is configured to engage a distal tip of the second arm. In some embodiments, the carriage can include a bullet-receiving opening that is configured to receive the bullet.

In some embodiments in which the indicia include a plurality of slots formed in a surface of the first arcuate arm, the carriage can include a passive locking mechanism configured to passively engage a slot of the plurality of slots to set the intended angle or trajectory of the bore to be drilled into bone. The passive locking mechanism can include a selectively deployable key having a configuration that is complementary to the plurality of slots such that when the selectively deployable key is disposed in a slot, the location of the carriage is fixed with respect to the first arm. The passive locking mechanism can also include a button configured to disengage the selectively deployable key from a slot of the plurality of slots to allow the carriage to translate a long a length of the first arm. The selectively deployable key can be disposed on a bar that extends between a proximal end and a distal end of the carriage. The bar can have an opening formed therein that allows indicia associated with the plurality of slots to be viewable.

An exemplary method for drilling a bore in bone can include positioning a second end of a second arm of a surgical guide adjacent to a desired location for a distal end of a bore to be drilled in bone, and positioning a first end of a first arm of the surgical guide proximate to an opposed side of the bone, the opposed side being the location at which a proximal end of the bore to be drilled in bone is to be located. The first arm can be disposed in a hand of a user such that no additional component of the surgical guide is disposed therebetween. The method can further include adjusting the surgical guide to set an angle between a distal tip of a bullet that is to be associated with the surgical guide and the bone to be drilled. This adjustment occurs without moving the first arm relative to the second arm, and the angle is formed at the location at which the proximal end of the bore is to be drilled. The method can further include disposing a drill pin in a through-bore of the bullet, and operating the drill pin to drill a hole from the location at which the distal tip of the bullet forms an angle with the bone to the location at which the second end of the second arm is located.

In some embodiments, adjusting the surgical guide to set an angle between a distal tip of a bullet that is to be associated with the surgical guide and the bone to be drilled includes locking a location of a carriage on the first arm. The carriage can be configured to receive the bullet and can also be configured to translate a length of the first arm to establish different angles at which the angle between the distal tip of the bullet and the bone can be set.

The first arm can include a plurality of slots formed therein, and the carriage can include a passively engaging male member that is configured to engage a slot of the plurality of slots as part of the step of locking a location of the carriage on the first arm. In such embodiments, the method can include actively disengaging the male member from the slot, moving the carriage along the first arm, and allowing the male member to engage a slot of the plurality of slots to lock the location of the carriage on the first arm. Actively disengaging the male member from the slot can include pushing a button associated with the carriage and subsequently releasing the button prior to allowing the male member to engage a slot of the plurality of slots.

The method can also include a step of coupling the drill pin to a chuck of a surgical drill such that a distal tip of the drill pin extends no further distally than the second end of the second arm located adjacent to the distal end of the bore.

In one exemplary embodiment of a carriage for use with a surgical guide, the carriage includes a housing having a proximal end, a distal end opposed to the proximal end, opposed first and second side surfaces that extend between the proximal and distal ends, and opposed first and second facial surfaces that extend between the proximal and distal ends and the first and second side surfaces. A guide-receiving opening can extend through the housing and through the first and second side surfaces. The guide-receiving opening can be configured to receive an arm of a surgical guide along which the carriage is configured to translate. A bullet-receiving opening can extend through the housing and through the proximal and distal ends. The bullet-receiving opening can be configured to be open towards the first facial surface to receive a bullet for use with a surgical guide associated with the carriage. The guide-receiving opening and the bullet-receiving opening can extend in different planes, and can be substantially transverse to each other.

In some embodiments, the bullet-receiving opening can be configured to receive a bullet by passing the bullet from an outside environment, across a plane extending substantially through the first facial surface, and into the bullet-receiving opening. Further, the bullet-receiving opening can be configured to hold a received bullet in a locked position in which the received bullet cannot translate between the two side surfaces or between the two facial surfaces. A rotatable receiver can be disposed in the housing. The rotatable receiver can extend from the proximal end to the distal end, with the bullet-receiving opening being disposed in the rotatable receiver. The rotatable receiver can be rotatable between a receiving position in which the bullet-receiving opening is open towards the first facial surface to receive a bullet for use with a surgical guide associated with the carriage, and a locking position in which the bullet-receiving opening is rotated towards the second facial surface and the bullet is in the locked position.

A bullet engagement protrusion can extend through the rotatable receiver and can be configured to engage an engagement slot of a bullet disposed in the bullet-receiving opening to maintain the bullet in the locked position. A release button can be provided to disengage the bullet engagement protrusion from an engagement slot of a bullet disposed in the bullet-receiving opening to remove the bullet from the locked position. The release button can be in communication with the bullet engagement protrusion to provide the disengagement. In some embodiments, the carriage also includes a bullet configured to be removably disposed in the bullet-receiving opening.

A receiving ramp can be disposed within the housing. The receiving ramp can be configured to receive the rotatable receiver and maintain it in the locking position to maintain a bullet disposed in the bullet-receiving opening in the locked position. Further, in some embodiments the rotatable receiver can include opposed indents formed in its proximal end. A surface of the first indent can be configured to engage the ramp when the rotatable receiver is in the locking position, and a surface of the second indent can be configured to engage the ramp when the rotatable receiver is in the receiving position.

The second facial surface can include a top portion and a bottom portion with an opening extending therebetween, and can also include a portion of a surgical guide engagement feature disposed in the opening that extends between the top and bottom portions to bound the guide-receiving opening. The surgical guide engagement feature can be configured to translate longitudinally between the proximal and distal ends to selectively lock a location of the carriage with respect to a surgical guide. The surgical guide engagement feature can include a passively engaging male member that is configured to engage a slot disposed on an arm of a surgical guide.

In another exemplary embodiment of a carriage for use with a surgical guide, the carriage includes a housing and a bullet receiver rotatably coupled to the housing. The housing can have a guide-receiving opening formed therein, with the guide-receiving opening being configured to receive an arm of a surgical guide along which the carriage is configured to translate. The bullet receiver can have a bullet-receiving opening formed in it to receive a bullet for use with a surgical guide associated with the carriage. The bullet receiver can rotate between a receiving position in which the bullet receiving opening is open towards an environment outside of the housing to receive a bullet for use with a surgical guide associated with the carriage, and a locking position in which the bullet-receiving opening is rotated towards the housing to place a bullet disposed therein in a locked position in which the received bullet cannot translate between the two side surfaces or between the two facial surfaces of the housing. In the locking position, the bullet can translate distally. The bullet receiver can also have an intermediate position in which the bullet is received in the bullet receiving opening and the bullet is able to translate freely both distally and proximally.

In some embodiments, the carriage can include a bullet engagement protrusion that extends through the bullet receiver and can be configured to engage an engagement slot of a bullet disposed in the bullet-receiving opening to maintain the bullet in the locked position. A release button can be provided to disengage the bullet engagement protrusion from an engagement slot of a bullet disposed in the bullet-receiving opening to remove the bullet from the locked position. The release button can be in communication with the bullet engagement protrusion to provide the disengagement. In some embodiments, the carriage also includes a bullet configured to be removably disposed in the bullet-receiving opening.

A receiving ramp can be disposed within the housing. The receiving ramp can be configured to receive the bullet receiver and maintain it in the locking position to maintain a bullet disposed in the bullet-receiving opening in the locked position. Further, in some embodiments the bullet receiver can include opposed indents formed in its proximal end. A surface of the first indent can be configured to engage the ramp when the bullet receiver is in the locking position, and a surface of the second indent can be configured to engage the ramp when the bullet receiver is in the receiving position.

A surgical guide engagement feature can be provided as part of the carriage. The surgical guide engagement feature can be configured to translate longitudinally and thus substantially transverse to an axis extending through the guide-receiving opening to selectively lock a location of the carriage with respect to a surgical guide. The surgical guide engagement feature can include a passively engaging male member that is configured to engage a slot disposed on an arm of a surgical guide.

The various embodiments of the carriage provided for can be used in conjunction with a surgical instrument that includes a surgical guide having an elongate arm. The elongate arm can be disposed in the guide-receiving opening of the carriage such that the carriage is translatable along the elongate arm. The carriage can be configured to selectively lock to maintain a location of the carriage with respect to the elongate arm.

An exemplary surgical method provided for herein includes setting a surgical guide to define a path for a retrograde reamer to drill a bore in bone at a surgical site. The path can be set such that a distal tip of a bullet coupled to the surgical guide is located proximate to a desired location for a proximal end of the bore. The method can further include drilling a pilot hole in the bone along the defined path using a drill pin end of a retrograde reamer. The bullet can then be decoupled from the surgical guide, and the surgical guide can be removed from the surgical site. The process of decoupling the bullet from the surgical guide can be accomplished without removing the retrograde reamer from the bullet. A reamer associated with the drill pin can then be operated to expand the pilot hole formed in bone by advancing the reamer proximally.

In some embodiments, the step of setting a surgical guide to define a path for a reamer can include positioning a second end of a second arm of the surgical guide adjacent to a desired location for a distal end of a bore to be drilled in bone, and positioning a first end of a first arm of the surgical guide proximate to an opposed side of the bone, the opposed side being the location at which a proximal end of the bore to be drilled in bone is to be located. The step can further include adjusting the surgical guide to set an angle between the distal tip of the bullet and the bone to be drilled, the angle being formed at the location at which the proximal end of the bore is to be drilled.

The surgical guide used in the method can have a carriage disposed along an arm of the guide. The carriage itself can have a housing and a bullet-receiving opening, and the bullet can be coupled to the surgical guide by being disposed in the bullet-receiving opening. In some embodiments, the bullet can be rotated in a first direction within the bullet-receiving opening to set the bullet in a locked position in which the bullet cannot translate away from and substantially perpendicular to the arm of the carriage. Further, the bullet can be decoupled from the surgical guide by rotating the bullet in a second direction, opposite to the first direction, such that the bullet is removed from the locked position and is able to be moved away from and substantially perpendicular to the arm of the carriage. Alternatively, the bullet can be decoupled from the surgical guide by activating a release button associated with the carriage such that the bullet is removed from the locked position and is able to be moved away from and substantially perpendicular to the arm of the carriage. When the bullet is in the locked position, it can be configured to translate distally, but not proximally.

In some embodiments the carriage can be configured to translate along a length of the arm to establish different angles at which the angle between the distal tip of the bullet and the bone can be set. In such embodiments, the method can include locking a location of the carriage on the arm of the surgical guide. The arm can include a plurality of slots formed therein and the carriage can include a passively engaging male member that is configured to engage a slot of the plurality of slots as part of the step of locking a location of the carriage on the arm of the surgical guide. In such embodiments, the method can include actively disengaging the male member from the slot, moving the carriage along the first arm, and allowing the male member to engage a slot of the plurality of slots to lock the location of the carriage on the first arm. Actively disengaging the male member from the slot can include pushing a button associated with the carriage and subsequently releasing the button prior to allowing the male member to engage a slot of the plurality of slots.

The method can also include a step of coupling the drill pin to a chuck of a surgical drill such that a distal tip of the drill pin extends no further distally than the second end of the second arm located adjacent to the distal end of the bore. A length of the shaft of the reamer can be approximately equal to a length of the bullet and a length of the bore drilled in bone.

In one exemplary embodiment of a university surgical guide system, the system can include a guide arm and a carriage. The guide arm can have a first portion configured to define a trajectory or angle at which a bore is to be drilled into bone and a second portion configured to define a location of a distal end of the bore to be drilled into bone. The first portion can have opposed surfaces thereof, and each of the opposed surfaces can have formed therein a plurality of slots. Each slot can be indicative of an intended trajectory or angle for the bore to be drilled into bone. The carriage can be disposed on the first portion of the guide arm, and can be configured to translate along a length of the first portion. Further, the carriage can be configured to selectively lock within a slot of the plurality of slots to set the intended trajectory at which the bore is to be drilled into bone.

The carriage can include a bullet-receiving opening that is formed in the carriage. The bullet-receiving opening can be configured to receive a bullet. In some embodiments, the system can include a bullet. The bullet can be configured to be removably coupled to the carriage and, when coupled to the carriage, the bullet can be configured to define a location of a proximal end of the bore to be drilled into bone. In some embodiments, the carriage can be configured such that a bullet received by the bullet-receiving opening is held at an angle with respect to the first portion of the guide arm such that a distal tip of a drill pin extending through a bullet disposed in the bullet-receiving opening is configured to engage a distal end of the second portion of the guide arm that defines the location of the distal end of the bore to be drilled into bone.

The carriage can include a passive locking mechanism that is configured to passively engage a slot of the plurality of slots to set the trajectory or angle at which the bore is to be drilled into bone. The passive locking mechanism can include a selectively deployable key that has a configuration that is complementary to the plurality of slots such that when the selectively deployable key is disposed in a slot, the location of the carriage is fixed with respect to the first portion of the guide arm. In some embodiments the passive locking mechanism can include a button configured to disengage the selectively deployable key from a lot of the plurality of slots to allow the carriage to translate along a length of the first portion.

In some embodiments the first portion of the guide arm is not movable with respect to the second portion when the first and second portions are coupled together. A second portion of the guide arm can include a distal tip that is disposed at a terminal end of the second guide arm. The distal tip can be configured to engage bone at an intended location of the distal end of the bore to be drilled into bone.

In another exemplary embodiment of a universal surgical guide system, the system can include a guide portion and a locking portion. The guide portion can be configured to define a location and a trajectory of a bore to be drilled in bone, and further, can be configured to be gripped by a user when the system is in use. The locking portion can be configured to work in conjunction with the guide portion to define the location and the trajectory of the bore to be drilled in bone, and further, can be configured to lock the guide system, thereby defining the trajectory of the bore. The system can be set-up such that a trajectory of the bore can be adjusted and locked without a grip of a user on the guide portion being adjusted.

In some embodiments, the locking portion can include a carriage configured to slide along the guide portion. The carriage can be locked with respect to the guide portion without a user adjusting a grip of the user formed on the guide portion. The guide portion can have formed therein a plurality of slots on opposed surfaces thereof, with each slot being indicative of an intended trajectory for the bore to be drilled into bone. In some embodiments, the guide portion can have formed thereon designated trajectories that correlate to the trajectory of the bore. A lowest designated trajectory for the bore can be in the range of about 20 degrees to about 40 degrees lower than a highest designated trajectory for the bore. In one exemplary embodiment, the range of designated trajectories is 30 degrees.

The system can be set-up such that the locking portion can be operated with either hand of a user without the user having to move components of the system to adapt it for use with a different hand. The system can also be set-up such that the locking portion can be operated from either side of a patient by a user without moving components of the system to adapt it for use from a different side.

An exemplary method for drilling a tunnel in bone includes grasping a first arm of a ligament guide system in a palm of the hand, with fingers of the hand being wrapped around the first arm. A second end of a second arm of the ligament guide system is positioned adjacent to a desired location for a distal end of a tunnel to be drilled in bone, while a first end of the first arm is positioned proximate to an opposed side of the bone, which is the side at which a proximal end of the tunnel to be drilled in bone is to be located. A carriage disposed on the first arm is slid along a length of the first arm and a location of the carriage is locked with respect to the first arm to set a trajectory of the tunnel to be drilled in bone. The carriage is able to be slid along the first arm while the hand grasping the first arm maintains the grasp such that the hand does not move with respect to the first arm. A drilling tool is passed through an opening formed in the carriage to drill a tunnel in the bone from the side of the bone at which the first end of the first arm is located to the side of the bone at which the second end of the second arm is located.

In some embodiments, a bullet can be used in conjunction with the ligament guide system. The method can include positioning a bullet in the opening formed in the carriage and positioning a distal end of the bullet adjacent to a desired location for the proximal end of the tunnel to be drilled in bone. When the drilling tool is passed through the opening formed in the carriage, it can also be passed through the bullet. The method can further include disassociating the bullet from the guide arm such that the guide arm can be removed from the surgical site without removing the drilling tool from the bullet. The drilling tool can then be passed from the distal end of the tunnel to the proximal end of the tunnel to expand a diameter of the tunnel.

The first arm can have a plurality of slots formed in it and the carriage can include a passively engaging male member that is configured to engage a slot of the plurality of slots to lock a location of the carriage with respect to the first arm to set the trajectory of the tunnel to be drilled in bone. In some embodiments, the method can further include actively disengaging the male member from the slot, moving the carriage along the first arm, and allowing the male member to engage a slot of the plurality of slots to lock the location of the carriage on the first arm. In some embodiments, the first arm of the ligament guide system can be configured to be grasped by either a right hand or a left hand and used to perform the method when held by either hand.

One exemplary instrument for setting a drill pin depth includes an elongate shaft and a depth indicator. The shaft has a proximal end, a distal end, and a channel formed in the shaft that extends from the proximal end and toward the distal end. The channel is configured to receive a drill pin of a ligament drill guide. The depth indicator has a bore formed therein that is configured to receive the elongate shaft. The indicator is configured to selectively engage the elongate shaft to set a fixed location of the depth indicator with respect to the elongate shaft. The fixed location at which the depth indicator is set establishes a terminal distal travel location for a drill pin disposed in the channel such that the drill pin is unable to extend distally past the terminal distal travel location.

A distal portion of the elongate shaft can have indicia formed thereon. The indicia can be indicative of the terminal distal travel location. A distal portion of the elongate shaft can also have a plurality of grooves formed thereon. In conjunction with the same, the depth indicator can include a selectively deployable groove engagement feature that is configured to engage a groove of the plurality of grooves to set the fixed location of the depth indicator with respect to the elongate shaft. In some embodiments, the indicia and grooves are both provided on the distal portion of the elongate shaft. The depth indicator can include a button that is in mechanical cooperation with the selectively deployable groove engagement feature such that depressing the button toward the elongate shaft causes the selectively deployable groove engagement feature to move radially away from the plurality of grooves and releasing the button causes the selectively deployable groove engagement feature to move radially towards the plurality of grooves.

A stationary protrusion can be included as part of the depth indicator. The protrusion can be configured to fit within a channel of the elongate shaft to prevent significant rotation of the depth indicator with respect to a longitudinal axis extending through a length of the elongate shaft. In some embodiments, a diameter or width of the channel at the proximal end of the elongate shaft can be larger than a diameter or width of the channel at a distal end of the channel.

In some embodiments, the instrument can include a drill pin and a chuck of a drill for use with the shaft and depth indicator. The drill pin can have a distal portion and an intermediate portion each having a diameter that is smaller than a diameter or width of the channel such that the distal and intermediate portions are disposable in the channel, and a proximal portion configured to be coupled to the chuck of the drill. The drill can be configured such that a diameter of a distal portion thereof is larger than a diameter or width of the channel such that the distal portion of the drill is configured to abut the proximal end of the elongate shaft while the distal and intermediate portions of the drill pin are disposed in the channel of the elongate shaft. In a configuration in which the distal portion of the drill abuts the proximal end of the elongate shaft, a distal terminal end of the drill pin can be configured to abut a proximal face of the depth indicator.

One exemplary method for drilling a bore in bone can include setting a drill pin depth limit on a drill pin depth gage and attaching a drill pin to a chuck of a drill based on the set drill pin depth limit. The resulting configuration for the drill pin being attached to the chuck of the drill is one in which, in use, a distal tip of the drill pin does not extend distally beyond the drill pin depth limit when a distal portion of the drill engages a proximal terminal end of a bullet in which the drill pin is disposed.

In some embodiments, the method can include determining a bone stock measurement, and setting a drill pin depth limit can be based on the determined bone stock measurement. The bone stock measurement can be determined, for example, by placing a distal tip of an arm of a ligament drill guide on a bone to be drilled at a location at which a second end of a bore is to be formed in the bone, placing a distal tip of a bullet coupled to the ligament drill guide on the bone to be drilled at a location at which a first end of the bore is to be formed in the bone, and reading indicia indicative of the bone stock measurement that is formed on the bullet.

The drill pin depth gage can be used in conjunction with the method can include an elongate shaft and a depth indicator. In such embodiments, setting a drill pin depth limit on a drill pin depth gage can include locking a location of the depth indicator with respect to the elongate shaft to set the drill pin depth limit. Further, attaching a drill pin to a chuck of a drill based on the set drill pin depth limit can include contacting a proximal face of the depth indicator with a distal tip of the drill pin, and engaging a proximal portion of the drill pin with the drill such that the distal portion of the drill engages a proximal terminal end of the elongate shaft of the drill pin depth gage. In some embodiments that include a drill pin depth gage having an elongate shaft and a depth indicator, setting a drill pin depth limit on a drill pin depth gage can include sliding the depth indicator along the elongate shaft and selectively deploying a groove engagement feature to engage a groove of a plurality of grooves formed in the elongate shaft to lock the location of the depth indicator with respect to the elongate shaft to set a desired drill pin depth limit.

The method for drilling a bore in bone can further include drilling a bore in bone until a distal portion of the drill engages a proximal terminal end of a bullet in which the drill pin is disposed. When the distal portion of the drill is engaged with the proximal terminal end of the bullet, the distal tip of the drill pin can be disposed at a distal end of the bore drilled through the bone.

The present disclosure also provides for an exemplary method for attaching a surgical drill pin to a surgical drill that is used in conjunction with a ligament drill guide and a bullet. The method can include determining a bone stock measurement, determining a length of a bullet used in conjunction with a ligament drill guide, coupling a drill pin to a chuck of a surgical drill such that a length of the exposed portion of the drill pin distal of the chuck is equal to the bone stock measurement and the length of the bullet.

In some embodiment, determining a bone stock measurement can include placing a distal tip of an arm of a ligament drill guide on a bone to be drilled at a location at which a second end of a bore is to be formed in the bone, placing a distal tip of a bullet coupled to the ligament drill guide on the bone to be drilled at a location at which a first end of the bore is to be formed in the bone, and reading indicia indicative of the bone stock measurement that is formed on the bullet.

The method can also include disposing the drill pin in a drill pin depth gage. In some embodiments, the gage can be configured to be set such that a length of the drill pin disposed in the drill pin depth gage is equal to the length of the exposed portion of the drill pin distal of the chuck. In some other embodiments, the drill pin depth gage can have indicia formed thereon to indicate the bone stock measurement. In such embodiments, when a distal portion of the drill engages a proximal terminal end of the drill pin depth gage, a distal tip of the drill pin can be located at indicia indicative of the determined bone stock. In still other embodiments, the drill pin depth gage can have a movable depth indicator configured to be set at a plurality of desired locations along a length of the drill pin depth gage, with a desired location of the plurality of desired locations being based on the determined bone stock measurement. In such embodiments, coupling a drill pin to a chuck of a surgical drill can include engaging a distal tip of the drill pin with a proximal face of the depth indicator, and engaging a distal portion of the drill with a proximal terminal end of the drill pin depth gage.

BRIEF DESCRIPTION OF DRAWINGS

This invention will be more fully understood from the following detailed description taken in conjunction with the accompanying drawings, in which:

FIG. 23B is a detailed side view of the bullet disposed in the modular guide of FIG. 23A;

FIG. 23C is a detailed front view of one exemplary embodiment of a drill pin depth gage set at a particular depth based on the bone stock measurement illustrated in FIG. 23B;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, to the extent that a component is described using a numerical reference, e.g., "first arm" or "second arm," such reference does not have any significance, and thus it in no way indicates any particular order, placement, location, etc. of the component with respect to any other component, object, step, etc. In fact, such numerical references can be used interchangeably. For instance, a component described in the specification as a "first arm" or "first portion" can be recited in the claims as a "second arm" or "second portion." A person skilled in the art would be able to understand such interchangeable usage. Likewise, to the extent components are described using positional references, e.g., "front end" or "back end," such reference is not limiting to only such a view. A person skilled in the art would be able to understand how a side of a device can be described as a "front end" in one view can become a side, back, top, or bottom end in another view. Such descriptions in no way limit the perspectives described or claimed herein.

In the present disclosure, like-numbered components of the embodiments generally have similar features and/or purposes. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the components of the modular guide systems and related components, including drill pin depth gages, can depend, at least in part, on the sizes and shapes of the other components with which the components are being used, the anatomy of the subject being operated on, and the type of procedure being performed.

Figure 2:
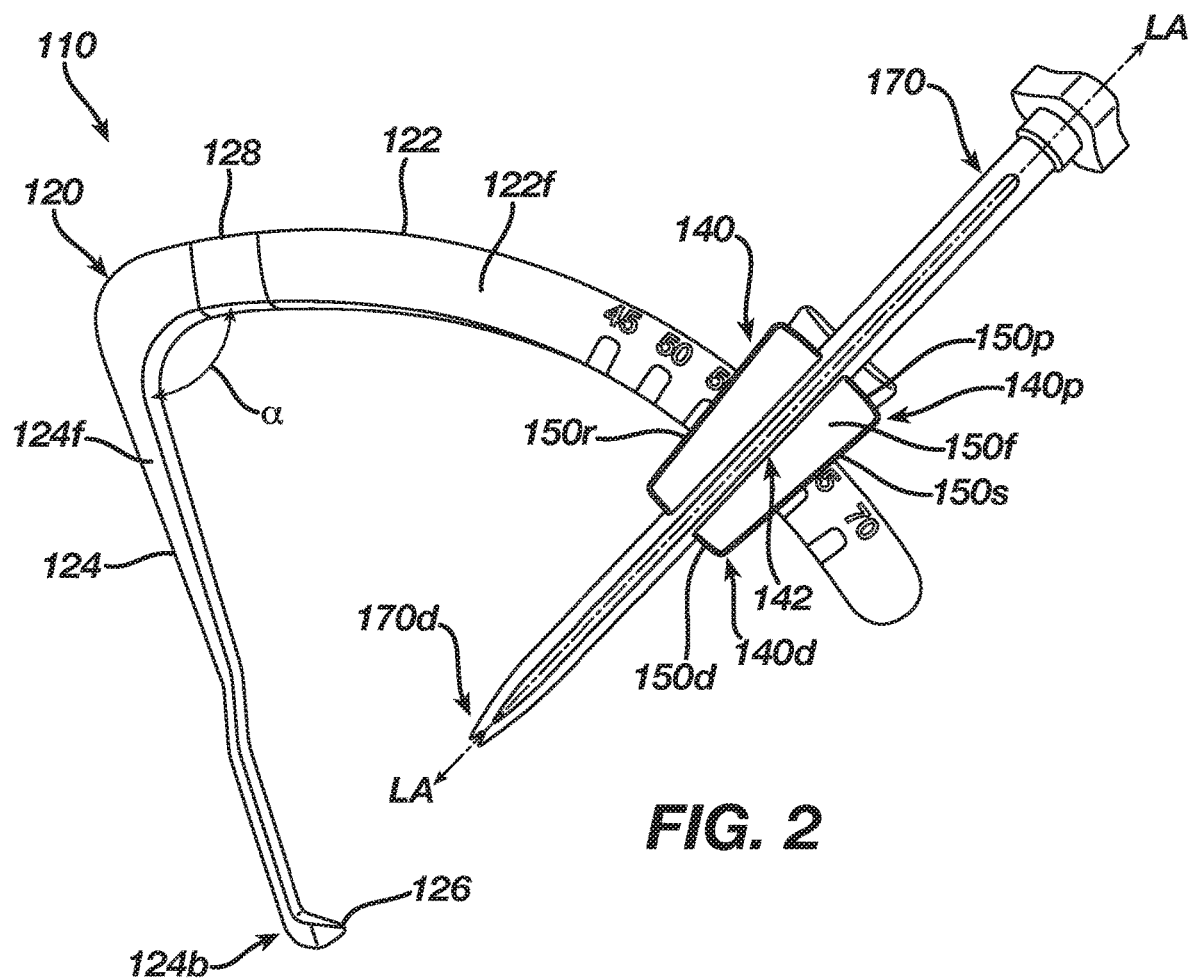
FIG. 2 is a front perspective view of one exemplary embodiment of a modular guide, the guide having a bullet disposed in a carriage thereof.
Figure 3:
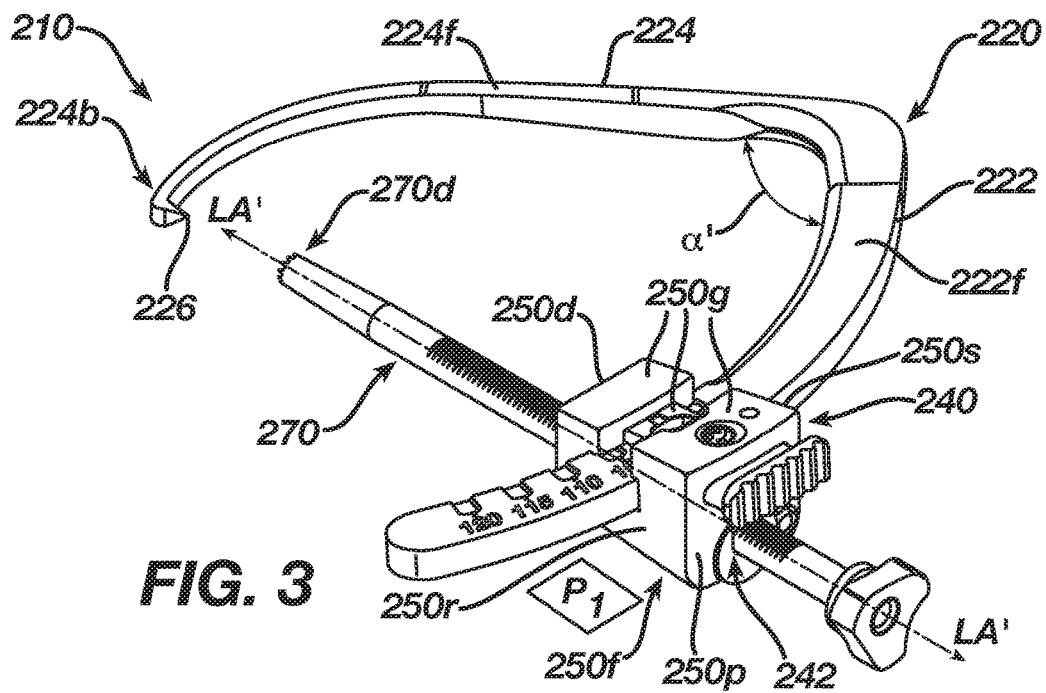
FIG. 3 is an isometric view of another exemplary embodiment of a modular guide, the guide having a bullet disposed in a carriage thereof.

The present disclosure generally provides for surgical guides that can be used in ligament repair procedures, such as repair procedures for the ACL and PCL. Two exemplary embodiments of surgical guides 110, 210, also referred to as modular guides, are illustrated in FIGS. 2 and 3. Surgical guides described herein generally rely on a combination of a guide arm 120, 220 and a carriage 140, 240 configured to slide along at least a portion of the guide arm 120, 220. The carriage 140, 240 can be selectively locked at locations along the guide arm 120, 220 to set a desired location and trajectory for a bone tunnel or bore to be drilled in conjunction with a ligament repair procedure. The carriage 140, 240 can also be configured to receive a bullet 170, 270, which itself can be used in conjunction with the guide 110, 210 to set the desired location and trajectory of the bone tunnel or bore to be drilled. The terms tunnel and bore will be used interchangeably throughout the specification as it pertains to forming a hole in a bone.

Figure 9A:
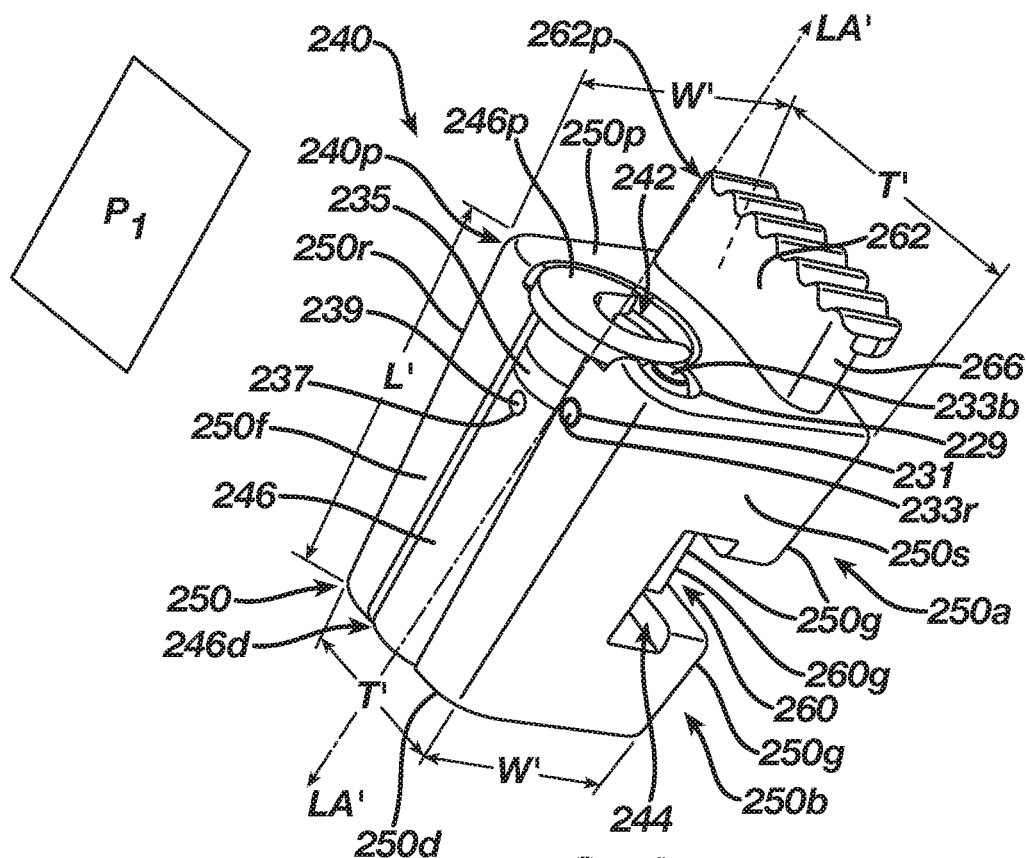
FIG. 9A is an isometric view of the carriage of FIG. 3.
Figure 9B:
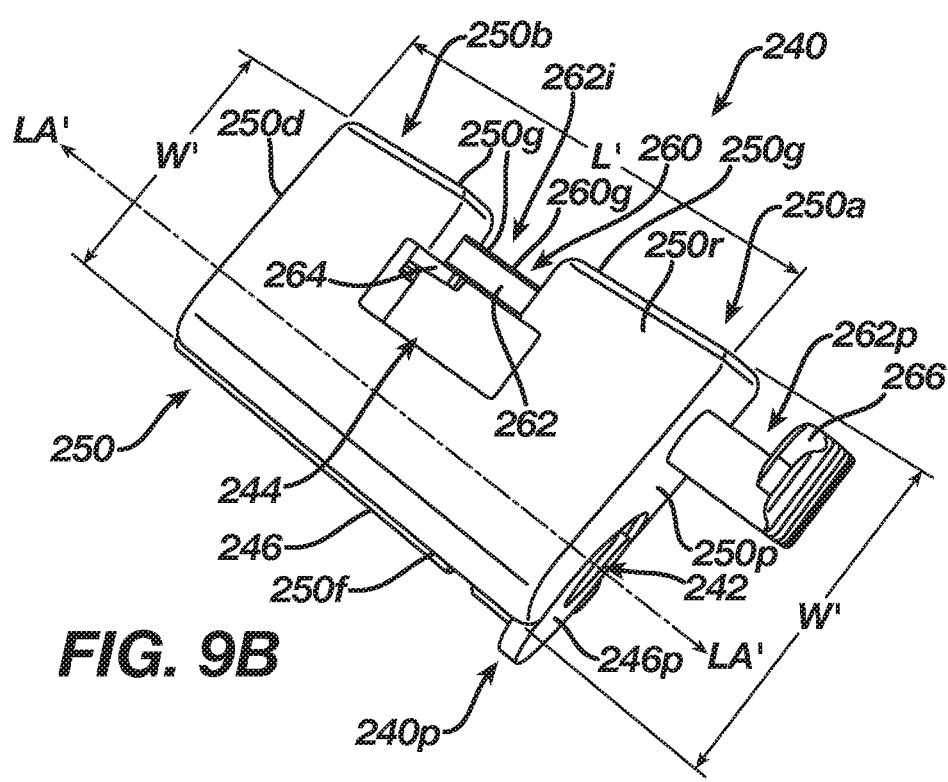
FIG. 9B is a side perspective view of the carriage of FIG. 9A.
Figure 9C:
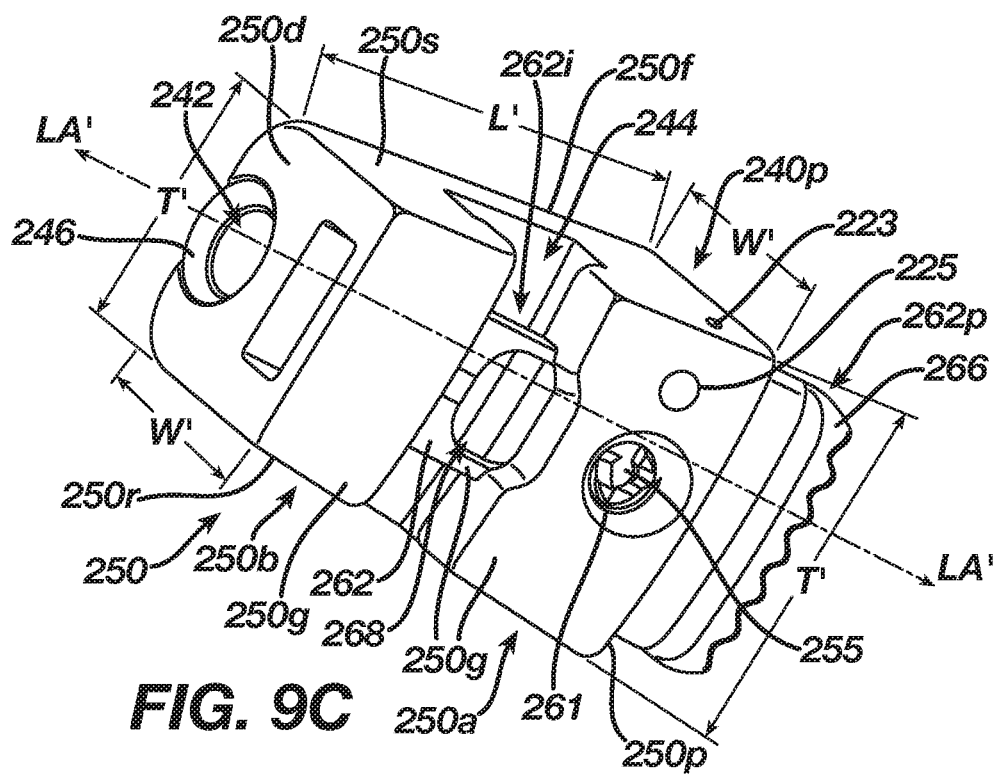
FIG. 9C is a back perspective view of the carriage of FIG. 9B.

While more detail about two configurations illustrated in FIGS. 2 and 3 are provided below, one of the primary differences between the two configurations is the construction of the carriages 140, 240, and in particular how the carriages are configured to receive a bullet. The carriage 140 of FIG. 2 includes a bullet-receiving opening 142 that is generally configured to receive a bullet 170 inserted from the top, as shown through a proximal end 140*p* of the carriage 140, and inserted towards a distal end 140*d* of the carriage 140. The carriage 240 of FIG. 3 includes a bullet-receiving opening 242 that is generally configured to receive a bullet inserted from a side of the carriage, as shown a front-facing or first facial surface 250*f* (which is visible better in FIG. 9A), such that the bullet passes from an outside environment, across a plane $P_1$ extending substantially through the first facial surface 250*f*, and into the bullet-receiving opening 242.

Figure 1A:
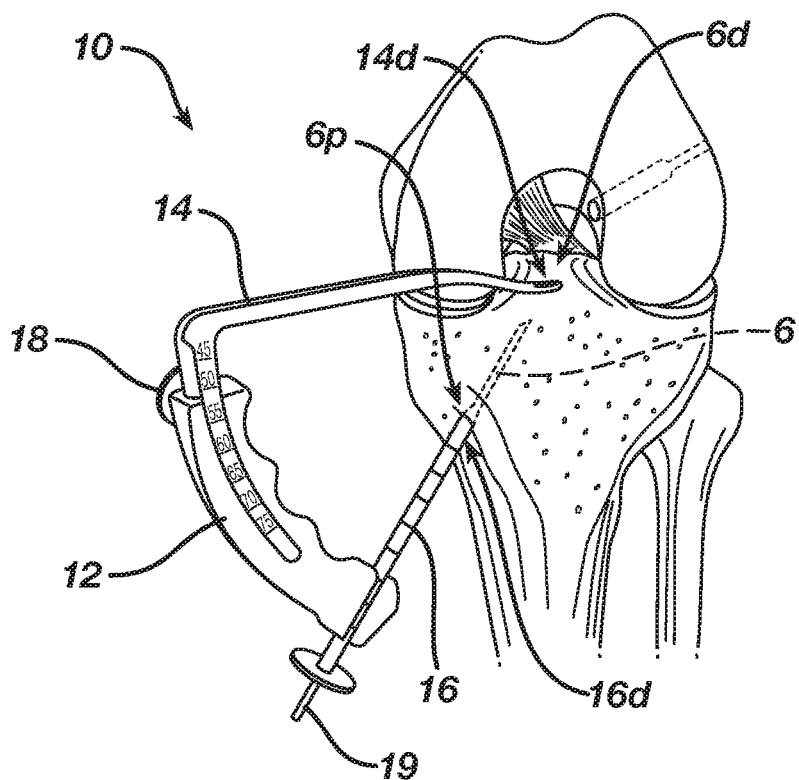
FIG. 1A is a schematic front perspective view of one embodiment of a modular guide that exists in the prior art, the guide having a bullet associated therewith and the guide and bullet being used in conjunction with a drilling instrument to form a tibial tunnel in a knee.
Figure 1B:
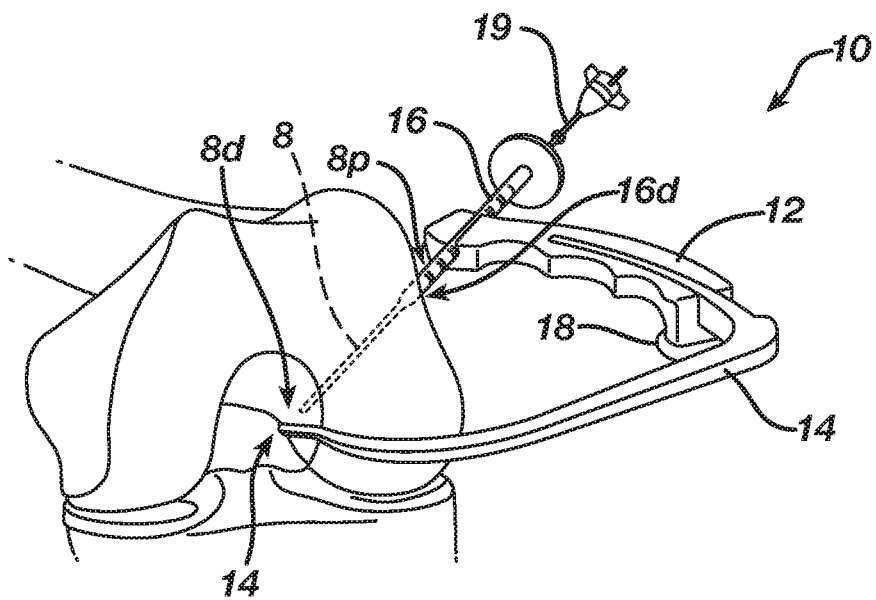
FIG. 1B is a schematic isometric view of the modular guide and bullet of FIG. 1A, now being used in conjunction with the drilling instrument to form a femoral tunnel in the knee.

The configurations illustrated in FIGS. 2 and 3, as well as the variations thereof described herein or otherwise derivable therefrom, provide a number of benefits in comparison to existing guides, such as the guide 10 illustrated in FIGS. 1A and 1B. The interaction between the carriage and the guide arm creates a secure locked position that establishes the trajectory of the bone tunnel and that is not likely to be disengaged unintentionally during use. Thus, the likelihood of the bone tunnel being drilled inaccurately through the bone tunnel whether through divergence or otherwise is decreased. The configuration of the guide is also such that it can be easily operated by a surgeon without the surgeon needing to switch hands or replace components of the guide to perform various tasks during a surgical procedure. In fact, unlike previous guides, the guides provided for herein are universal in that the same guides can be used easily in a surgeon's right-hand or left-hand on either knee of a patient to form both the tibial and femoral tunnels without having to change parts or shift grips to easily operate the guide. Still further, the disclosed designs allow the angle or trajectory of the bone tunnel to be defined by a portion, e.g., the carriage, that is separate from the portion held be a user during typical operation of the device. These benefits of the disclosed guides, as well as others, are evident from the descriptions below.

The present disclosure also provides for a drill pin depth gage that can be used in conjunction with the guides described herein or guides known in the prior art. Two exemplary embodiments of a drill pin depth gage 380, 480 are provided in FIGS. 21A and 23C-23F herein. The gages provided for herein or otherwise derivable therefrom improve the way by which a bone tunnel is drilled in bone by enabling a user to easily prevent a drill pin used to drill the tunnel from traveling too far. A drill pin that extends distally too far past the bone tunnel can cause damage to surrounding tissue and the like, e.g., femoral articular cartilage and neurovascular structures. More particularly, the guide enables the user to accurately set the location of the drill pin with respect to a drill chuck so that the drill pin cannot travel substantially beyond the intended distal end of the bone tunnel, and thus prevents unintended contact with surrounding tissue.

Turning back to the embodiments of the surgical guides 110, 210, each generally includes a guide arm 120, 220 with a carriage 140, 240 disposed on a portion thereof. The arm 120, 220 can be considered to have a first portion 122, 222 and a second portion 124, 224 with an angle α, α' that can be approximately 110 degrees or less extending between the two portions. Alternatively, the portions can be described as a first arm and a second arm, respectively. The first arm or portion 122, 222 can operate in conjunction with the carriage 140, 240 to define an angle at which the bone tunnel is to be drilled into bone, sometimes referred to herein as the trajectory of the bone tunnel, while a tip 126, 226 disposed at a distal or second end 124b, 224b of the second arm 124, 224 can define a location of a distal end of the bone tunnel to be drilled. As shown, the carriage 140, 240 is disposed on the first arm 122, 222 and can translate along a length thereof, and it can selectively lock along the arm to set the bone tunnel trajectory. The carriage can have an opening 142, 242 to receive a bullet 170, 270, which can work in conjunction with the first arm 122, 222 and the carriage 140, 240 to more easily establish the trajectory for the drilling component, e.g., a drill pin or reamer, to enter the bone. A distal end 170d, 270d of the bullet 170, 270 can also be disposed adjacent to a proximal end of the intended bone tunnel to define the entry location for the drilling component.

The two components of the guide 110, 210—the guide arm 120, 220 and the carriage 140, 240—as well as the bullet 170, 270, are described in further detail below with respect to at least one of the two embodiments illustrated in FIGS. 2 and 3. The bullet can be considered to be part of the guide, or it can be considered as a separate component, separate from the guide. Generally, the guide arm, carriage, and bullet can be considered to be core components of a surgical or modular system. Thus, disclosures provided for herein that allow for a universal system in which core components do not have to be replaced or reconfigured for use in the right or left hand allows for components like the guide arm, carriage, and bullet to be used without replacing or reconfiguring them. A person having ordinary skill in the art will recognize that many of the teachings provided for one embodiment of the guides 110, 210 are equally applicable to both embodiments, as well as other embodiments provided for herein or otherwise derivable from the present disclosure.

Further, the disclosures herein discuss various features that can assist with guiding and locking the guide system. Generally, a guide portion of the system can be any component that defines a location and a trajectory of a bore to be drilled in the bone and is configured to be gripped by a user when the system in use. Guide portions include, but are not limited to, the guide arm (e.g., guide arms 120, 220, among others) of the system. Generally, a locking portion can be any component configured to work in conjunction with the guide portion to define the location and the trajectory of the bore to be drilled in the bone and is configured to lock the guide system to finalize or otherwise define the trajectory of the bore. Locking portions include, but are not limited to, the carriage (e.g., carriages 140, 240) and/or bullets (e.g., bullets 170, 270). In some instances, the components can be both a guide portion and a locking portion. For example, sometimes a carriage can be both a guide portion and a locking portion.

Guide Arm

Figure 4A:
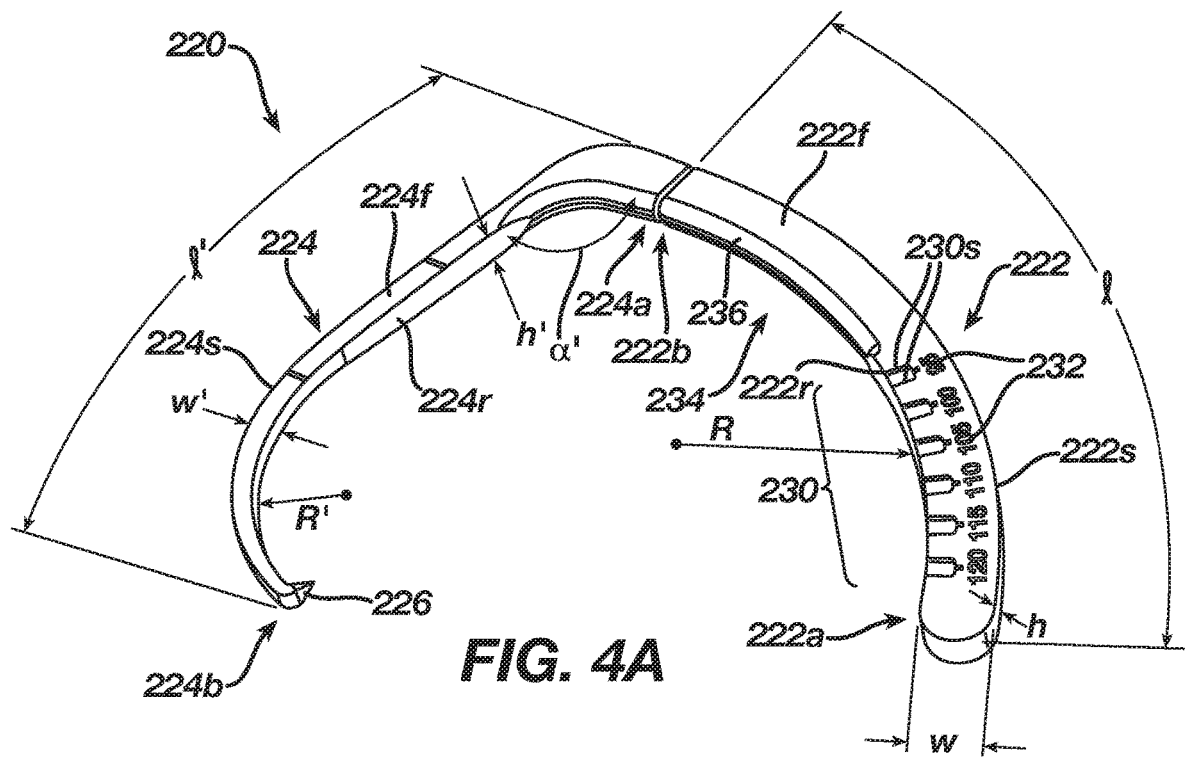
FIG. 4A is a back perspective view of a guide arm of the modular guide of FIG. 3.
Figure 4B:
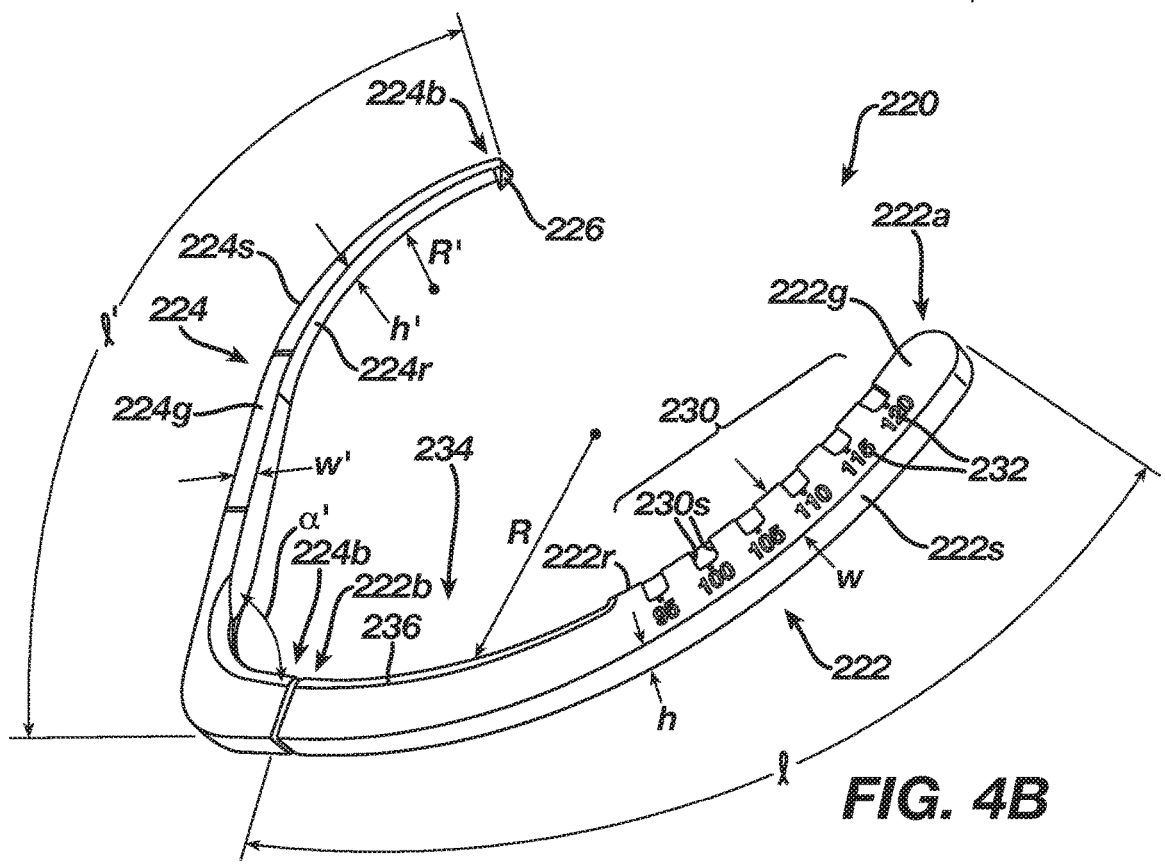
FIG. 4B is a front perspective view of the guide arm of FIG. 4A.

The guide arm 220 from FIG. 3 is illustrated in FIGS. 4A and 4B. A first portion (or arm) 222 is generally configured to engage with a carriage so the carriage can be translated along a portion of the first portion's length, while a second portion (or arm) 224 is configured to bend around to another side of a bone in use to serve as an indicator of where the distal end of the bone tunnel should be formed.

As shown, the first arm 222 is generally arcuate and has two facial surfaces 222f, 222g that are generally parallel to each other and two sidewalls 222r, 222s extending therebetween, which are also generally parallel to each other. The surfaces of the facial surfaces 222f, 222g and the sidewalls 222r, 222s can be substantially flat and can have a substantially consistent width w and height h across a length l of the first arm 222. In the illustrated embodiment the arcuate nature of the arm 222 is such that it maintains a radius of curvature R that is substantially the same across the entire length l of the arm, although in other embodiments only a portion of the arm 222 may be arcuate or the arm may have varying radii of curvature across its length. One end 222a of the first arm 222, which forms a terminal end of both the first arm 222 and the guide 210, has a curved configuration, while the second, opposed end 222b of the first arm 222 is configured to mate with the second arm 224. For example, the first arm 222 can have a male member formed at its end 222b that is configured to be received by a complementary female member formed at a first end 224a of the second arm 224.

A person having ordinary skill in the art will recognize that there are many other ways by which the first and second arms 222, 224 can be connected. For example, as shown in the FIG. 2 embodiment, the first and second arms 122, 124 are held together by a coupling device 128, such as a band or clamp, to maintain one arm at a set location with respect to the other. In some embodiments, the first and second guide arms 122, 222 and 124, 224 can be of a singular construction such that they are the same piece. More generally, as used herein, the term unitary construction encompasses embodiments that are of a singular construction as well as embodiments in which the first arm is coupled to the second arm in some manner to form a unitary arm. The unitary construction is such that the first and second arms are not moved with respect to each other to adjust an intended angle or trajectory of the bone tunnel to be drilled. Further, neither the first nor second arm are moved with respect to a component configured to be held by the user, such as a frame, to adjust an intended angle or trajectory of the bone tunnel to be drilled.

One or more engagement features can be formed on at least a portion of the first arm 222. In the embodiment illustrated in FIGS. 4A and 4B, the engagement feature is a plurality of slots 230 (e.g., six slots) formed at a location near the terminal end 222a of the arm 222, closer to the terminal end 222a than then second end 222b. Each slot serves as a location at which the carriage can be locked with respect to the arm 222 to achieve a particular angle for the trajectory of the bone tunnel. A person having skill in the art will recognize the significance of the numbers used to define the trajectories or angles identified on the first arm 222. The numbers are useful to the surgeon based on the reference point the surgeon is using to define the actual trajectory of the bone tunnel. Accordingly, just because a trajectory is set at a particular number on the first arm e.g., 75 degrees, does not mean that an angle formed between the bullet and the bone, the bullet and a particular portion of the second arm, or any other particular dimension is 75 degrees. A person having skill in the art using the guide 210 will understand the significance of the defined trajectory for his or her own particular purposes.

Figure 5:
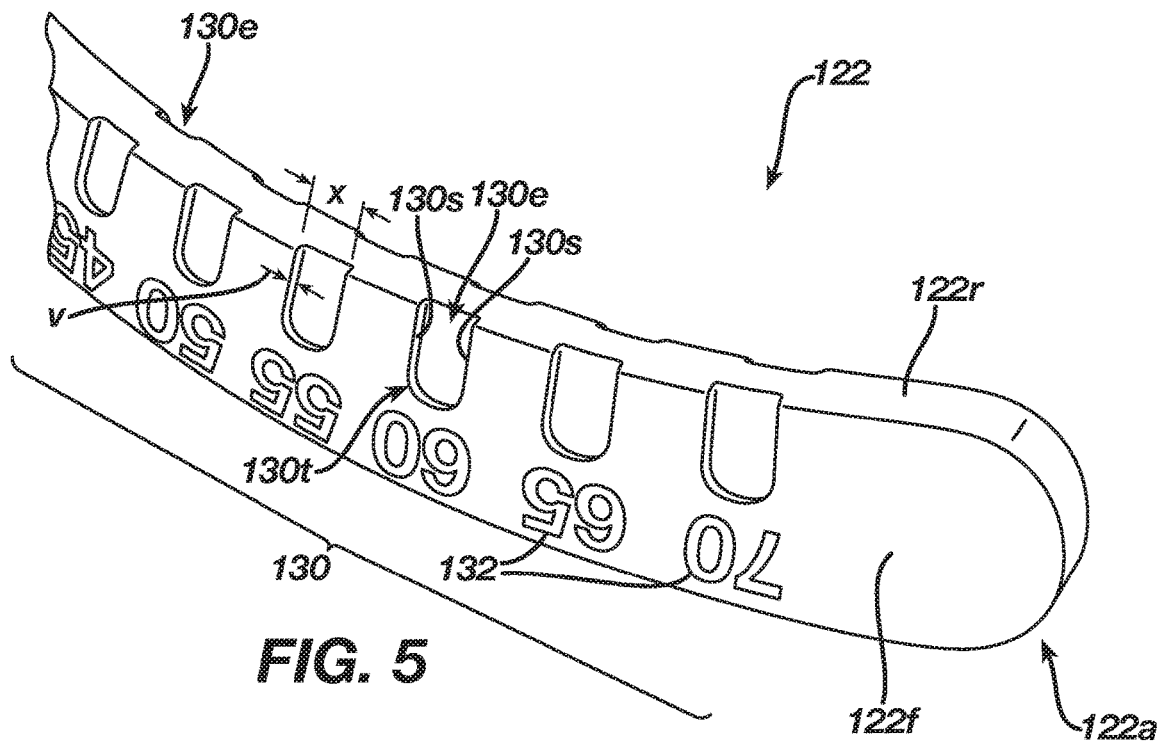
FIG. 5 is a detailed back perspective view of a second portion of a guide arm of the modular guide of FIG. 2.

As shown in FIGS. 4A and 4B, the slots 230 provided allow for angles between 95 degrees and 120 degrees, with each slot being spaced from respective slots such that the provided for angles are five degrees apart from each other. Slots 130 formed in the first arm 122 of the guide 110 of FIG. 5 allow for angles between 45 degrees and 70 degrees, again with each slot being spaced from respective slots such that the provided for angles are five degrees apart from each other. Similar to the guide 210, the first guide 110 can include the first and second arms 122 and 124. As shown in FIG. 5, the first arm 122 can include two facial surfaces 122f, 122g (122g is not visible) and two side surfaces 122r, 122s (122s is not visible), with the slots 130 being formed proximate to a terminal end 122a. While the illustrated embodiments show trajectory ranges between 95 degrees and 120 degrees and between 45 degrees and 70 degrees, a person skilled in the art will recognize a wide variety of trajectory options that are possible, with the range being anywhere from about 15 degrees to about 165 degrees, and with each slot having a degree difference therebetween approximately in the range of about 1 degree to about 25 degrees. In some embodiments, a single slot may be desirable so that a consistent trajectory is used for each procedure with that arm. Further, although in the illustrated embodiment the engagement feature(s) includes slots, other engagement features known to those skilled in the art can also be used in place of or in conjunction with slots without departing from the spirit of the present disclosure.

Indicia 132, 232 can be formed or otherwise indicated on the first arm 122, 222, adjacent to the slots 130, 230, so a user knows the angle associated with the respective slot. In alternative embodiments, indicia can be used in lieu of slots. The angles established by the device 110, 210 can depend on a variety of factors, including but not limited to the location of the slots 130, 230 on the first arm 122, 222, the radius of curvature R, R' of the portion of the first arm 122, 222 in which the slots 130, 230 are formed, and the configuration of the carriage with which the arm 120, 220 is used.

Figure 6:
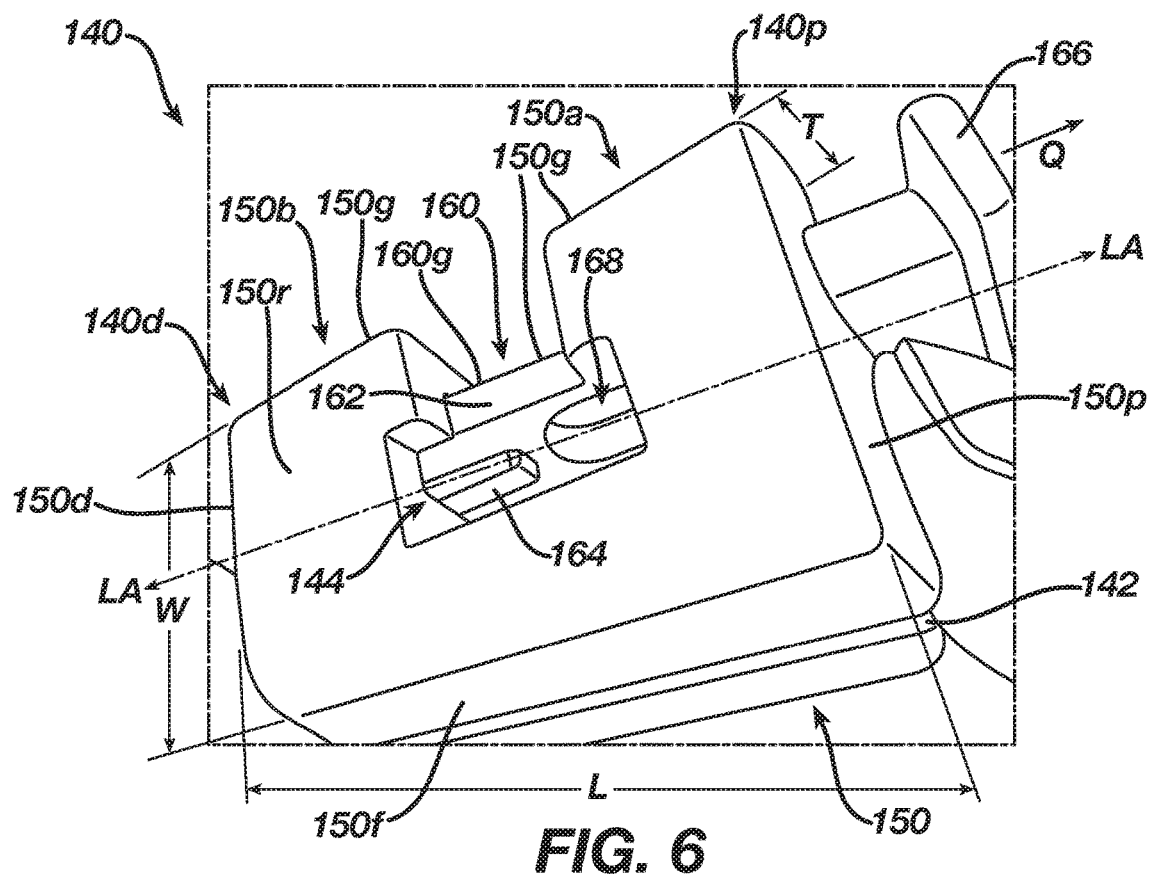
FIG. 6 is a side perspective view of a carriage of the modular guide of FIG. 2.

The slots 130, 230 themselves are indentations formed in the facial surfaces 122f, 222f and 122f, 122g of the arm 122, 222, and thus they serve as female mating elements. The slots 130, 230 can be configured in a variety of ways, but they generally have a configuration that is complementary to a male member of the carriage (a key 164, as shown in FIG. 6, for the arm 222) with which the female slots engage. In the illustrated embodiments, but labeled only in FIG. 5, each indentation is slightly tapered such that a height v of a sidewall 130s, 230s of each slot 130, 230 proximate to an entry opening 130e, 230e of the slot is slightly higher than the height v of the sidewall 130s, 230s proximate to a terminal end 130t, 230t of the slot. Such a configuration makes it easier for the male member of the carriage to lock into the desired female slot 130, 230 because the pocket at the entry opening 130e, 230e is deep enough to catch the male member while the pocket at the terminal end 130t, 230t is deep enough to maintain the male member therein until the male member is affirmatively removed from the slot. In fact, such a configuration helps to allow for a passive locking configuration in which the carriage can be locked at a desired trajectory along the first arm without a user actively engaging the male member of the carriage to lock into the slot.

As shown in FIGS. 4A and 4B, the slots 230, as well as the indicia 232 associated with the slots 230, can be formed in both facial surfaces 222f, 222g of the first arm 222. Even though the carriage is only designed to engage a slot on one side of the arm, providing slots 230 on both facial surfaces 222f, 222g creates a universal configuration that allows the same guide to be easily used by right-handed and left-handed users without making significant adjustments to the core components, e.g., nothing more than flipping the direction of the carriage for right and left-handed users. Such a configuration also makes it easier for a user to use the device on either the left knee or the right knee to form both the tibial and femoral tunnels, regardless of where the user is located with respect to the knee. A surgeon can thus perform a procedure with the same device from the same location in the operating room without moving to a different location in the room and without having to replace or adjust one or more of the core components of the guide, i.e., the guide arm, the carriage, and/or the bullet. In other embodiments, carriages can be configured to engage slots on both sides of the arm to provide an even more secure locked position, or alternatively, the arm can have slots formed in only one side of the arm, for instance to make manufacturing quicker and less expensive.

The first arm 222 can also include features to assist a user in gripping the device 210. The device 210 is generally configured in a manner that allows the first arm 222 to sit in a palm of a user's hand at a gripping location 234 further down the length of the arm 222 than the slots 230, away from the terminal end 222a, with a user's fingers wrapped around the arm 222 at this location as well. In the illustrated embodiment a chamfer 236 is formed in the arm 222 at the gripping location 234 to provide a comfortable grip for the user. The chamfer 236 can be provided on both sides of the arm 222 as shown, thus providing additional features that allow for the device 210 to be used universally, i.e., with either hand, in conjunction with a procedure performed on either knee to form both the tibial and femoral tunnels, regardless of where the user is located with respect to the knee, and without having to replace or reconfigure core components of the device. A person skilled in the art will recognize other features that can be incorporated into the arm to assist a user in gripping the device. By way of non-limiting example, in some embodiments finger grips or grooves can be formed at the gripping location 234 to provide a location at which the fingers of a user can be positioned when holding the device 210.

The second portion or arm 224 mates to the first arm 222 to form a unitary configuration, as described above. Further, the second arm 224 can be disposed at an angle α' with respect to the first arm 222, the angle being formed in a plane $P_2$ that extends substantially through the facial surfaces 222f, 224f of the first and second arms 222, 224. More particularly, the angle between the first and second arms 222, 224 can be approximately 110 degrees or less. A person skilled in the art will recognize that the angle α' for a guide arm used to form a tibial tunnel is typically different than the angle α' for a guide arm used to form a femoral tunnel. In some embodiments, the angle between the arms is in the range of about 60 degrees to about 110 degrees, and in one exemplary embodiment the angle is about 105 degrees for a femoral tunnel and about 90 degrees for a tibial tunnel. The angle formed between the first and second arms 222, 224 can assist in allowing access to a desired location in the body, such as the knee. More particularly, the angle allows a bullet to be associated with the guide arm 220 such that a distal end of the bullet can be disposed at a desired location for the proximal end of a bone tunnel and the distal end 224b of the second arm 224 can be disposed at a desired location for the distal end of the bone tunnel. The angle α' can also be different for guide arms used in other contexts outside of the tibia and femur.

The second arm 224 can have a variety of configurations. As shown, it has an arcuate configuration, particularly towards its distal end 224b, which allows the second arm 224 to be positioned at a location proximate to a desired location for the distal end of the bone tunnel. In the illustrated embodiment, the second arm 224 includes two facial surfaces 224f, 224g substantially parallel with respect to each other and two sidewalls 224r, 224s extending therebetween, which are also substantially parallel with respect to each other. As used herein, the term substantially parallel does not necessarily mean exactly parallel, at least because of various tapers that may exist across one or more of the surfaces being described as being involved in a substantially parallel configuration. For example, in some embodiments the first facial surface 224f may be tapered towards a central longitudinal axis of the housing 250 from the proximal end 250p to the distal end 250d so that a distal tip of a bullet disposed in the housing can be seated approximately within the plane $P_2$ that extends through the guide, as described in greater detail below. A pointed distal tip 226 can be disposed at the terminal or second end 224b of the second arm 224, and can be used to define a location of a distal end of the bone tunnel to be drilled. It can also be used to indicate to a user passing a drill pin or other cutting device from the first arm 222 and to the terminal end 224b of the second arm that the terminal end 224b has been reached so that the cutting device is not further distally advanced. In some embodiments the tip 226 can be blunter to help stop a distally advancing cutting or drilling device. In still other embodiments the distal tip of the second arm can be a partial circle, e.g., a C-shape, or a full circle that defines an opening through which the drill pin is received.

A first end 224a of the second arm 224 can have a configuration that is similar to the second end 222b of the first arm 222 to make coupling the first arm to the second arm easy. Thus, the transition from one arm to the next is smooth. As shown, a gripping feature such as the chamfer 236 can extend onto a portion of the second arm 224 such that the first end 224a of the second arm 224 is part of the gripping location 234. A remaining portion of the second arm 224, however, can be thinner along its length so that the arm is less obtrusive when disposed in the body. As shown, both a height h' and a width w' of the second arm tapers along a length l' of the second arm 224 such that the height h' and width w' at the distal end 224b are less than the height h' and width w' at the first end 224a. In some embodiments the length l' of the second arm 224 can be similar to the length l of the first arm 222, although in other embodiments one of the arms can be longer than the other.

A person having ordinary skill in the art will recognize a variety of other configurations that can be used to form the guide arm without departing from the spirit of the present disclosure. Bearing that in mind, in some embodiments, such as the guide arms 120, 220 illustrated herein, a length l of the first arm 122, 222, measured from opposed tips as illustrated in view of the arcuate nature of the arm, can be approximately in the range of about 10 centimeters to about 15 centimeters, a width w of the first arm 122, 222 can be approximately in the range of about 10 millimeters to about 30 millimeters, and a height h of the first arm 122, 222 can be approximately in the range of about 5 millimeters to about 10 millimeters, with a radius of curvature R being approximately in the range of about 90 millimeters to about 120 millimeters. In one exemplary embodiment the first arm 122, 222 has a length l of about 12 centimeters, a width w of about 13 millimeters, a height h of about 6 millimeters, and a radius of curvature R of about 108 millimeters. Each slot can have a length y (FIG. 5) approximately in the range of about 3 millimeters to about 10 millimeters, a width x (FIG. 5) approximately in the range of about 3 millimeters to about 10 millimeters, and a tapering height v (FIG. 5) approximately in the range of about 3 millimeters to about 8 millimeters at its greatest and smallest heights. In one exemplary embodiment, each slot has a length y of about 5 millimeters, a width x of about 4 millimeters, and a height v proximate to the entry opening 130e, 230e of about 6 millimeters and a height v proximate to the terminal end 130t, 230t of about 5 millimeters.

Likewise, in some embodiments, such as the guide arms 120, 220 illustrated herein, a length l' of the second arm 124, 224, measured from opposed tips as illustrated in view of the arcuate nature of the arm, can be approximately in the range of about 10 centimeters to about 15 centimeters, a width w' of the second arm 124, 224 can be approximately in the range of about 3 millimeters to about 15 millimeters, with the width w' decreasing along its length from the first end 124a, 224a to the second end 124b, 224b, a height h' of the second arm 124, 224 can be approximately in the range of about 2 millimeters to about 8 millimeters, again with the height h' decreasing along its length from the first end 124a, 224a to the second end 124b, 224b, and a radius of curvature R' proximate to the second end 124b, 224b approximately in the range of about 0 millimeters to about 46 millimeters. In one exemplary embodiment the second arm 124, 224 has a length l' of about 13 centimeters, a width w' of about 11 millimeters at the first end 124a, 224a and of about 4 millimeters at the second end 124b, 224b, a height h' of about 6 millimeters at the first end 124a, 224a and of about 4 millimeters at the second end 124b, 224b, and a radius of curvature R' proximate to the second end 124b, 224b of about 46 millimeters. Further, first and second arms 122, 222 and 124, 224 of the guide arm 120, 220 can be made from a variety of materials, including but not limited to surgical grade metals such as stainless steel and titanium, or various polymers. In some embodiments the arms can be made from the same material, while in other embodiments they can be made from different materials.

Carriage

FIG. 6 illustrates one exemplary embodiment of a carriage 140, the carriage 140 being of the nature illustrated in FIG. 2, i.e., it is configured to receive a bullet in the bullet-receiving opening 142 from the proximal end 140p thereof. Notably, the carriage 140 is a separate component of the device 110 from the portion of the device generally held by a user during use, i.e., the guide arm 120, which makes the device 110 easier to use and more accurate than devices that include the component that defines the trajectory of the bone tunnel as part of the portion generally held by a user during use, such as the device 10 illustrated in FIGS. 1A and 1B. The carriage 140 generally includes a housing 150, a bullet-receiving opening or channel 142, and a guide-receiving opening 144 for being disposed on the guide arm, e.g., guide arm 120. The housing 150 can have many different shapes and sizes, which can depend, at least in part, on the configuration of the device components with which it is being used, the anatomy of the patient, and the type of procedure with which it is being used. In the illustrated embodiment, the housing 150 can generally be described as having the shape of a trapezoidal prism that includes a proximal end 150p, a distal end 150d, two opposed facial surfaces 150f, 150g extending between the proximal and distal ends 150p, 150d, and two opposed side surfaces 150r, 150s extending between the two facial surfaces 150f, 150g and the proximal and distal ends 150p, 150d. Each of these surfaces need not be continuous, as discussed in greater detail below. By way of non-limiting example, the second facial surface 150g in the illustrated embodiment includes an upper portion 150a and a lower portion 150b that are not continuous, but together with a guide engaging mechanism 160, these two portions 150a, 150b form a wall of the guide-receiving opening 144 that extends from one side surface 150r to the other side surface 150s. As shown, an outer surface 160g of the guide engaging mechanism 160 extending between the upper and lower portions 150a, 150b and facing outward is not flush with outer surfaces of the upper and lower portions 150a, 150b, although it could be in other configurations.

Figure 7:
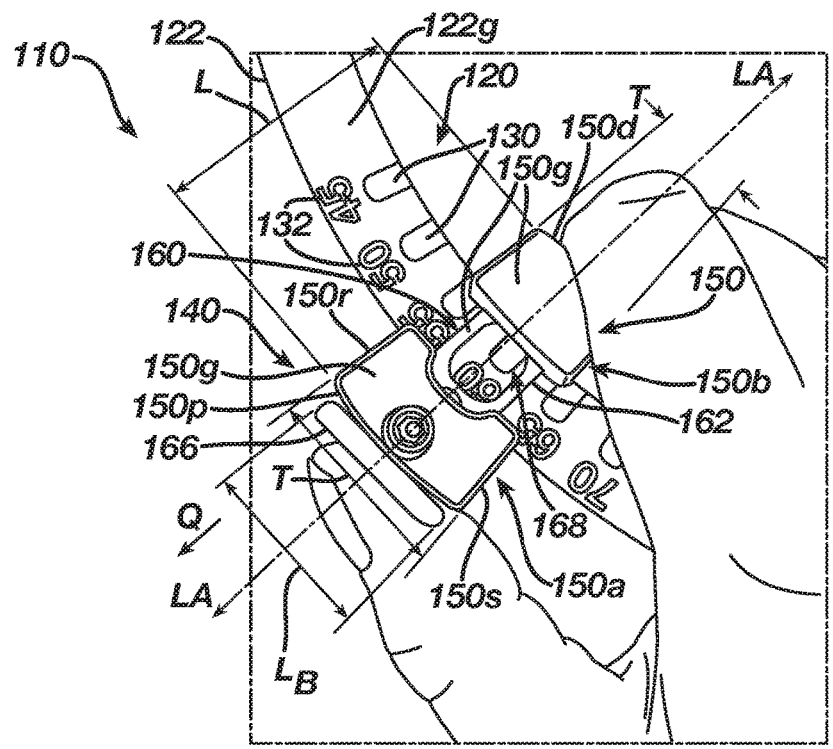
FIG. 7 is a back view of the carriage of FIG. 6 disposed on the second portion of the guide arm of FIG. 5.
Figure 8:
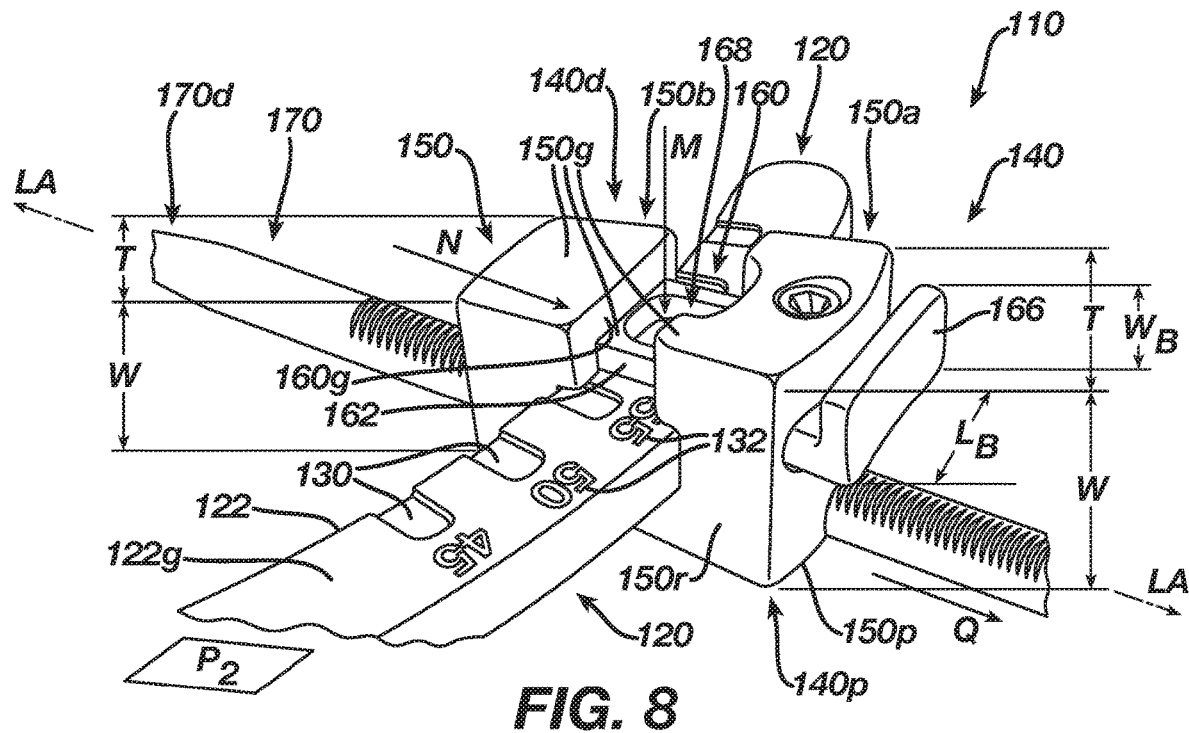
FIG. 8 is a back perspective view of the bullet of FIG. 2 disposed in the second portion of the guide arm of FIG. 7.

As shown, a length L of the housing 150 is defined by the distance between the proximal and distal ends 150p, 150d, which is also a length of the first and second facial surfaces 150f, 150g and a length of the first and second sidewalls 150r, 150s. In the illustrated embodiment, the lengths of the facial surfaces 150f, 150g and the sidewalls 150r, 150s are substantially equal. A thickness T of the housing 150 is defined by the distance between the first and second sidewalls 150r, 150s, which is also a width of the first and second facial surfaces 150f, 150g and a length of the proximal and distal ends 150p, 150d. As shown in FIG. 7, the thickness T of the housing 150 at the proximal end 150p is greater than the thickness T at the distal end 150d. A width W of the housing 150 is defined by the distance between the first and second facial surfaces 150f, 150g, which is also a width of the side surfaces 150r, 150s and a width of the proximal and distal ends 150p, 150d. As shown in FIG. 8, the width W of the housing at the proximal end 150p is greater than the width W at the distal end 150d. Generally, the length L of the housing 150 is larger than the thickness T and width W of the housing 150, although it does not necessarily have to be. A longer housing can help to more securely seat the bullet though.

The bullet-receiving opening or channel 142 can be formed in the first facial surface 150f. As shown, the bullet-receiving opening 142 extends longitudinally from and through the proximal end 150p to and through the distal end 150d and has a substantially cylindrical shape that is complementary in shape to the bullet 170 it is configured to receive. Likewise, a diameter of the opening 142 is such that it is sized to receive a bullet therein. In the illustrated embodiment, a diameter of the bullet-receiving opening 142 is less than half the size of the width W of the housing. Further, the bullet-receiving opening 142, and the first facial surface 150f in which it is formed, can be tapered from the proximal end 150p to the distal end 150d to help align a bullet disposed therein with the desired location for the proximal end of the bone tunnel. That is, because the carriage 140 extends away from the plane $P_2$ extending substantially through the facial surfaces 122f and 124f of the first and second arms 122, 124, a slight taper in the first facial surface 122f and/or the bullet-receiving opening 142 can help direct a distal end of a bullet to be in the plane $P_2$ at the surgical site. As a result, the distal end 170d of the bullet 170 can be properly aligned with the distal tip 126 to allow for the bone tunnel to be properly aligned between the proximal and distal ends of the bone tunnel. A degree of the taper can be approximately in the range of about 1 degree to about 8 degrees with respect to the plane $P_2$, and in some embodiments the degree of taper is about 3 degrees with respect to the plane $P_2$.

The guide-receiving opening 144 can extend substantially transverse to the bullet-receiving opening 142, extending through the housing 150 from and through the first side surface 150r to and through the second side surface 150s, with the opening 144 being defined by an inner wall of the proximal end 150p, an inner wall of the distal end 150d, an inner wall of the first facial surface 150f, and an inner wall of the second facial surface 150g, e.g., predominately by an inner wall of the guide engaging mechanism 160. As shown, the guide-receiving opening 144 and the bullet receiving opening extend in different planes. A size and shape of the guide-receiving opening 144 can be complementary to the size and shape of the first arm 122 of the guide arm 120 such that the first arm 122 can extend through the guide-receiving opening 144 and the carriage 140 can be securely locked at one or more locations along a length of the first arm. In the illustrated embodiment, a length L of the carriage 140 can extend substantially transverse to a length l of the first arm 122. As used herein, the term substantially transverse does not necessarily mean exactly transverse, at least because of the arcuate configuration of the first arm 122. A person skill in the art will understand that such a description is generally intended to address the fact that, as shown, the length L of the carriage 140 is not generally disposed in the same direction as the length of the first arm 122.

As indicated above, the second facial surface 150g can be partially formed by a surgical guide engaging mechanism 160. In the illustrated embodiment the surgical guide engaging mechanism 160 includes a bar 162 that is opposed substantially parallel to the first facial surface 150f, although not necessarily exactly parallel in embodiments in which the first facial surface 150 has a slight taper with respect to the plane $P_2$ as described above. The bar 162 can include a male member formed thereon, as shown a selectively deployable key 164, having a shape and size that is complementary to a shape and size of the female member formed on the arm guide 120, as shown in FIGS. 7 and 8, the plurality of slots 130.

The surgical guide engaging mechanism 160 can serve as a passive locking engagement mechanism. In conjunction with the same, a spring-loaded button 166 can be formed at a proximal end 160p of the guide engaging mechanism 160. The button 166 can be configured to move the key 164 along a longitudinal axis LA of the housing such that when the button 166 is depressed towards the distal end 140d of the carriage 140, as shown in FIG. 7, the carriage 140 can freely translate along the guide arm 120, including over and past the slots 130 formed in the first arm 122. However, when the button 166 is not depressed, as shown in FIG. 8, the carriage 140 can only slide along the guide arm 120 until the key 164 is biased back into one of the slots 130, i.e., the key 164 passively engages a slot 130.

As the key 164 becomes properly seated in a slot 130 to place the carriage 140 in a locked position, two forces are applied to the guide arm. As illustrated in FIG. 8, a first force in a direction M, which is approximately perpendicular to the second facial surface 122g of the first arm 120, causes the carriage 140 to push down against the guide arm 120, and a second force in a direction N, which is approximately perpendicular to the direction M and substantially parallel to the second facial surface 122g, causes the carriage 140 to push the guide arm 120 back. As a result, the carriage 140 is firmly locked into place with respect to the guide arm 120, and in turn reduces the risk of drill pin divergence without having to rely heavily on spring forces or tight tolerances, which can wear away over time. When the carriage 140 is in the locked position, the carriage 140 cannot advance along the length of the first arm 122, and it is also restricted from traveling along the longitudinal axis LA of the housing 150.

The button 166 can have a variety of shapes and sizes, but generally it can be configured so that it can be pressed by a thumb of a user. In the illustrated embodiment, a length $L_B$ of the button 166 is similar to the width W of the housing 150, and a width $W_B$ of the button 166 is approximately half the width W of the housing 150. Springs can be disposed in the housing 150 to bias the button 166, and thus the key 164, in a desired direction. In the illustrated embodiment, two springs are disposed along the length of the surgical guide engaging mechanism 160 and bias the button 166, and thus they key 164, in a direction Q, proximally away from the proximal end 140p of the carriage 140. The surgical guide engaging mechanism 160 can also include an opening 168 formed in the bar 162. The opening 168 can be configured so that the indicia 132 formed near the slots 130 can be easily read when the carriage 140 is disposed on the first arm 122, as shown in FIG. 7. In some embodiments, the opening 168 can allow a user see when the key 164 is about to or is engaging one of the slots 130.

The carriage 140 not only locks a location of the carriage 140 with respect to the guide arm 120, but it can also lock a location of a bullet disposed therein. More specifically, in the illustrated embodiment, the bullet 170 disposed in the bullet-receiving opening 142 is locked with respect to the length l of the first arm 122 and the height h of the first arm such that the bullet 170 cannot travel in these directions. The bullet 170 can travel along the length l of the first arm 122, however, when the carriage is operated to translate along the arm 122, as described above. Further, the carriage 140 can be configured to allow the bullet 170 to travel proximally and distally along the longitudinal axis LA, regardless of whether the carriage is in a translating or locked configuration. This allows the distal tip 170d of the bullet 170 to be positioned adjacent or proximate to the bone in which the bone tunnel is to be formed. This location can define the proximal end of the bone tunnel, and can also be used to help to measure bone stock, i.e., the thickness of the bone to be drilled, which in turn becomes the length of the bone tunnel, as described in greater detail below.

Side-Loading Carriage

A second embodiment of a carriage 240 is illustrated in FIGS. 9A-11. Similar to the carriage 140, the carriage 240 is a separate component of the device 210 from the portion of the device generally held by a user during use, i.e., the guide arm 220, which makes the device 210 easier to use and more accurate than devices that include the component that defines the trajectory of the bone tunnel as part of the portion generally held by a user during use, such as the device 10 illustrated in FIGS. 1A and 1B. The carriage 240 includes a housing 250 that can have many different shapes and sizes, which can depend, at least in part, on the configuration of the device components with which it is being used, the anatomy of the patient, and the type of procedure with which it is being used. Similar to the housing 150 of the carriage 140, the housing 250 has the shape of a trapezoidal prism that includes a proximal end 250p, a distal end 250d, two opposed facial surfaces 250f, 250g extending between the proximal and distal ends 250p, 250d, and two opposed side surfaces 250r, 250s extending between the two facial surfaces 250f, 250g and the proximal and distal ends 250p, 250d. Again, similar to the housing 150, each of the identified surfaces need not be continuous, e.g., the second facial surface 250g can include an upper portion 250a and a lower portion 250b that are not continuous, and a portion of a guide engaging mechanism 260, as shown an outer surface 260g, can extend between the two portions 250a, 250b to form a wall of a guide-receiving opening 244 that extends through the housing 250 from one side surface 250r to the other side surface 250s. A length L', a width W', and a thickness T' of the housing 250 can be defined by the same distances described above with respect to the housing 150, and as illustrated in FIGS. 9A-9C and 10. Typically the length L' is greater than the width W' and the thickness T'.

The carriage 240 also includes a bullet-receiving opening 242 and a guide-receiving opening 244. More particularly, the bullet-receiving opening 242 is formed within a rotatable receiver 246, which is rotatably disposed within the housing 250. An opening 241 can be formed in the first facial surface 250f to receive the rotatable receiver 246. As shown, the opening 241 can include a main receiving portion 241m and a track portion 241t formed in the proximal end 250p of the housing 250. The track portion 241t can have a diameter that is bigger than the main receiving portion 241m so that a proximal end 246p of the rotatable receiver 246 can sit within the track portion 241t and rotate with respect to the same.

In use, the rotatable receiver 246 rotates with respect to the housing 250 between a first position, also referred to as a receiving position, in which it is open to the outside environment so it can receive a bullet therein, and a second position, also referred to as a locking position, which is illustrated in FIGS. 9A-9C and 10, in which a bullet received by the rotatable receiver 246 is disposed in its locked position such that the bullet is locked in at least two planes with respect to the carriage 240. More particularly, the bullet in the locked position cannot translate between the first and second facial surfaces 250f, 250g or between the first and second side surfaces 250r, 250s. The rotatable receiver 246 also includes an intermediate position disposed between the receiving and locking positions, in which a bullet is disposed in the rotatable receiver 246 and is also unable to translate between the first and second facial surfaces 250f, 250g or between the first and second side surfaces 250r, 250s. However, as described in further detail below, in the locked position the bullet can only translate distally, towards distal end 250d, and not towards the proximal end 250d, while in the intermediate position the bullet can freely translate both distally and proximally.

While the rotatable receiver 246 can have a variety of shapes and sizes, depending, at least in part, on the configurations of the housing, bullet, and other related components and the type of procedure in which the carriage is being used, in the illustrated embodiment the rotatable receiver 246 has a generally cylindrical shape that is complementary in shape to the portions of the housing 250 in which it is disposed, i.e., the opening 241. Accordingly a main body 246m of the rotatable receiver can be shaped such that it can sit within the main receiving portion 241m of the opening 241 and can rotate within the opening. A proximal end 246p of the rotatable receiver 246 can include a cylindrical guide that is configured to be received in the track portion 241t of the opening 241. As shown, the proximal end 246p can have a diameter that is larger than a diameter of the main body 246m because in the illustrated embodiment a diameter of the track portion 241t is larger than a diameter of the main receiving portion 241m. Further, as shown, the proximal end 246p can include opposed indents 246i. The indents 246i can allow the rotatable receiver 246 to receive a portion of a ramp 233 used to help lock a location of the rotatable receiver 246 with respect to the housing 250, as described in greater detail below. Additionally, a diameter of the main body 246m can be tapered such that a diameter of the main body 246m adjacent to the proximal end 246p is larger than a diameter of the main body 246m at a distal end 246d of the rotatable receiver 246. This taper can be complementary to a taper formed in the main receiving portion 241m and/or the housing 250 itself, and can be configured to help align a bullet disposed in the bullet-receiving opening 242 with a desired proximal end of the bone tunnel to be formed, similar to the taper discussed above with respect to the carriage 140 of FIGS. 6-8. The degree of the taper with respect to the plane $P_1'$ (not shown) that extends substantially through the facial surfaces 222f, 224f when the carriage is disposed on the first arm 222 can likewise be similar.

The rotatable receiver can include features to help secure a bullet within the bullet-receiving opening 242. One such feature can be a protrusion, as shown a pin 239, that extends into the channel 242 at a deepest, central part of the channel, and can be complementary to a slot or groove formed in a bullet such that pin 239 can sit within the slot or groove of the bullet to help maintain a location of the bullet with respect to the rotatable receiver 246. When a bullet is secured by the pin 239, for instance by rotating the bullet within the channel 242 as described in greater detail below, incidental force applied to the bullet will not cause the bullet to rotate around the channel 242. In some embodiments, the materials of the pin and the bullet can be such that an audible sound is emitted once the pin 239 is disposed within the slot, thereby informing the user that the bullet is secured with respect to the rotatable receiver 246. The pin 239 can be disposed within a bore 237 formed in a wall of the rotatable receiver 246, or it can be associated with the rotatable receiver 246 using a variety of different techniques known to those skilled in the art. In the illustrated embodiment the pin 239 is disposed at a location in the proximal half of the rotatable receiver 246, although the pin 239 can be disposed anywhere along the length of rotatable receiver 246 without departing from the spirit of the present disclosure.

The rotatable receiver 246 can also include features to help hold the receiver 246 in a locking position and/or to help remove the rotatable receiver 246 from the locking position. One such feature is a groove or track 235 formed in an outer surface of the rotatable receiver 246. As shown, the track 235 extends around the outer surface from one end of the channel 242 to the other end of the channel 242, the track 235 being opposed to the channel 242. The track 235 is disposed in a location that allows it to work in conjunction with one or more ramps 233 provided for in the housing 250 to hold the rotatable receiver 246 in the locking position. As shown, the track 235 is in the proximal half of the rotatable receiver 246 and is disposed proximal of the pin 239.

The ramp used in conjunction with the features of the rotatable receiver 246, e.g., the indents 246i, to hold the receiver 246 in a locking position and/or to help remove the receiver 246 from the locking position can have a variety of configurations. As shown, the ramp 233 of the carriage is formed by the combination of a rod 233r and a button 233b. More particularly, the rod 233r can extend through a complementary opening 231 formed in the housing 250, adjacent to the opening 241, and the button 233b can extend through a different complementary opening 229 formed in the housing 250, adjacent to the opening 231 and having a longitudinal axis that extends therethrough that is substantially perpendicular to a longitudinal axis extending through the opening 231. The rod 233r sits within a channel 233c formed in the button 233b to loosely hold the button 233b within the structure of the housing 250. The opening 231 is formed so that it is aligned with the track 235 when the rotatable receiver is properly disposed within the housing 250. A portion of a sidewall of the rod 233r extends through the opening 231 and into the opening 241, and thus can extend into the track 235. Such a configuration aids the rotatable receiver 246 in being able to rotate with respect to the housing 250. A spring 233s can be disposed in the opening 229, between a base of the opening 229 and the button 233b, to allow the button 233b to float within the opening 229, at least due in part to the loose hold the rod 233r has on the button 233b. A force supplied by the spring 233s to the button 233b can be large enough to hold the rotatable receiver 246 in a locked position but small enough to allow the rotatable receiver to be unlocked by rotating it in the opposite manner without using any sort of release button to disengage the button 233b from the indent 246i.

Figure 10:
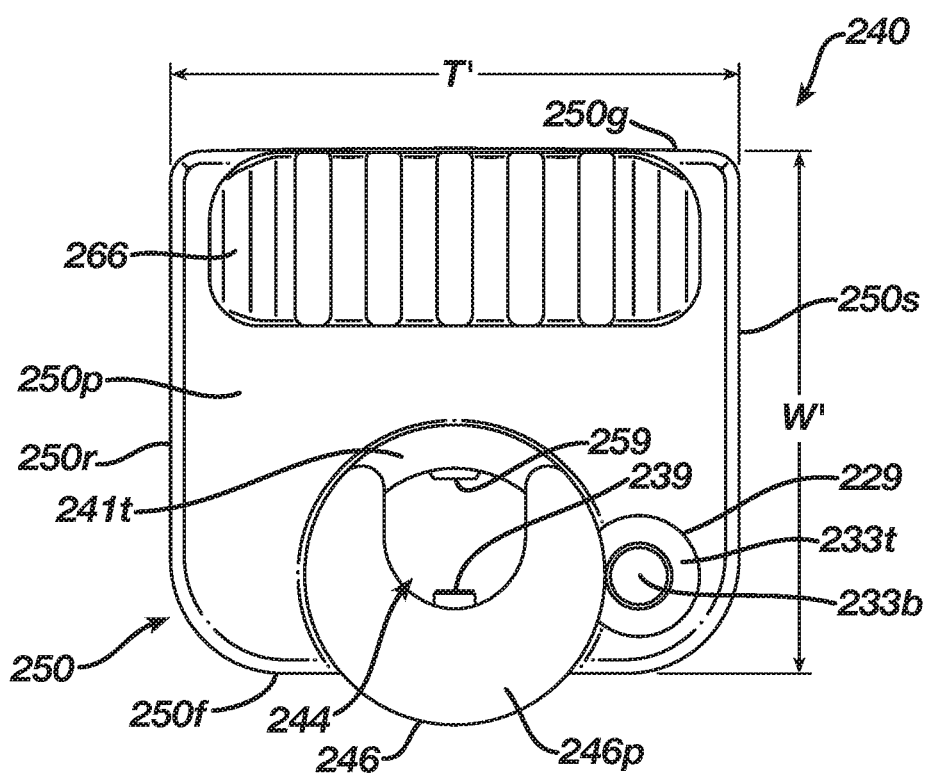
FIG. 10 is a top view of the carriage of FIG. 9A.

The opening 229 is formed so that a proximal end of the button 233b can engage one of the indents 246i formed in the rotatable receiver 246 to secure the locking position of the rotatable receiver 246 with respect to the housing 250. As shown, the button 233b includes a tapered ramp 233t at its proximal end that is complementary to the indents 246i. When the ramp 233 engages the surface of the rotatable receiver 246 that forms the indent 246i, the rotatable receiver 246 can be secured in the locking position, as shown in FIG. 10. As shown in the illustrated embodiment, one of the indents 246i is a bit larger than the other, and it is the surface of the larger indent 246i that engages the button 233b when the rotatable receiver 246 is in the locking position. The surface of the smaller indent 246i engages the button 233b when the rotatable receiver 246 is in the receiving position, and thus prevents the rotatable receiver from rotating past the receiving position. The force required to disengage the surface of the smaller indent 246i from the button 233b is less than the force required to disengage the surface of the larger indent 246i from the button 233b.

The ramp 233 in the illustrated embodiment is configured such that it can also serve as an offloading ramp that allows the rotatable receiver 246 to be removed from the locking position when an opposing force in the counter-clockwise direction is applied to the rotatable receiver 246 sufficient to overcome the inertia created between the ramp 233 and the surface forming the indent 246i. Alternatively, because the button 233b floats within the opening 229, an alternative way by which the rotatable receiver 246 can be removed from the locking position is by pushing the button 233b towards the distal end 240d to disengage the button 233b from the surface that forms the indent 246i.

The bullet-receiving opening or channel 242 formed in the rotatable receiver 246 can extend from its proximal end 246p to its distal end 246d. The opening 242 can be shaped in a variety of ways, but in the illustrated embodiment it has a substantially cylindrical shape that is complementary in shape to the bullet it is configured to receive. As shown, it can be described as having a C-shape. Likewise, a diameter of the opening 242 is such that it is sized to receive a bullet therein. In the illustrated embodiment, a diameter of the bullet-receiving opening 242 is approximately half the size of the diameter of the rotatable receiver 246, thus resulting in the illustrated C-shape. The shape of the opening 242 formed in the rotatable receiver 246, along with the various features described herein to help secure a bullet within the bullet-receiving opening 242, allow a bullet to be inserted into the opening 242 from the side. More specifically, a bullet can be passed from an outside environment, across the plane $P_1$ extending substantially through the first facial surface 250f, and into the bullet-receiving opening 242.

The guide-receiving opening 244 extends substantially transverse to a longitudinal axis LA' of the housing 250, and thus substantially transverse to the opening 242, and it extends through the housing from and through the first side surface 250r to and through the second side surface 250s. As shown, the opening 244 can be defined by an inner wall of the proximal end 250p, an inner wall of the distal end 250d, an inner wall of the first facial surface 250f, and an inner wall of the second facial surface 250g, e.g., predominantly by an inner wall of the guide engaging mechanism 260. The guide-receiving opening 244 can extend in a different plane than the bullet-receiving opening 242. A size and shape of the guide-receiving opening 244 can be complementary to the size and shape of the first arm 222 of the guide arm 220 such that the first arm 222 can extend through the guide-receiving opening 244 and the carriage 244 can be securely locked at one or more locations along a length of the first arm. In the illustrated embodiment, a length L' of the carriage 240 can extend substantially transverse to a length l' of the first arm 222. As described above, as used herein the term substantially transverse does not necessarily mean exactly transverse, at least because of the arcuate configuration of the first arm 222. A person skilled in the art will understand that such a description is generally intended to address the fact that, as shown, the length L' of the carriage 240 is not generally disposed in the same direction as the length l' of the first arm 222.

The guide engagement mechanism 260 that is configured to extend between the upper and lower portions 250a, 250b to form the second facial surface 250g that also defines the guide-receiving opening 244 can be of a similar construction as discussed above with respect to the guide engagement mechanism 160, and thus can also serve as a passive engaging locking mechanism. As shown, the guide engagement mechanism 260 can include a bar 262 that is opposed substantially parallel to the first facial surface 250f, although not necessarily exactly parallel in embodiments in which the first facial surface 250 has a slight taper with respect to the plane $P_2$ as described above. A proximal end 262p of the bar 262 can be a button 266 configured to be pressed by the thumb of a user. As shown, the button 266 includes gripping features formed on a top surface thereof to prevent a user's thumb from slipping off of the button. The portion of the proximal end 262p below the gripping portion can be sized to fit within an elongate opening 251 formed in the upper portion 250a of the second facial surface 250g.

An intermediate portion 262i of the bar 262 can include a male member, as shown a selectively deployable key 264, and two openings 268, 269. The key 264 can have a shape and size that is complementary to a shape and size of the female member formed on the arm guide, e.g., the plurality of slots 230, similar to the key 164 of the carriage 140. The first opening 268 formed in the bar 262 can be for viewing indicia 232 formed on the first arm 222, while the second opening 269 can be used in conjunction with a mechanism for selectively locking a bullet in a third dimension, as described below.

Notably, when a bullet disposed in the carriage 240 is in the intermediate position or the locked position, it is prevented from translating between the two side surfaces 250r, 250s and between the two facial surfaces 250f, 250g. However, the bullet is not necessarily prevented from translating in a third dimensions, along the longitudinal axis LA'. As described in greater detail below, when the carriage 240 is in the intermediate position, a bullet disposed therein can freely translate distally and proximally along the longitudinal axis LA' through the bullet-receiving opening 242, and when the carriage is in the locking position, a bullet disposed therein can translate distally along the longitudinal axis LA' through the bullet-receiving opening 242 when a certain amount of force is applied to the bullet. In the locking position, when such threshold force is not exceeded however, then the carriage 240 is configured to maintain the location of the bullet with respect to the longitudinal axis LA', i.e., the third dimension.

Figure 11:
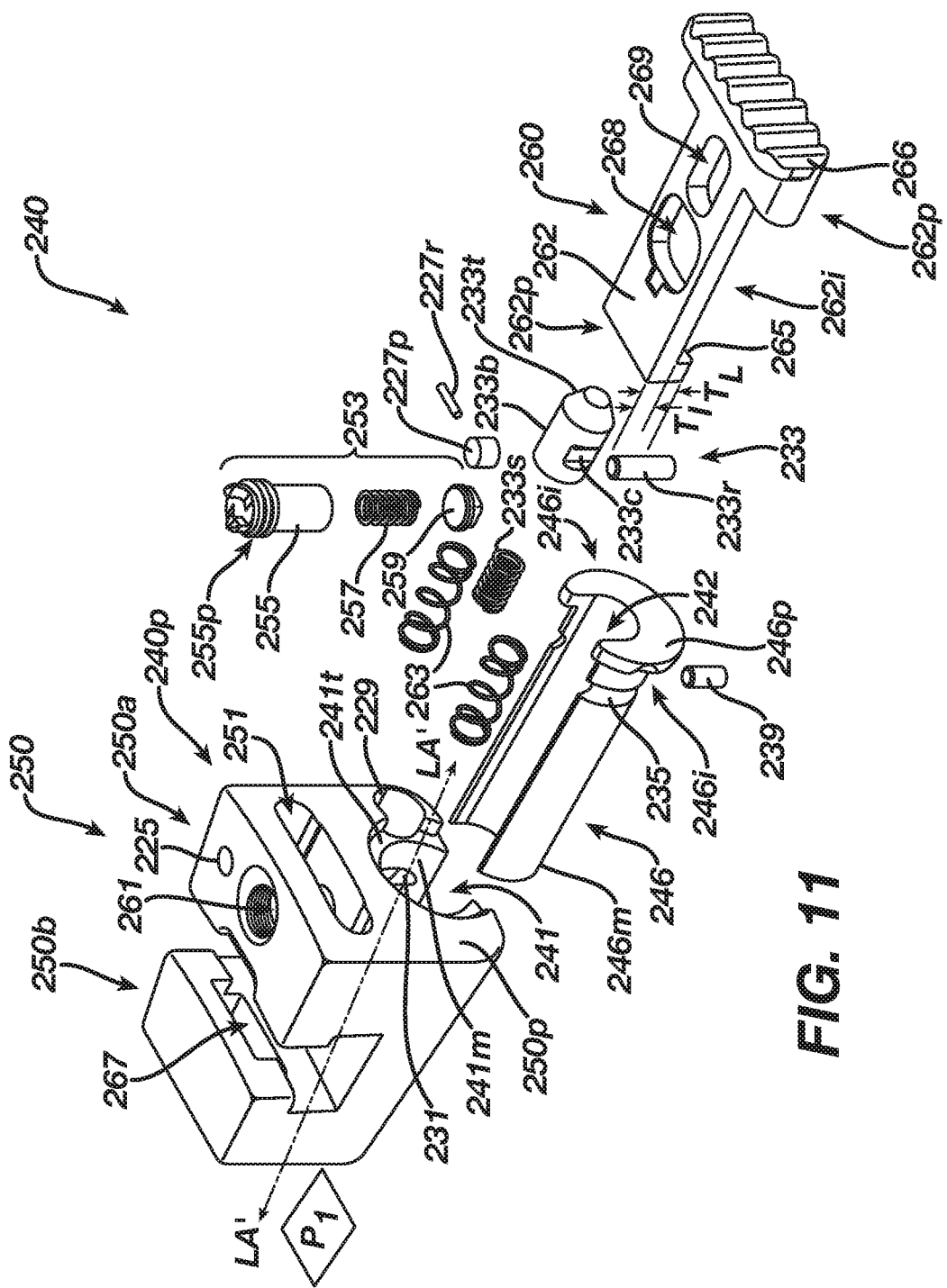
FIG. 11 is an exploded back perspective view of the carriage of FIG. 9A.

The second opening 269 is involved with locking the bullet in a third dimension by being configured to receive a spring-loaded pin 253 that is operable to maintain the location of a bullet disposed in the bullet-receiving opening 242 when a threshold force is not met or exceeded, but then allow the bullet to travel along the longitudinal axis LA' when the threshold force is met or exceeded. The spring-loaded pin 253 can be disposed in the second opening 269, through a central opening 261 formed in the upper portion 250a of the second facial surface 250g, and can extend into the elongate opening 251. As shown in FIG. 11, the spring-loaded pin 253 includes a housing 255 having a spring 257 disposed therein, and a translating distal tip or end cap 259. The end cap 259 is biased by the spring 257 into the opening 242 for receiving the rotatable receiver 246, and thus the bullet. When the rotatable receiver 246 is in an open position to receive a bullet, the end cap 259 is biased out of the opening 242 by the outer surface of the rotatable receiver 246. However, when the rotatable receiver 246 is in the locking position, the end cap 259 can be biased into contact with the bullet to help maintain a location of the bullet with respect to the carriage 240 unless a threshold force applied to the bullet is met or exceeded, in which case the bullet can translate distally. In some embodiments, a proximal end 255p of the housing can be threaded and can be threadingly mated to threads disposed in the central opening 261. Such a configuration helps maintain a location of the pin 253 with respect to the housing 250, and further, can allow a threshold force to be changed. For example, rotating the housing 255 can increase or decrease an amount of force applied to the spring 257, thereby adjusting the threshold force of the pin 253.

Figure 12A:
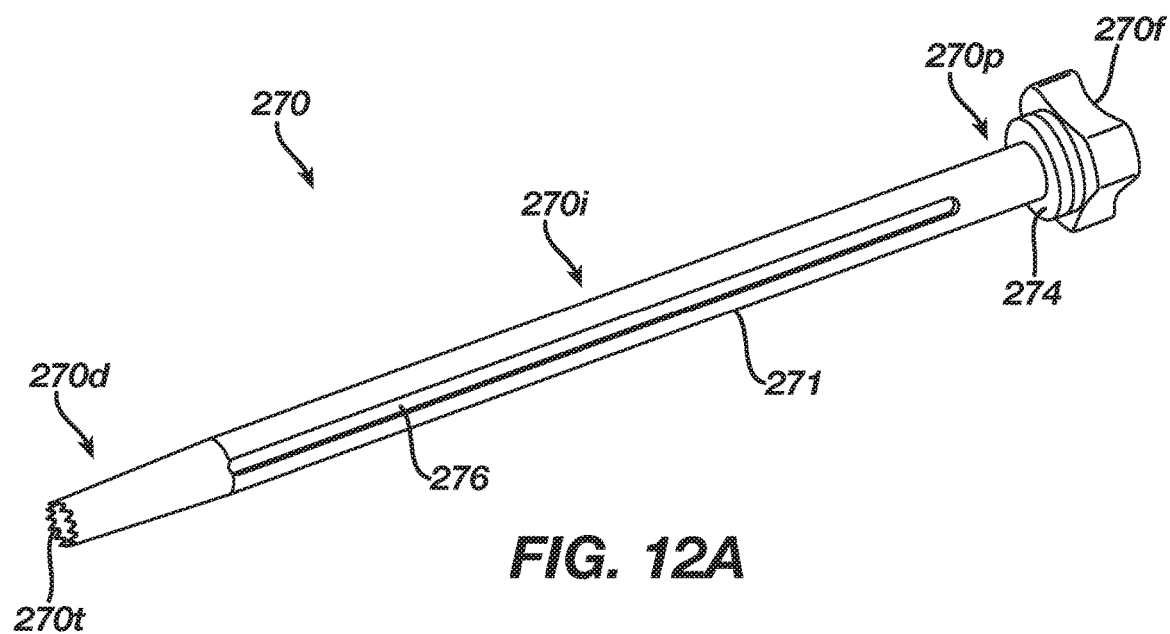
FIG. 12A is a front perspective view of the bullet of FIG. 3.
Figure 12B:
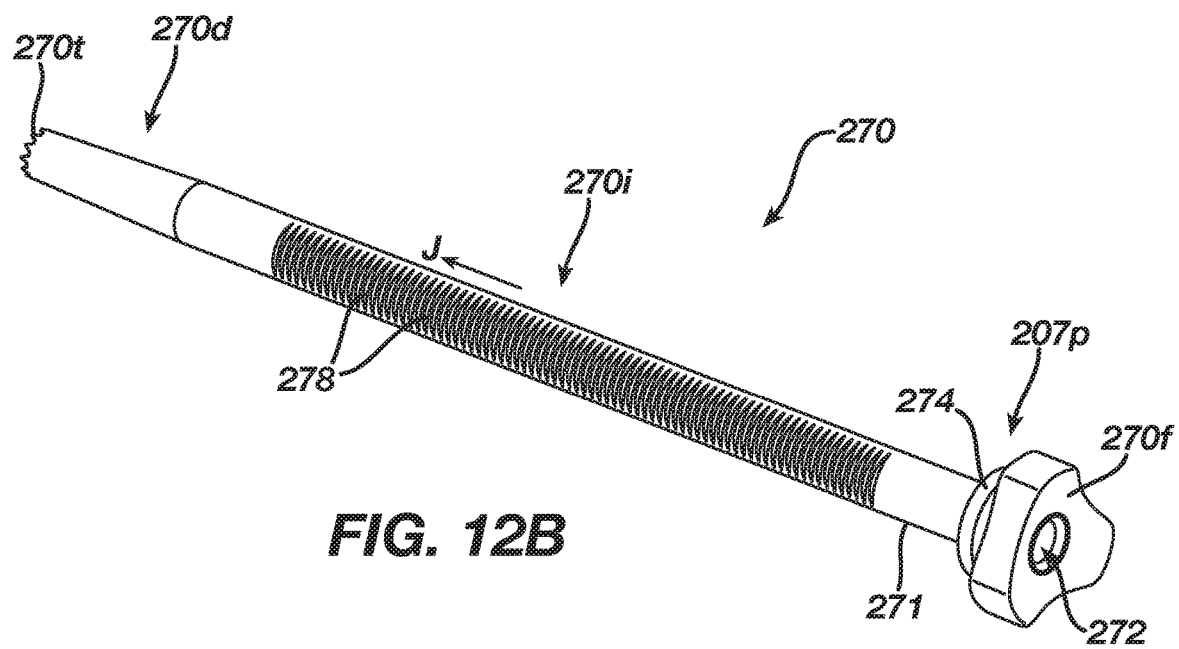
FIG. 12B is a back perspective view of the bullet of FIG. 3.

As described below with respect to FIG. 12B, the distal end cap 259 can contact engagement features formed on the bullet 270, such as ridges 274, to help maintain the bullet 270 location in the absence of application of the distally-applied threshold force. The interaction of the cap 259 and ridges 274 acts as a one-way locking mechanism that prevents the bullet from being advanced proximally, but allows the bullet to advance distally in response to a force that meets or exceeds the threshold force. More particularly, the ridges 274 can be angled such that they only allow for distal travel. When the threshold force is met or exceeded, the bullet 270 will advance distally towards the intended location of the proximal end of the bone tunnel. The value of the threshold force can depend on a variety of factors, including but not limited to the configurations of the carriage and bullet, and can be adjusted as described herein or otherwise known to those skilled in the art.

Springs 263 can be disposed in the elongate opening 251, configured to bias the button 266, and thus the key 264, proximally away from the proximal end 240p of the carriage 240. The springs can be disposed on opposite sides of the bar 262 below the button 266. Similar to the guide engaging mechanism 160, the button 266 can be biased proximally such that the carriage 240 can freely translate along the guide arm 220, including over and past the slots 230 formed in the first arm 222, when the button 266 is depressed against the bias of the springs 263, and the key 264 can passively engage the slots 230 to lock the location of the carriage 240 with respect to the arm 222 when the button 266 is not depressed.

A distal end 262d of the bar 262 can include a ledge 265 such that a thickness $T_L$ of the ledge is greater than a thickness $T_I$ of the intermediate portion. The ledge 265 can be configured to sit within an elongate opening 267 formed in the lower portion 250b of the second facial surface 250g and engage a portion of the lower portion 250b to keep the guide engaging mechanism 260 associated with the housing 250, i.e., it prevent the guide engaging mechanism 260 from falling out of the housing 250.

In some embodiments an identification plug 227p can be provided in the upper portion 250a of the second facial surface 250g. As shown, the plug 227p can be disposed in an opening 225 adjacent to the opening 261 that receives the spring-loaded pin 253, and can be coupled to an identification rod 227r thereto. The identification rod 227r can be disposed in an opening 223 formed in the side surface 250s of the housing 250. The identification plug 227p and identification rod 227r can help a surgeon easily identify the type of carriage, for instance based on the color of the plug 227p and the rod 227r. As a result, during a surgery, the surgeon does not need to test the carriage to see if it is a side-loading carriage or a top-loading carriage. The surgeon can know based on the shape, configuration, and/or color of either or both of the identification plug 227p and identification rod 227r. Other types of identifiers can also be included on the carriage for a similar purpose, including but not limited to labels and/or color-coding of other components of the carriage.

A person having ordinary skill in the art will recognize a variety of other configurations that can be used to form the carriage without departing from the spirit of the present disclosure. Bearing that in mind, in some embodiments, such as the carriages 140 and 240 illustrated herein, a length L, L' of the carriage 140, 240 can be in the range of about 2 centimeters to about 6 centimeters, a width W, W' of the carriage 140, 240 can be in the range of about 1 centimeters to about 5 centimeters, and a thickness T, T' of the carriage 140, 240 can be in the range of about 1 centimeters to about 6 centimeters. In one exemplary embodiment for each of the carriages 140, 240 they have a length L, L' of about 4 centimeters, a width W, W' of about 3 centimeters, and a thickness T, T' of about 3 centimeters. A person having ordinary skill in the art would be able to derive suitable dimensions for components of the carriage, e.g., the guide engagement mechanism, the rotatable receiver, etc., in view of these dimensions, the dimensions of the components associated therewith, and the other disclosures provided for herein or otherwise known in the art. The carriage and related components can be made from a variety of materials, including but not limited to surgical grade metals such as stainless steel and titanium or various polymers. Some features, e.g., the gripping portion of the button, can be configured to be made from suitable materials known to those skilled in the art. Accordingly, a component such as the gripping portion can be made from rubber or other suitable material suitable for providing enhancing a user's grip.

Bullet

A bullet for use in conjunction with the arm guides and carriages provided for herein can have a variety of configurations, depending, at least in part, on the configurations of the arm guide, carriage, and other components with which the bullet is being used, the anatomy of the patient, and the type of procedure being performed. In the illustrated embodiment of FIGS. 12A and 12B, the bullet 270 is an elongate and substantially cylindrical or tubular shaft 271 having a proximal end 270p, a distal tip or end 270d, and an intermediate portion or length 270i extending therebetween. The bullet 270 is cannulated across an entirety of its length, as shown by bore 272, so that a drilling component, such as a drill pin and/or reamer, can be passed through the bullet and to the bone in which the bone tunnel is to be formed.

The proximal end 270p can have a face 270f configured to engage with a distal end of a drill. As shown, the face 270f has a substantially triangular shape and has an outer-facing surface that is concave. The concavity of the face 270f can assist in directing instruments into the bullet 270. Although not visible because of an identifier 274 disposed around an outer surface of the shaft 271, the face 270f can be unitarily formed with the shaft 271 such that the face 270f is an extension of the shaft 271. In other embodiments, the face 270f can be removably and replaceably attached to the shaft 271 so that differently configured faces can be used with a single bullet shaft 271. In the illustrated embodiment, an identifier 274 is disposed around the shaft 271, proximate to the face 270f The identifier 274 can help identify a bullet type, as a person skilled in the art will recognize that bullets can be optimized for certain uses. By way of non-limiting example, some bullets may be more conducive for use with drill pins while another bullet may be more conducive for user with reamers. In other embodiments, no such identifier 274 is used.

As shown, the shaft 271 at the distal end 270d can become tapered, for instance by varying a thickness of a wall of the shaft 271, to make it easier to push the bullet 270 through tissue so it can be seated against the bone. In some embodiments, bone engaging features, as shown teeth 270*t*, can be formed at the terminal end of the distal end 270*d*. The teeth 270*t* help the distal end 270*d* stabilize the location of the bullet 270 with respect to the bone. The stabilization can help provide more accurate measurements when using the bullet 270 to determine the size of the bone stock, and more accurate drilling when drill pins and reamers are being passed through the bullet 270 and into the bone to form the bone tunnel.

The intermediate portion 270*i* can have a groove or channel 276 formed on one side thereof and contact engagement features, as shown ridges 278, on another side thereof. As shown, the groove 276 extends along a length of the intermediate portion 270*i* and is configured to be engaged by a protrusion extending from a surface that forms the bullet-receiving opening, whether that opening is formed in the housing itself or in the rotatable receiver disposed in the housing, e.g., the protrusion being the pin 239 extending into the bullet-receiving opening 246. The deepest portion of the groove 276 can extend far enough into the outer surface of the bullet 270 that the bullet 270 can be disposed in a locked position when the groove 276 is engaged by the protrusion, but not so deep that the groove 276 passes into the bore 272 that forms the cannulated configuration of the bullet 270. By not disposing the groove 276 that deep, the bullet 270 can be held in an intermediate locking position without falling out of the carriage, as described in greater detail elsewhere. While in some embodiments the groove 276 can extend into the bore 272, such a configuration would make it easier for a component such as a drill pin passing through the bullet 270 to unexpectedly pass out of the bore 272 and the groove 276 and to an outside environment. The length of the groove 276 can vary depending on a variety of factors, and thus the illustrated length by no means limits the length or location of the groove. The length of the groove 276 is generally as long as or longer than the desired distance of longitudinal travel for the bullet 270. Otherwise, the pin 239 or related component would not be engaged with the groove 276 at all times as the bullet 270 translates along the longitudinal axis LA' of the housing 250, which would in turn lead to a less secure hold of the bullet 270 in use. In embodiments in which the pin 239 is not involved, such as the embodiment of FIGS. 17A-20B, this is obviously not a concern.

The ridges 278 formed in the outer surface of the intermediate portion 270*i* can extend across at least a portion of the length of the bullet 270. The ridges 278 can be configured to receive the distal tip 259 of the spring-loaded pin 253 that is configured to selectively engage the bullet 270 to temporarily maintain the location of the bullet with respect to the carriage 240. Further, the ridges 278 can be disposed at an angle such that when the bullet 270 is in the locked position and the carriage 240 are in the locking position, the bullet 270 can only be advanced distally along the longitudinal axis LA', and not proximally along the longitudinal axis LA'. More particularly, when the threshold force applied in a direction J is exceeded, the distal tip 259 can retract to allow the bullet 270 to advance along the longitudinal axis LA' until the force applied again falls below the threshold force, at which point the distal tip 259 engages a ridge 278 and maintains the location of the bullet 270 with respect to the carriage 240 at the new location. The interaction of the distal tip 259 and the ridges 278 can be audible such that as the bullet 270 advances or retracts, the distal tip 259 makes noise as it drags along the ridges 278 while the threshold force is overcome. Further, as the force applied falls below the threshold force or is removed all together, a clicking noise can be heard as the distal tip 259 fully engages the ridge 278 to secure the new location. Similar to the length of the groove 276, the length of the ridged portion can generally be as long as or longer than the desired distance of longitudinal travel for the bullet 270 to insure that the distal tip 259 can remain engaged with the bullet 270 at any desired location of the bullet 270 with respect to the carriage 240.

In some embodiments, such as the bullet 170 illustrated in FIG. 15, indicia 177 can be formed on an intermediate portion 170*i* to assist a user in identifying the distance traveled by the bullet and/or identifying a size of a bone stock, as described in greater detail below.

A person having ordinary skill in the art will recognize a variety of other configurations that can be used to form the bullet without departing from the spirit of the present disclosure. In some exemplary embodiments, a length of the bullet can be in the range of about 10 centimeters to about 20 centimeters, and a diameter of the bullet can be in the range of about 4 millimeters to about 8 millimeters. In one exemplary embodiment, a length of the bullet is about 14 centimeters and a diameter of the bullet is about 7 millimeters. The bullet can be made from a variety of materials, including but not limited to surgical grade metals such as stainless steel and titanium or various biocompatible polymers.

Carriage and Bullet

Figure 13:
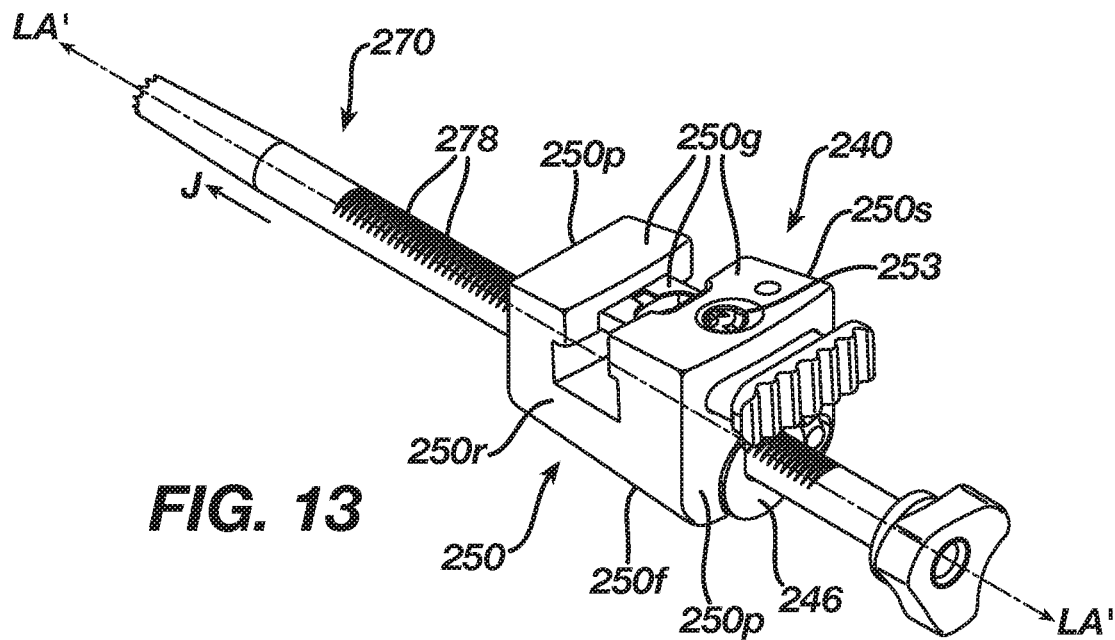
FIG. 13 is an isometric view of the bullet of FIG. 12A disposed in the carriage of FIG. 9A.

FIG. 13 illustrates the bullet 270 disposed in the carriage 240 with the rotatable receiver 246 being in the locking position, and thus the bullet being in the locked position. As shown, in the locked position the bullet 270 is unable to translate between the first and second facial surfaces 250*f*, 250*g*, and is also unable to translate between the first and second sidewalls 250*r*, 250*s*. When the carriage 240 is disposed on the guide arm 220, as shown in FIG. 3, then the bullet 270, by way of the carriage 240, can translate in a direction substantially parallel to the direction extending between the first and second sidewalls 250*r*, 250*s*, i.e., along the length of the first arm 222. As shown in FIG. 3, when the carriage 240 is disposed on the guide arm 220, the first and second facial surfaces 250*f*, 250*g* of the carriage 240 and the first and second facial surfaces 222*f*, 222*g* of the first arm 222 are substantially parallel, which as indicated above does not necessarily mean exactly parallel in view of possible tapered configurations of at least the facial surfaces 250*f* and 250*g*. More particularly, the first facial surface 250*f* extends away from the first facial surface 222*f*, and is located closer to the first facial surface 222*f* than the second facial surface 222*g*. Likewise, the second facial surface 250 extends away from the second facial surface 222*g*, and is located closer to the second facial surface 222*g* than the first facial surface 222*f*.

In the locked position the bullet 270 is able to translate distally along the longitudinal axis LA' of the housing 250. More particularly, when a force applied to the bullet 270 in the distal direction J exceeds the threshold force supplied by the distal tip 259, the bullet 270 advances in the direction J until the force applied no longer exceeds the threshold force. When the threshold force is exceeded, the distal tip 259 bias is overcome and thus the distal tip 259 is pushed back towards the second facial surface 250*g* by each ridge 278. When the threshold force is no longer exceeded, the distal tip 259 is biased back into engagement with a ridge 278, i.e., towards the first facial surface 250*f*, and helps secure the location of the bullet 270 with respect to the rotatable receiver 246 and housing 250.

Figure 14:
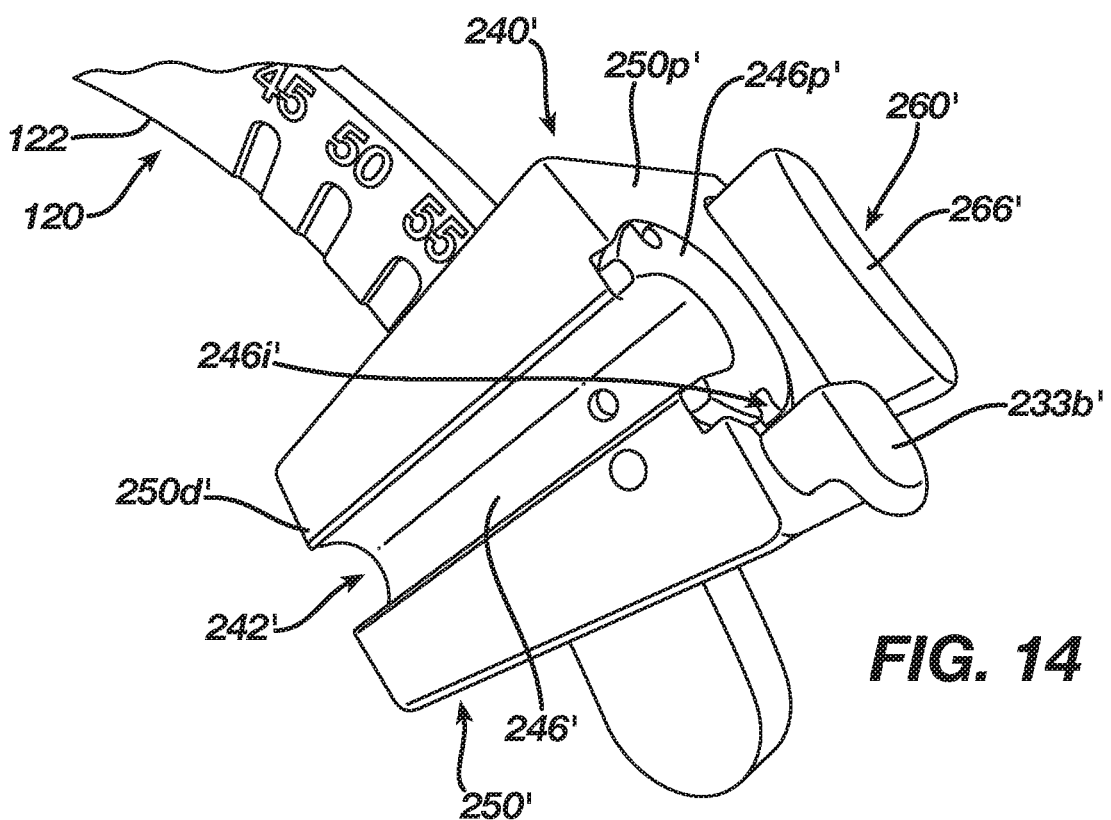
FIG. 14 is an isometric view of another exemplary embodiment of a carriage of a modular guide, the carriage being disposed on the second portion of the guide arm of FIG. 5.

FIG. 14 illustrates an alternative embodiment of a side-loading carriage 240' having a rotatable receiver 246' with a bullet-receiving opening 242', the side-loading carriage 240' being disposed on the first arm 122 of the guide arm 120. The housing 250', rotatable receiver 246', and guide engaging mechanism 260' have many of the same features described above with respect to the side-loading carriage 240. For example, the rotatable receiver 246' is associated with a first facial surface 250f such that when the rotatable receiver 246' is in a receiving position, the bullet-receiving opening 242' extends towards an outside environment, and when the rotatable receiver 246' is in a locking position, the bullet-receiving opening 242' faces a second facial surface 250g' (not shown) and secures the bullet in the locked position in which the bullet is locked in at least two planes as described above. One difference, however, is that the ramp (not shown) disposed in the housing 250' at a location similar to the ramp 233 for the housing 250 is not configured to allow for the rotatable receiver 246' to be disengaged from the locking position by rotating the rotatable receiver 246' in a direction opposite to the direction it was rotated to put it in the locking position. Instead, the button 233b' must be depressed to release the rotatable receiver 246' from the locking position. As shown, the button 233b' protrudes proximally away from the outer surface of the proximal end 250p', and another portion of the button 233b' (not visible) engages a surface that forms an indent 246i' in the proximal end 246p' of the rotatable receiver 246' to hold the rotatable receiver 246 in the locking position. The button 233b' can be depressed towards the distal end 250d' to disengage the portion of the button 233b' that engages the surface that forms the indent 246i' so that the rotatable receiver 246' can be moved out of the locking position and towards the receiving position. As shown, both a button 266' of the guide engaging mechanism 260' and the button 233b' can include a grip formed thereon, e.g., made of rubber or other suitable material, to assist a user in gripping the respective buttons.

Figure 15:
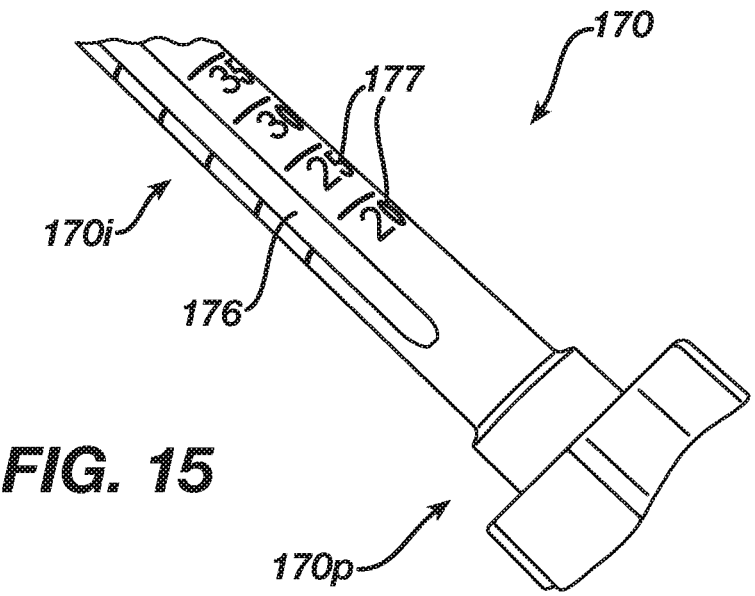
FIG. 15 is a front perspective view of a proximal end of a bullet configured to be used with the carriage of FIG. 14.

The carriage of FIG. 14 can be configured to be used with a bullet of the nature illustrated in FIG. 15. The bullet 170 is similar to the bullet 270 of FIGS. 12A and 12B, and thus only a proximal portion 170p and intermediate portion 170i are illustrated. As shown, the proximal portion 170p, including its face 170f, has a unitary construction with the intermediate portion 170i. Further, the intermediate portion 170i includes indicia 177 formed thereon. The indicia can be formed anywhere along the circumference of the outer surface of the bullet 170, and thus in the illustrated embodiment the indicia are formed adjacent to the groove 176. The indicia 177 illustrated on the bullet 170 are such that the number values decrease the more proximally disposed the value is, with each marking being five millimeters apart from the next one. The indicia 177 can be used to identify a size of the bone stock, i.e., the thickness of the bone to be drilled through and thus the length of the bone tunnel to be drilled. More particularly, as the bullet 170 is advanced distally toward the bone, the values visible to the user decrease because the more distally located values become hidden by a carriage in which the bullet is disposed. Once the distal tip of the bullet 170 contacts the bone to be drilled, with the distal tip 126 of the second arm 124 of the guide 110 being located at the desired distal end of the bone tunnel to be drilled, the bone stock is the value still visible, adjacent to the carriage 140.

Figure 16A:
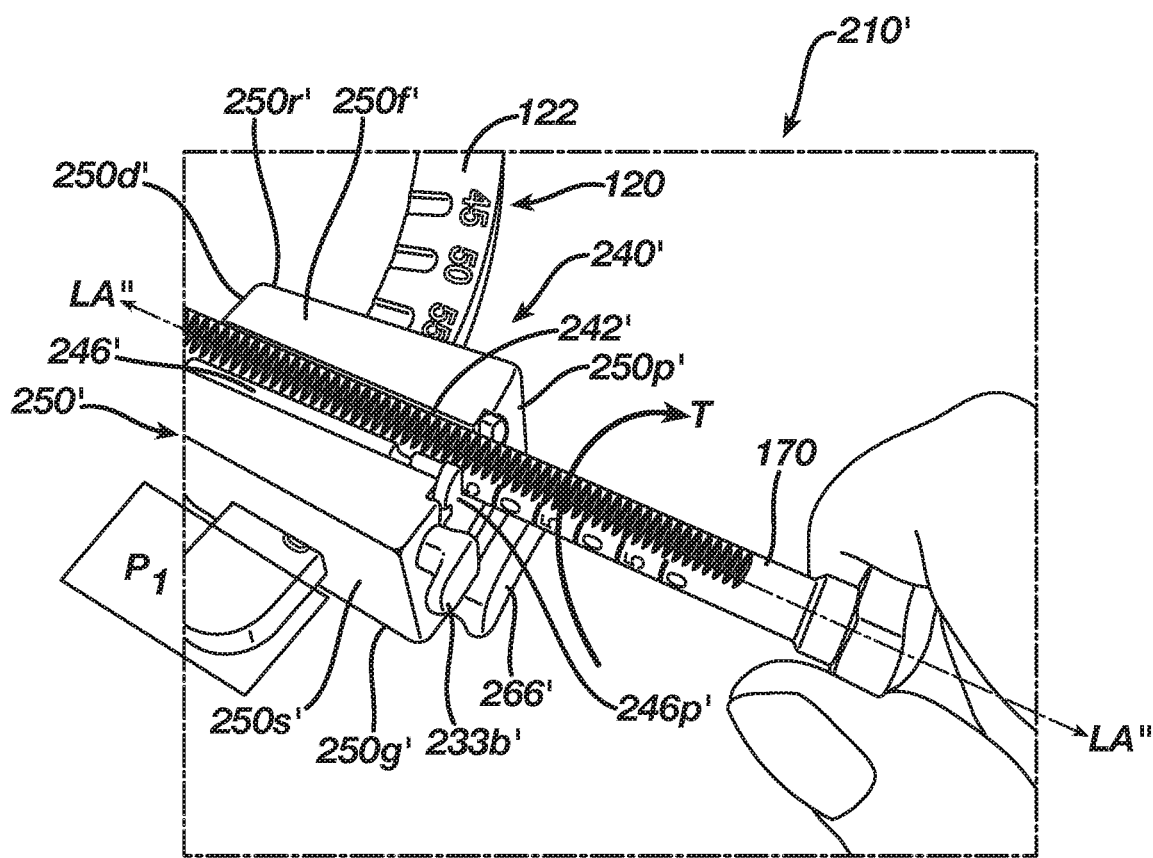
FIG. 16A is a front perspective view of a step of securing the bullet of FIG. 15 to the modular guide of FIG. 14.
Figure 16B:
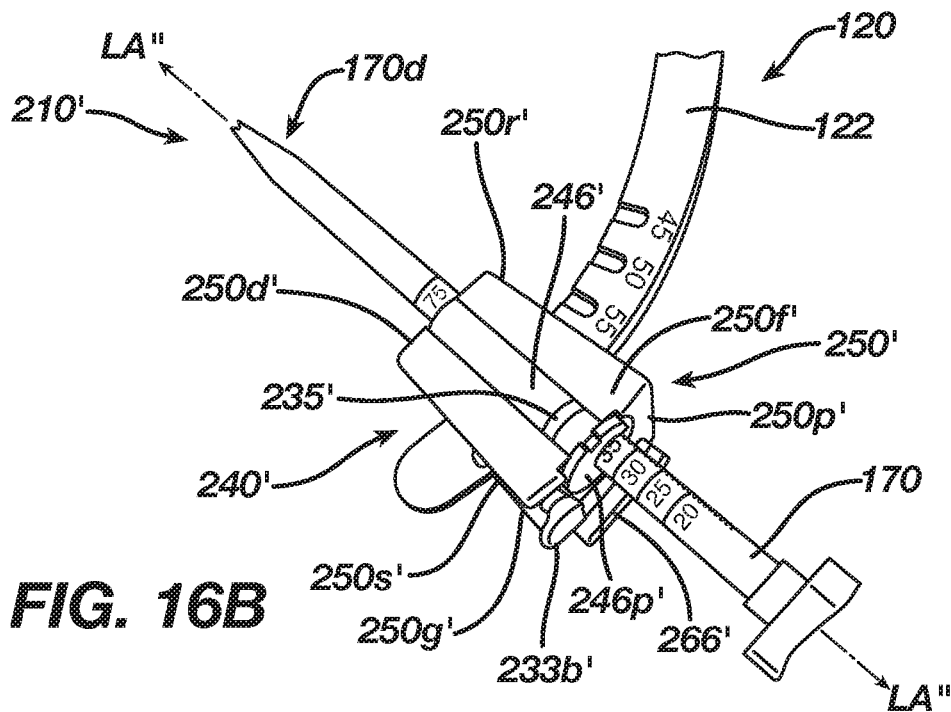
FIG. 16B is a front perspective view of a step of advancing the bullet towards a locked position with respect to the modular guide of FIG. 14.
Figure 16C:
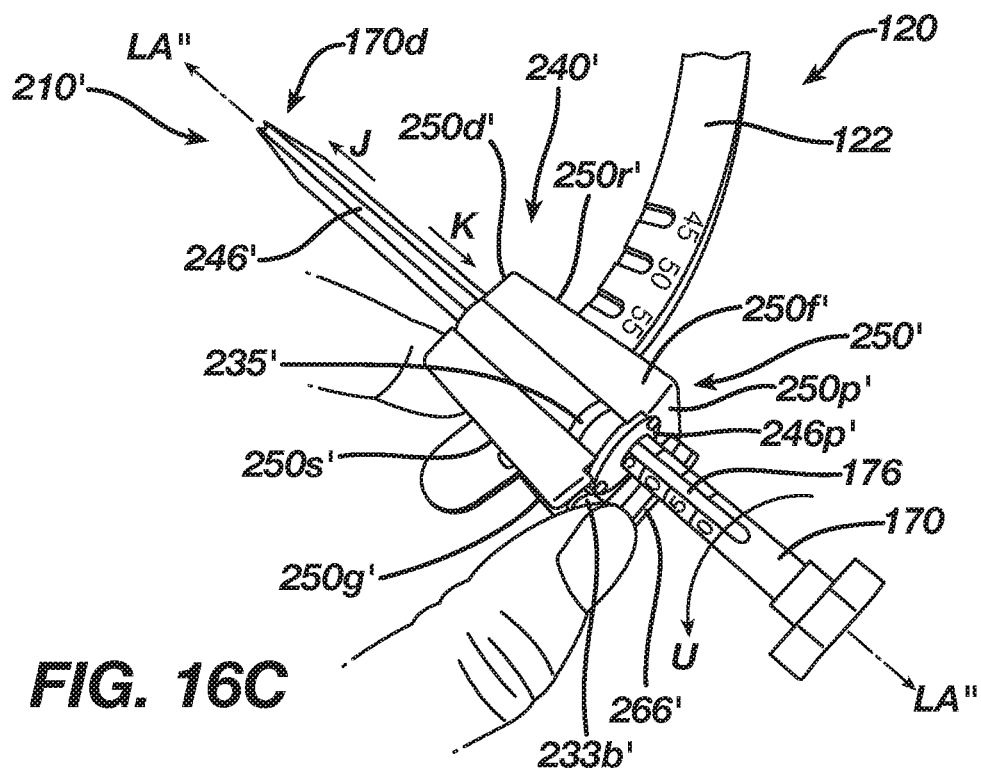
FIG. 16C is a front perspective view of the bullet being disposed in the locked position.

FIGS. 16A-16C illustrate how the bullet 170 can be inserted into a side-loading carriage like the carriage 240' and subsequently removed. In the illustrated embodiment, the carriage 240' is disposed on the arm 120, forming a surgical guide 210'. In FIG. 16A, the bullet 170 has been inserted into the bullet-receiving opening 242' of the rotatable receiver 246' by passing it across the plane $P_1$ extending substantially through the first facial surface 250f. The bullet 170 is then rotated in a clockwise direction T until the protrusion (not shown) extending from the rotatable receiver 246' enters the groove 176 formed in the bullet 170. This places the bullet in its locked position in which the bullet 170 is unable to translate between the two facial surfaces 250f, 250g' or the two side surfaces 250r', 250s' of the carriage 240'. Further, once the bullet 170 is in the locked position, any further torque applied to the bullet 170 in the direction T is also applied to the rotatable receiver 246' so that both the bullet 170 and the rotatable receiver 246' rotate in the clockwise direction T. This moves the rotatable receiver 246' from the receiving position, in which the opening 242' is fully exposed to the outside environment to receive the bullet, and towards the locking position. In the locking position, the rotatable receiver 246' does not rotate in response to the same amount of torque that is applied in the direction T and the bullet 170 remains in its locked position. As described elsewhere herein, a button 266' associated with the guide engaging mechanism 260' can be depressed to allow the carriage 240', and thus the bullet disposed therein 170, to translate and selectively lock along a length of the first arm 122.

FIG. 16B illustrates the rotatable receiver 246' advancing towards the locking position, also referred to as an intermediate position, while FIG. 16C illustrates the rotatable receiver 246' in the locking position. In the intermediate position, the bullet 170 is received by the rotatable receiver 246' and is able to freely translated back-and-forth between the two sides 250r', 250s'.

As shown in FIG. 16C, in the locking position the rotatable receiver 246' has rotated approximately 180 degrees from the receiving position such that the bullet-receiving opening 242' faces towards the second facial surface 250g' instead of towards the outside environment. The rotatable receiver 246', and thus the bullet 170, are maintained at this location by a ramp 233' (not shown) disposed within the opening 241' (not shown) of the carriage 240' that receives the rotatable receiver 246'. The ramp 233' engages first the groove 235' and then the surface that forms the indent 246i' (not shown) in the proximal end 246p' of the rotatable receiver 246', thereby holding the rotatable receiver 246' in the locking position. In this position, the bullet 170 can still translate along the longitudinal axis LA" of the housing 250' such that the distal tip 170d can be advanced towards the distal end 250d' in the direction J. For example, the distal tip 170d of the bullet 170 can translated distally until it contacts the bone. In such a position, the bullet 170 can be used to measure a bone stock, guide a drill pin or other drilling components into the bone for forming the bone tunnel, or be used as a guide for other instruments to be passed through a bone tunnel once the bone tunnel is formed.

The bullet 170 can be removed from the carriage 240' by pushing the release button 233b' down so that the surface that forms the indent 246i' is no longer engaged by the ramp 233' associated with the button 233b'. As a result, when a counter-clockwise torque U is applied to the bullet 170, both the bullet 170 and the rotatable receiver 246' can rotate in the counter-clockwise direction U back towards the initial, receiving position of the rotatable receiver 246', i.e., where the bullet-receiving opening 242' is exposed to the outside environment to receive a bullet therein. As discussed elsewhere herein, in other embodiments the configuration of the carriage can be such that rotation in the opposite direction U is sufficient to move the rotatable receiver from its locking position without pressing a release button like the button 233b'.

Once the rotatable receiver 246' is returned to its initial, receiving position, the bullet 170 can be removed from the carriage 240' by passing it back across the plane $P_1$. The groove 176 of the bullet 170 becomes disengaged from the protrusion of the rotatable receiver 246' just by advancing the bullet 176 across the plane $P_1$ because the direction the bullet 170 is advanced to cross the plane $P_1$ is directly away from the protrusion. Alternatively, the bullet 170 can be passed out of the carriage 240' by pulling it proximally in a direction K until it is removed from the bullet-receiving opening 242'. However, this can be less advantageous because often times a drill pin or other drilling component is disposed in the bullet 170, and thus the drill pin or other drilling component must be long enough to allow the bullet 170 to move fully out of the opening 242' while the drill pin or other drilling component remains extended through the formed bone tunnel. As a result, the drill pin or other drilling component must be long enough to extend fully through the bone tunnel and proximally beyond the guide 210' so that the bullet 170 stays associated with the drill pin or other drilling component when it passes out of the opening 242'. This length is significantly longer than the length just needed to form the tunnel, significantly increase the likelihood of divergence. By passing the bullet 170 out of the side of the carriage, across the plane $P_1$, the drill pin does not need to have the extra length to account for disassociation of the bullet 170 from the guide 210'.

In some exemplary embodiments, after at least a pilot hole of the bone tunnel has been drilled, thereby defining a path for the full formation of the bone tunnel and eventual location of a graft ligament, the bullet 170 can be disassociated from the carriage 240' and the carriage 240' and arm 120 removed from the surgical site while the bullet to provide further guidance for any instruments being used at the surgical site, e.g., a retrograde reamer being passed back through the pilot hole to form the full bone tunnel.

Further Side Loading Carriage and Bullet Embodiment

Figure 20A:
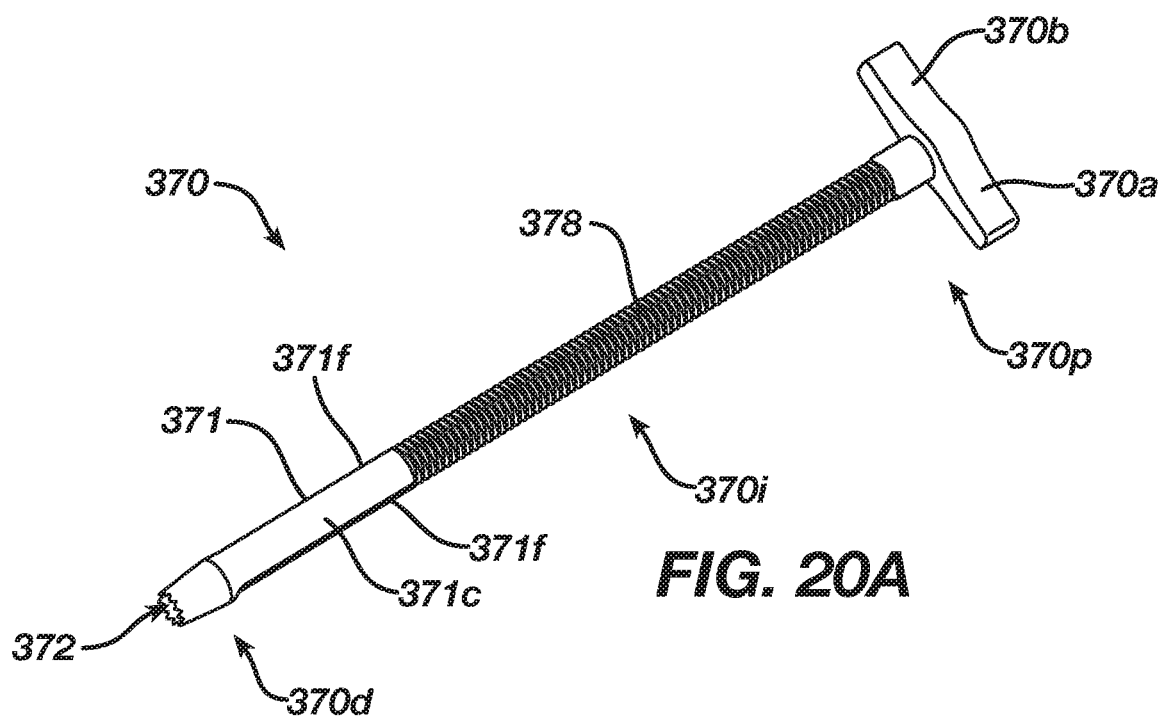
FIG. 20A is a first perspective view of one exemplary embodiment of a bullet configured for use with the carriage of FIG. 17A.
Figure 20B:
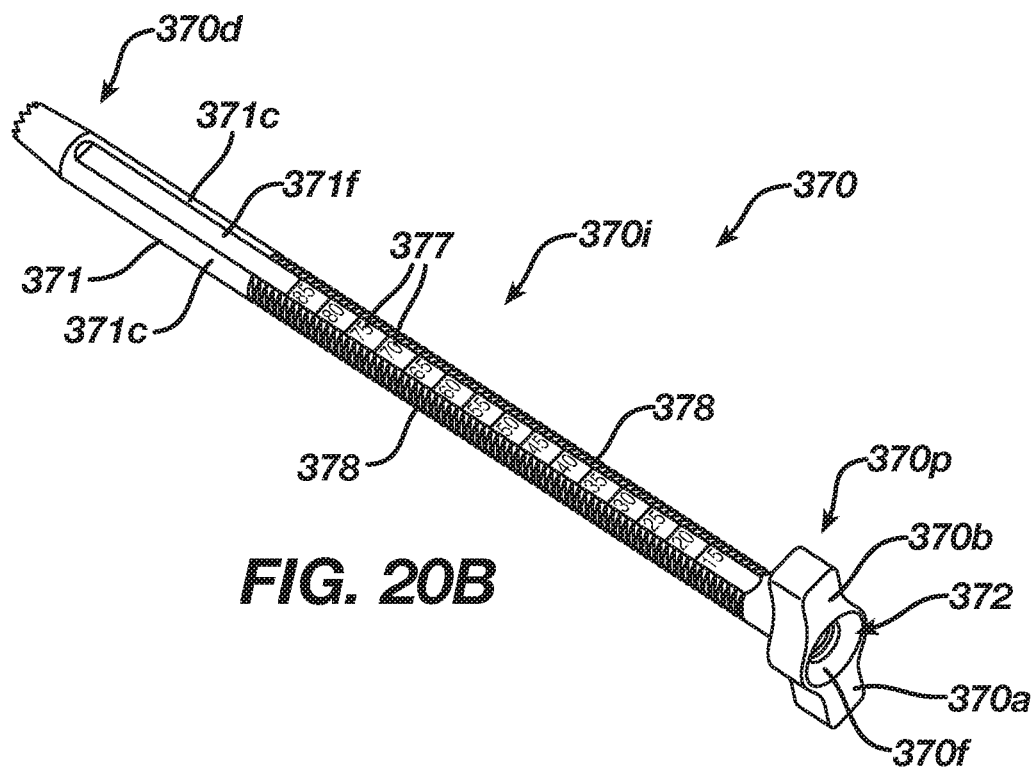
FIG. 20B is a second perspective view of the bullet of FIG. 20A.
Figure 21A:
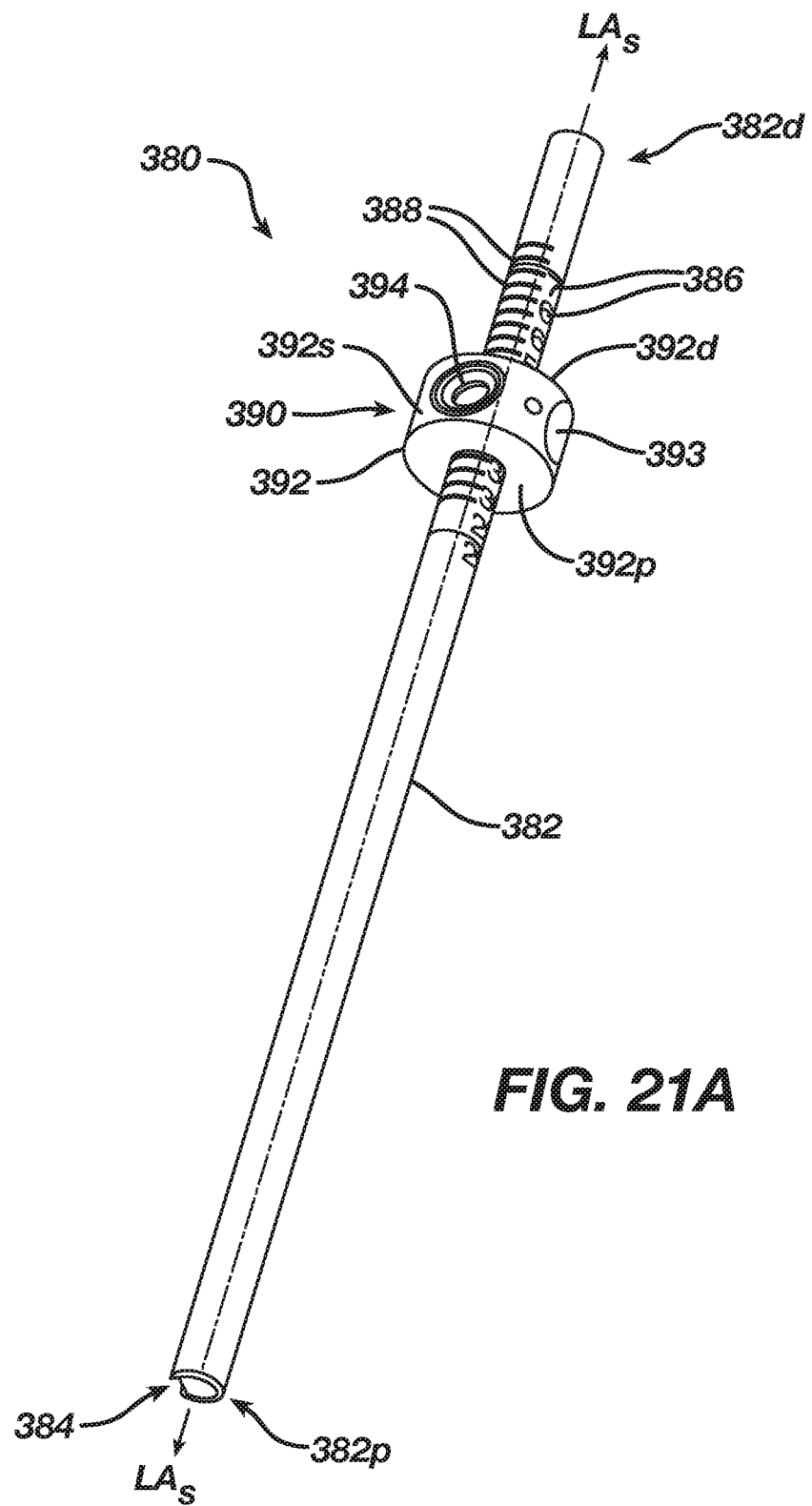
FIG. 21A is an isometric view of one exemplary embodiment of a drill pin depth gage.
Figure 21B:
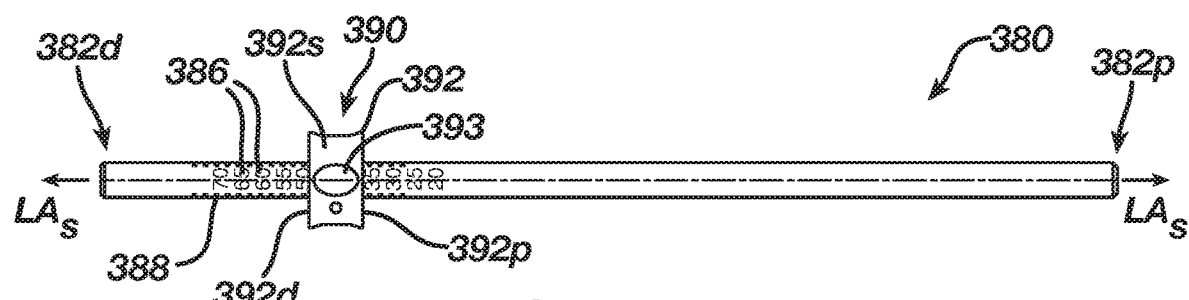
FIG. 21B is a front view of the drill pin depth gage of FIG. 21A.
Figure 21C:
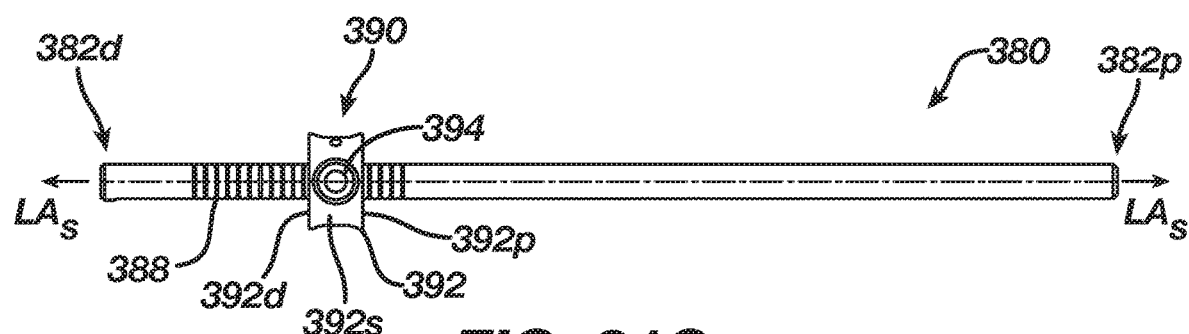
FIG. 21C is a side view of the drill pin depth gage of FIG. 21A.
Figure 21D:
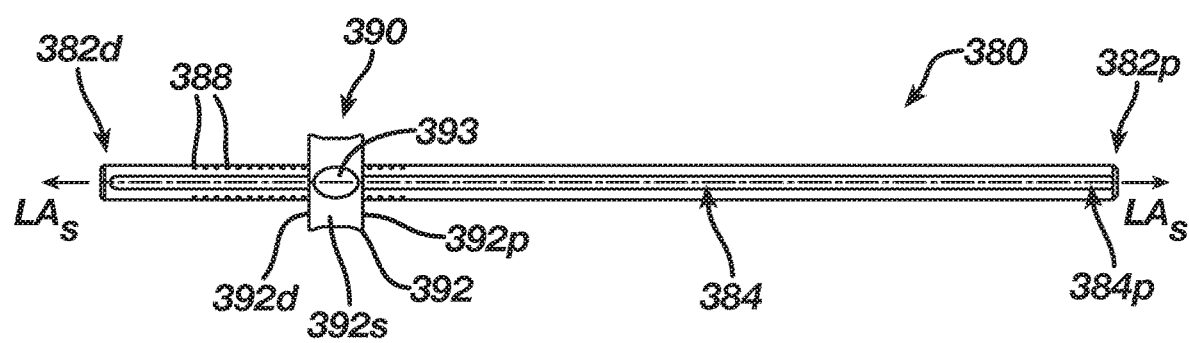
FIG. 21D is a back view of the drill pin depth gage of FIG. 21A.

FIGS. 17A-17C, 18, and 19 illustrate another alternative embodiment of a side loading carriage 340, and FIGS. 20A and 20B illustrate another alternative embodiment of a bullet 370 that is configured to be used with the side-loading carriage 340. The configuration of the carriage 340 is similar to the carriage 240, and thus this embodiment is described with an intention of highlighting the differences between the two carriages. The carriage 340 and bullet 370 can be used in conjunction with the guide arms provided for herein, derivable from the present disclosures, or otherwise known to those skilled in the art.

Figure 17A:
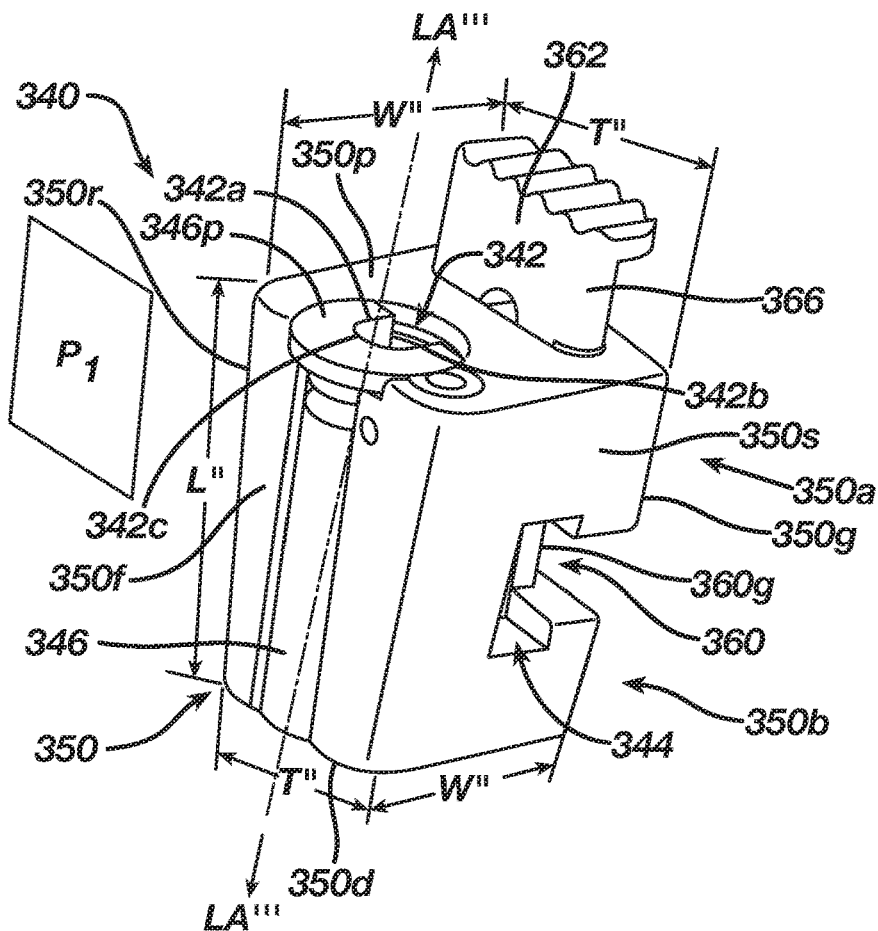
FIG. 17A is an isometric view of one exemplary embodiment of a carriage of a modular guide.
Figure 17B:
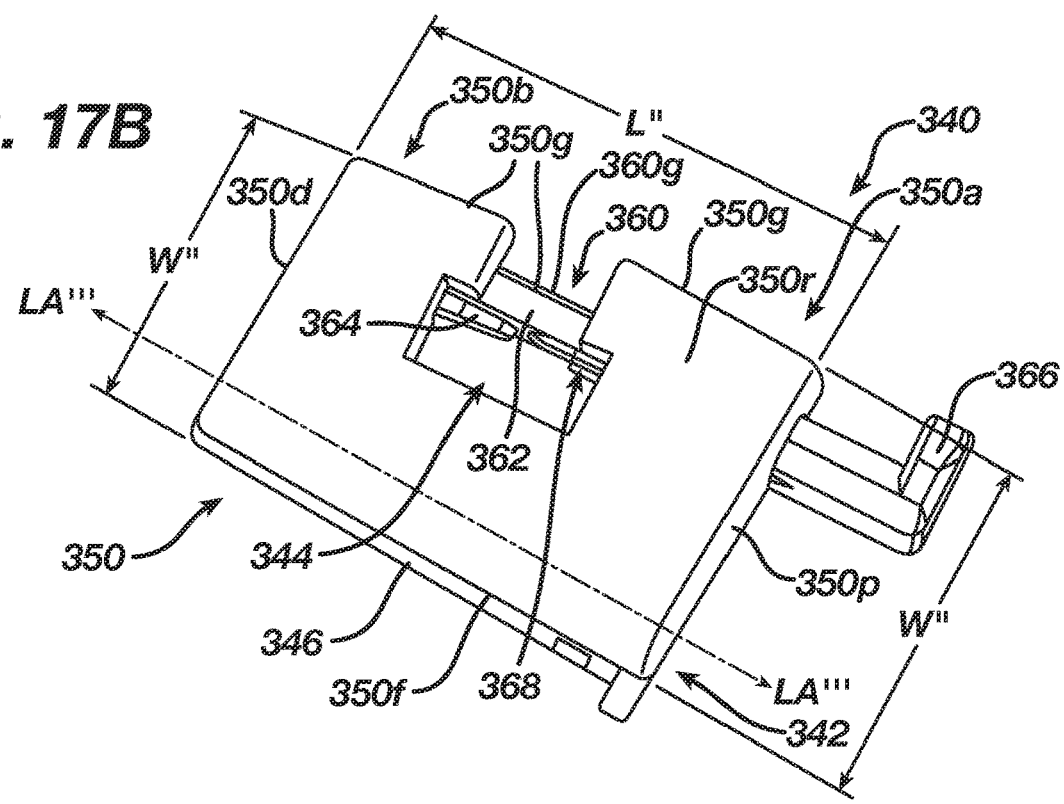
FIG. 17B is a side perspective view of the carriage of FIG. 17A.
Figure 17C:
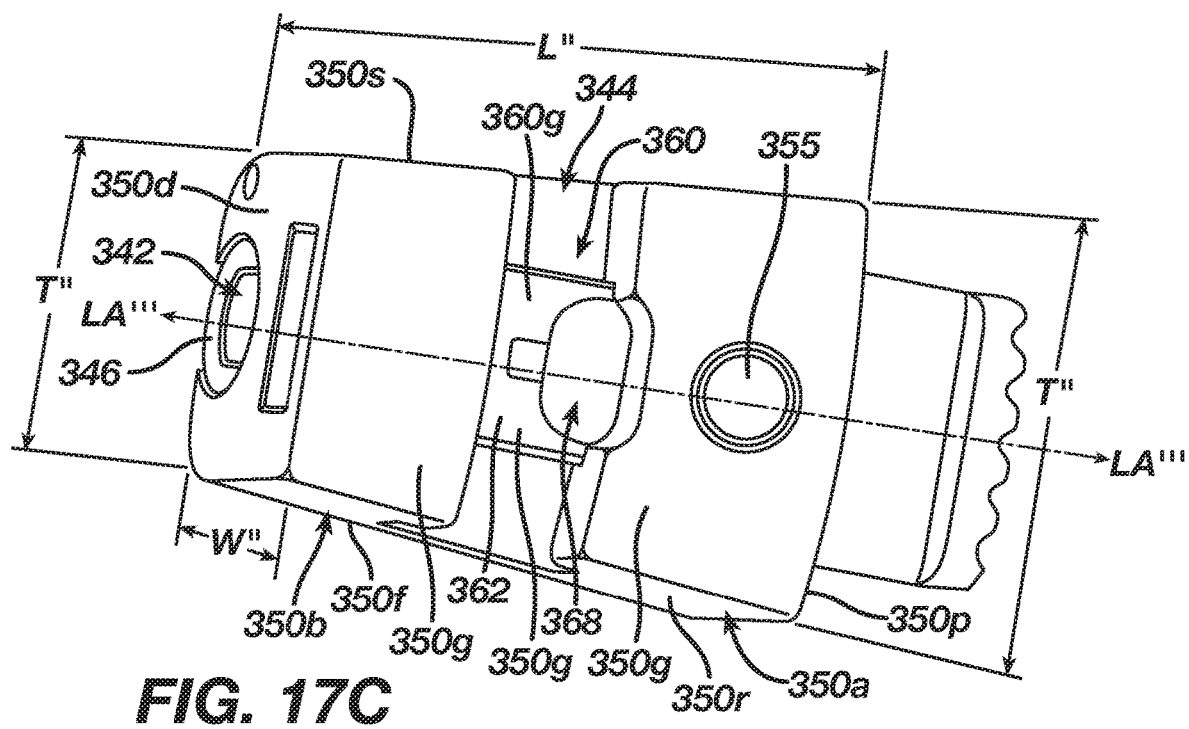
FIG. 17C is a back perspective view of the carriage of FIG. 17B.
Figure 18:
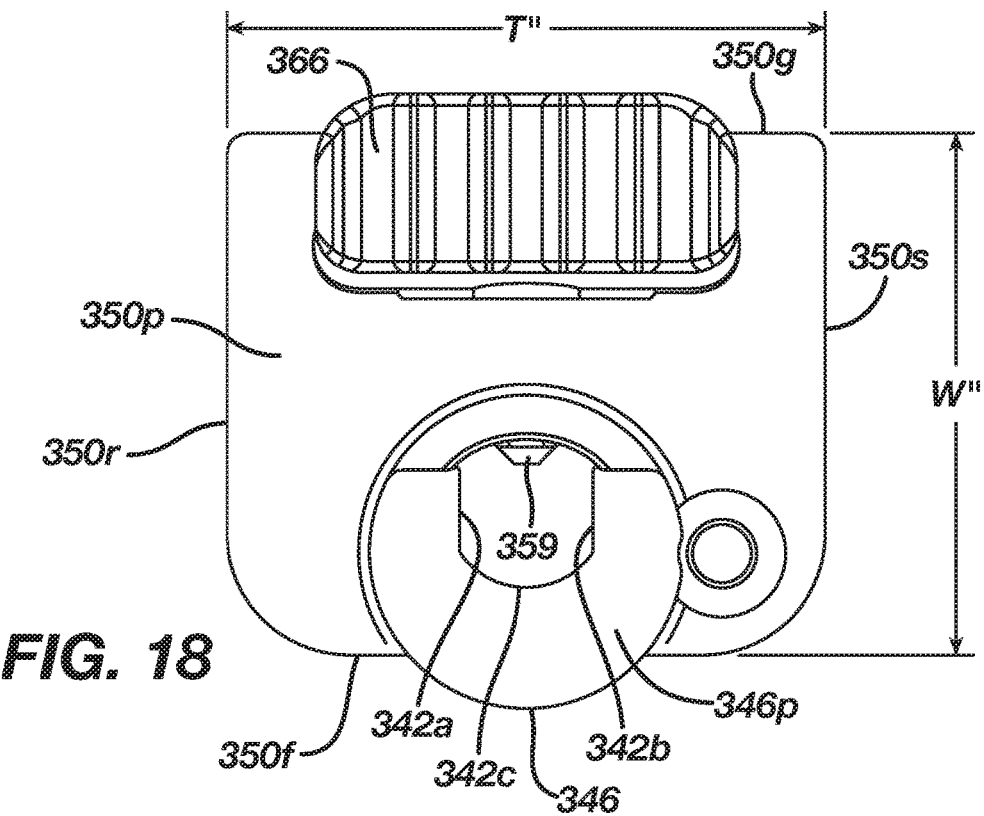
FIG. 18 is a top view of the carriage of FIG. 17A.
Figure 19:
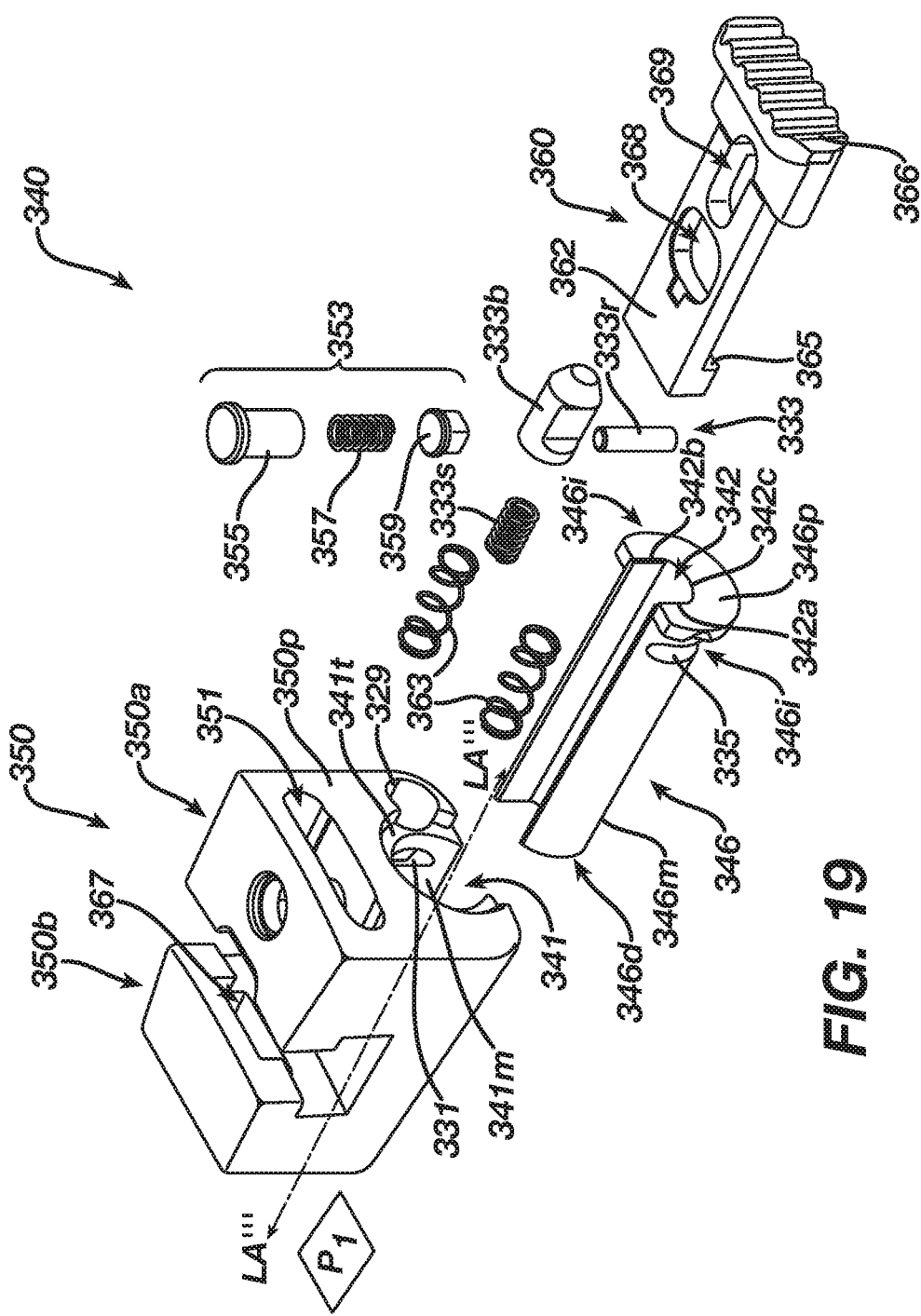
FIG. 19 is an exploded back perspective view of the carriage of FIG. 17A.

The carriage 340 includes a housing 350 that can have many different shapes and sizes, which can depend, at least in part, on the configuration of the device components with which it is being used, the anatomy of the patient, and the type of procedure with which it is being used. Similar to the housing 250 of the carriage 240, the housing 350 has the shape of a trapezoidal prism that includes a proximal end 350p, a distal end 350d, two opposed facial surfaces 350f, 350g extending between the proximal and distal ends 350p, 350d, and two opposed side surfaces 350r, 350s extending between the two facial surfaces 350f, 350g and the proximal and distal ends 350p, 350d. Again, similar to the housing 250, each of the identified surfaces need not be continuous, e.g., the second facial surface 350g can include an upper portion 350a and a lower portion 350b that are not continuous, and a portion of a guide engaging mechanism 360, as shown an outer surface 360g, can extend between the two portions 350a, 350b to form a wall of a guide-receiving opening 344 that extends through the housing 350 from one side surface 350r to the other side surface 350s. A length L", a width W", and a thickness T" of the housing 350 can be defined by the same distances described above with respect to the housing 250, and as illustrated in FIGS. 21A-21C and 22. Typically the length L" is greater than the width W" and the thickness T". As shown in FIG. 17B, the second facial surface 350g of the top portion 350a tapers away from a central portion of the surface 350g such that the width W" gets smaller towards the proximal surface 350p. Likewise, as also shown in FIG. 17B, the second facial surface 350g of the bottom portion 350 tapers away from a central portion of the surface 350g such that the width W" gets smaller towards the distal surface 350d.

The carriage 340 also includes a bullet-receiving opening 342 and a guide-receiving opening 344. More particularly, the bullet-receiving opening 342 is formed within a rotatable receiver 346, which is rotatably disposed within the housing 350. An opening 341 can be formed in the first facial surface 350f to receive the rotatable receiver 346, and can include a main receiving portion 341m and a track portion 341t formed in the proximal end 350p of the housing 350.

While the rotatable receiver 346 generally has the same construction and functionality as the rotatable receiver 246, the receiver 346 is different in at least two significant ways. First, the bullet-receiving opening 342 is shaped differently. As shown, the opening 342 is substantially U-shaped such that opposed sides 342a, 342b are substantially flat, and a curved side 342c extends between the two sides 342a, 342b. This shape is complementary to the shape of the bullet 370 illustrated in FIGS. 20A and 20B, and helps to lock the bullet into the rotatable receiver 346 such that the bullet is in the intermediate position and subsequently the locked position. In that regard, the rotatable receiver 346 also does not include a pin, such as the pin 239, to assist in securing a location of the bullet with respect to the rotatable receiver. The lack of a pin 239 or similar securing mechanism is the second significant difference between the rotatable receivers 246, 346, and thus the carriages 240, 340.

In the illustrated embodiment, a diameter of the bullet-receiving opening 342 is approximately half the size of the diameter of the rotatable receiver 346, thus resulting in the illustrated U-shape. While the shape of the opening 342 is different than the opening 242, it is similar to the opening 242 in that its configuration allows a bullet to be inserted into the opening 342 from the side. More specifically, a bullet can be passed from an outside environment, across the plane $P_1'$ extending substantially through the first facial surface 350f, and into the bullet-receiving opening 342.

Other features of the rotatable receiver 346, including but not limited to the distal end 346d, the main body 346m, the proximal end 346p, the opposed indents 346i, and the track 335, can be included as part of the rotatable receiver 346 and can operate and be configured in a similar manner as the like-numbered components of the rotatable receiver 246. Likewise, other features of the carriage 340 more generally, including but not limited to the guide engagement mechanism 360, and its bar 362, key 364, ledge 365, button 366, and openings 368, 369, springs 363 for biasing the guide engagement mechanism 360, the spring-loaded pin 353 for engaging a bullet disposed in the rotatable receiver 346, and the pin's housing 355, spring 357, and distal tip 359, and the ramp 333, and its components rod 333r, button 333b, and spring 333s, as well as openings that receive the various components of the carriage 340, such as the guide-receiving opening 344, the elongate openings 351, 367 for receiving the guide-engagement mechanism 360, and openings 331 and 329 for receiving portions of the ramp 333, can be included as part of the carriage 340 and can operate and be configured in a similar manner as the like-numbered components and openings of the carriage 240. The carriage 340 does not include the equivalent of an identification plug 227p or rod 227r, which is at least a third difference between the carriage 340 and the carriage 240.

In use, the rotatable receiver 346 generally operates similar to the rotatable receiver 246, and thus the receiver 346 rotates with respect to the housing 350 between a first, receiving position and a second, locking position, which is illustrated in FIGS. 17A-17C and 18. The rotatable receiver also provides for the aforementioned intermediate position in which a bullet disposed therein can translate freely along a longitudinal axis LA''' extending through the opening 342. Further, the exemplary carriage widths, lengths, thicknesses, and materials provided for above with respect to the carriages 140, 240 are equally applicable to the carriage 340.

The configuration of the carriage bullet 370 is similar to the bullet 270, and thus this embodiment is described with an intention of highlighting the differences between the two bullets. In the illustrated embodiment of FIGS. 20A and 20B, the bullet 370 is an elongate and substantially cylindrical or tubular shaft 371 having a proximal end 370p, a tapered distal tip or end 370d, and an intermediate portion or length 370i extending therebetween. The bullet 370 is cannulated across an entirety of its length, as shown by bore 372, so that a drilling component, such as a drill pin and/or reamer, can be passed through the bullet and to the bone in which the bone tunnel is to be formed. While the bullet 370 can be described as being substantially cylindrical or tubular, the shaft 371 is shaped differently than the shaft 271. As shown, the shaft 371 includes two opposed curved portions 371c, and two opposed flat portions 371f. The two opposed flat portions 371f are configured to engage with the flat portions 342a, 342b of the bullet-receiving opening 342 of the carriage 340 to secure the bullet 370 within the carriage 340 and lock the bullet in two planes such that the bullet cannot translate between the first and second facial surfaces 350f, 350g or between the first and second side surfaces 350r, 350s.

The configuration of the proximal end 370p is one way by which the bullet 370 differs from the bullet 270. The proximal end 370p has a more elongate construction, including opposed arms 370a and 370b, which is more conducive to rotating the bullet 370. The additional length of the opposed arms 370a, 370b allow a user more leverage when providing a rotational force to the bullet 370, and are also easier to find and grip during the course of a surgical procedure. Similar to the proximal end 270p, the proximal end 370p does include a concave portion 370f disposed around the bore 372 that can assist in directing instruments into the bullet 370.

The intermediate portion 370i is different from the intermediate portion 270i in at least two different ways. First, there is no equivalent groove or channel 276 formed in the intermediate portion 370i. This is because the carriage 340 does not include the equivalent pin 239 to be received by the carriage. The lack of a groove or channel also allows for the second difference, which is that the engagement features, as shown ridges 378, can be disposed on opposed sides 371c of the intermediate portion 370, with indicia 377 formed on the two other opposed sides 371f to assist a user in identifying the distance traveled by the bullet and/or identifying a size of a bone stock. The ridges 378 can be similarly constructed as the ridges 278, and thus they can be angled to allow for only distal advancement of the bullet 370 along the longitudinal axis LA''' when the bullet is disposed in the locked position in the carriage 340. The illustrated embodiment, like the other carriage and bullet embodiments, does not permit advancement of the bullet 370 proximally when the carriage 340 is in the locking position and the bullet 370 is in the locked position. Further, the exemplary bullet widths, lengths, thicknesses, and materials provided for above with respect to the bullets 170, 270 are equally applicable to the bullet 370.

Drill Pin Depth Gage

FIGS. 21A-21D illustrate one exemplary embodiment of a drill pin depth gage 380. A drill pin depth gage 380 can be used to help set a maximum distance of travel for a drill pin that forms a bone tunnel in bone, sometimes referred to as a terminal distal travel location, so that the drill pin does not travel further than desired and caused undesirable damage to surrounding tissue. In some embodiments the bone tunnel can be a pilot hole that is later expanded, for instance using a reamer or retrograde reamer. The gages 380, 480 provided for herein can be used in conjunction with the devices, systems, and methods provided for herein, e.g., modular guides and bullets, as well as in conjunction with other devices, systems, and methods with which a drill pin is used to form a bone tunnel.

The drill pin depth gage 380 generally includes an elongate shaft or guide tube 382 and an indicator 390. The indicator 390 can be configured to be move along a length of the shaft 382 and selectively engage the shaft 382 to lock a location of the indicator 390 with respect to the shaft 382 to indicate a particular maximum length or distance. The gage 380 can then be used in conjunction with a drill to chuck a drill pin to the drill, thereby setting the maximum travel distance for that drill pin.

Shaft

As shown, the elongate shaft 382 is substantially cylindrical and has a bore or channel 384 extending through a substantial length thereof. The channel 384 extends from a proximal end 382p and towards a distal end 382d of the shaft 382 and is configured to have a drill pin disposed therein. A proximal portion 384p of the channel 384 can have a diameter that is larger than the rest of the channel 384 to provide a larger receiving region to insert the drill pin into the channel 384. This larger diameter can also help allow the gage 380 to sit flush against the chuck of the drill so that true measurements can be made and relied upon when chucking the drill pin to the drill. While the channel 384 can be extended all the way through the shaft 382, in the illustrated exemplary embodiment only one end is open to clearly delineate to the user the end from which the measurement should be made, i.e., the proximal end 382p.

Indicia 386 can be formed on an outer surface of the shaft 382 to indicate measured bone stock lengths. In particular, the indicia 386 formed on the shaft 382 can correlate to bone stocks measured at the surgical site. Thus, in some embodiments, the indicia 386 formed on the gage 380 can be the same indicia formed on the bullet such that a measurement of bone stock made by the bullet can be used in conjunction with the gage 380 to set the same measurement on the gage 380, as will be discussed in greater detail below.

In the illustrated embodiment, the indicia 386 are formed more proximate to the distal end 382d than the proximal end 382p, with the largest bone stock value being located most distal and the values decreasing as the indicia 386 extend proximally. The values of the indicia 386 can have a range of values, depending, at least in part, on the anatomy of the patient and the type of procedure being performed, but in the illustrated embodiment the values begin at 20 millimeters and extend to 70 millimeters, increasing in increments of 5 millimeters. Further, in the illustrated embodiment the indicia 386 are lines that extend approximately half of the circumference of the shaft 382 with values disposed directly below their corresponding lines, although any other configuration for forming indicia on a device can also be used without departing from the spirit of the present disclosure.

Engagement grooves 388 can also be formed on the outer surface of the shaft 382. The engagement grooves 388 can be configured to be engaged by a portion of the indicator 390 to allow the indicator 390 to lock at a location along the shaft 382. As shown, the engagement grooves 388 are formed closer to the distal end 382*d* than the proximal end 382*p*, at approximately the same location along a length of the shaft 382 as the indicia 386. This allows the grooves 388 to be engaged by the indicator 390 in conjunction with identifying the relevant bone stock value. In some embodiments, the number of grooves 388 can be equal to the number of values or marks of indicia 386 such that each groove is associated with one value or mark, but in the illustrated embodiment there are more grooves than marks, which allows for bone stock measurements that fall in between the marks of the indicia 386 to be indicated on the shaft 382 by the indicator 390. Further, in the illustrated embodiment the grooves 388 have a length that is greater than half the circumference of the shaft 382, which is why the grooves can be seen in each of the FIGS. 21B-21D views, although the grooves 388 can have any length or shape suitable for engagement by the indicator 390. The size and shape of the grooves can depend, at least in part, on the configuration of the indicator with which the shaft is being used.

The shaft 382 itself can have a variety of shapes and sizes, depending, at least in part, on the configuration of the indicator 390, drill pin, or other components with which it is used and the type of procedure being performed, but in the illustrated embodiment the shaft 382 has a length approximately in the range of about 10 centimeters to about 40 centimeters, and a diameter approximately in the range of about 5 millimeters to about 15 millimeters, and in one embodiment the length of the shaft is about 23 centimeters and the diameter of the shaft is about 8 millimeters. Any number of materials can be used to form the shaft, including but not limited to surgical grade stainless steel, titanium, and polymers.

Indicator

The indicator 390 is configured to be complementary to the shaft 382 so that the indicator 390 can easily translate along a length of the shaft 382 and be locked at a location along the length to set the maximum length of distance for the drill pin. The indicator 390 is illustrated with some particularity in FIGS. 22A-22D. While the indicator 390 can have a variety of shapes and sizes, in the illustrated embodiment the indicator 390 has a substantially cylindrical housing 392 with a proximal end face 392*p*, a distal end face 392*d*, a cylindrical sidewall 392*s* extending between the two faces 392*p* and 392*d*, and a central opening 392*c* extending from the proximal end face 392*p* and through the distal end face 392*d* to allow the shaft 382 to pass therethrough. As shown in the illustrated embodiment, the sidewall 392*s* can be concave around a circumference of the indicator 390 to make it easier for a user to grip or hold the indicator 390 and move it along the shaft 382. One or more finger grooves 393 can also be formed in the sidewall 392*s* for further gripping benefits. As shown, two finger grooves 393 are formed on opposed sides of the sidewall 392*s*, and a third finger groove 393 is formed on an opposite side of a button 394. The functionality of the button 394 is described below with respect to a groove engaging feature 396.

A key 398 can extend from an inner wall 390*i* of the indicator 390 that forms the central opening 392*c*. The key 398 can be sized and configured to be received in the channel 384 formed in the shaft 382. This allows the indicator 390 to be translated along a length of the shaft 382 without rotating a significant amount with respect to a central longitudinal axis LA, of the shaft 382, and while maintaining a close relationship with the shaft 382. As shown, the key 398 can have a rectangular cross section with a tapered upper surface 398*t*. Any other number of configurations can be used to form the key 398 provided that the configuration is complementary to the configuration of the channel 384 of the shaft 382. Further, while in the illustrated embodiment the key 398 is disposed closer to the distal face 392*d* than the proximal face 392*p*, in other embodiments the key 398 can be disposed approximately equidistant from the two faces 392*p*, 392*d*, or closer to the proximal face 392*p*.

Figure 22A:
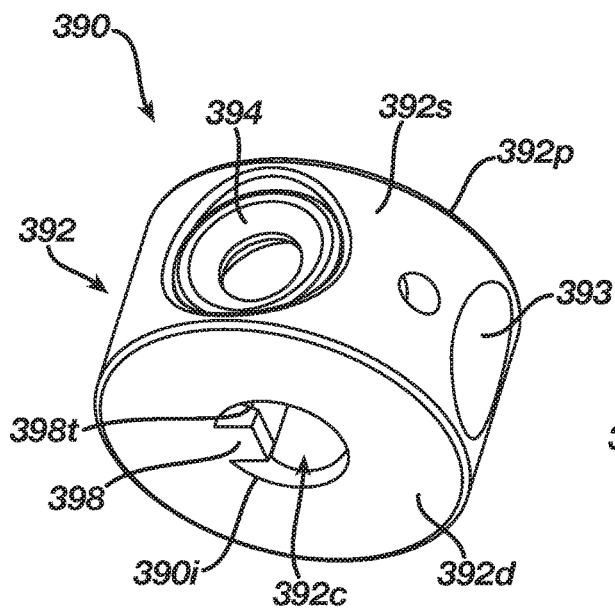
FIG. 22A is an isometric view of an indicator of the drill pin depth gage of FIG. 21A.
Figure 22B:
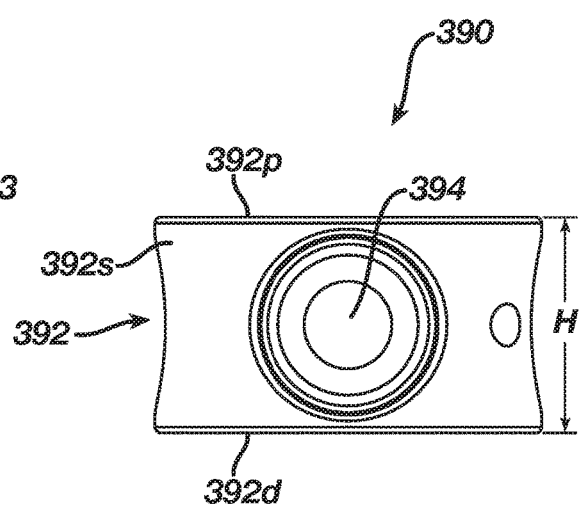
FIG. 22B is a side view of the indicator of FIG. 22A.
Figure 22C:
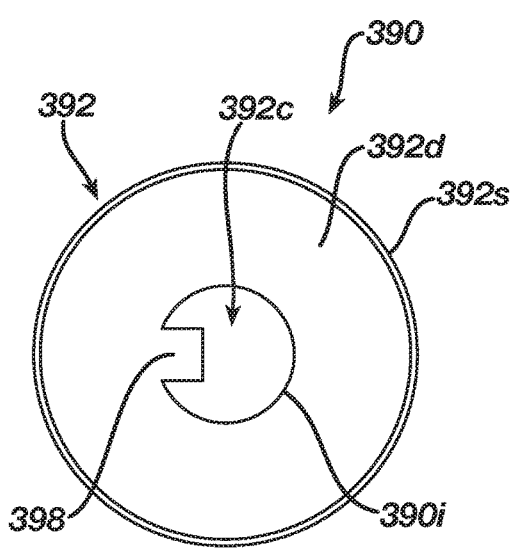
FIG. 22C is a top view of the indicator of FIG. 22A.
Figure 22D:
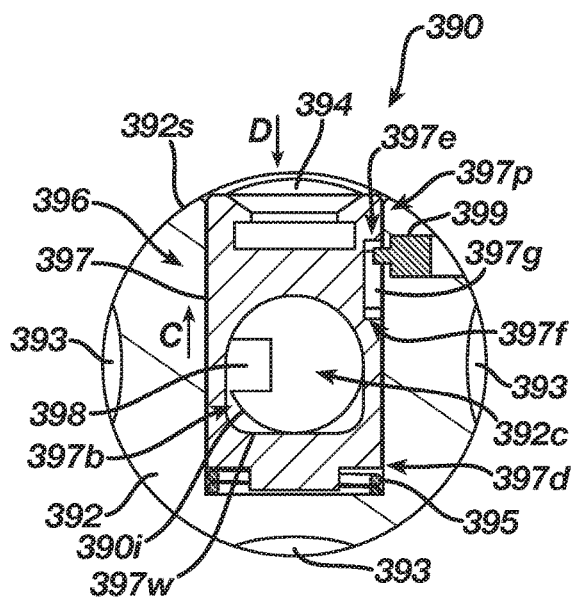
FIG. 22D is a cross-sectional top view of the indicator of FIG. 22C.

A selectively deployable groove engaging feature 396 can also be provided as part of the indicator 390. While a variety of configurations can be used to selectively lock a location of the indicator 390 with respect to the shaft 382 by engaging the grooves 388, in the illustrated embodiment the groove engaging feature 396 includes a translatable block 397 disposed within the indicator 390. The block 397 can include an opening 397*b* formed therein with an inner wall 397*w* of the opening 397*b* disposed opposite from the button 394 being configured to selectively sit within a groove of the grooves 388 when the block 397 is in the locked position. The block 397 can be biased in the locked position, for instance by a spring 395 disposed at a second end 397*d* of the block 397 that bias the block in a direction C, radially away from the shaft 382. A button 394 disposed at a first end 397*p* of the block 397 can be operated by a user to counteract the bias of the spring 395, thereby moving the block 397 from the locked position to a translating position. FIG. 22D illustrates the block 397, and thus the indicator 390, in the translating position. As shown, a force applied to the button 394 in a direction D, radially towards the shaft 382, translates the block 397 radially towards the finger groove 393 that is opposed to the button 394, and thus moves the inner wall 397*w* in the same direction. In use, such movement disengages the inner wall 397*w* from the grooves 388 formed in the shaft 382, and thus allows the indicator 390 to translate along a length of the shaft 382. When a force applied to the button 394 is no longer sufficient to overcome the biasing force supplied by the spring 395, the block 397 radially advances in the direction C and is able to engage the a groove of the grooves 388 with the inner wall 397*w* to establish a locked position.

A pin 399 can be disposed within the indicator 390 to prevent the block 397 from falling out of the indicator 390. As shown, the pin 399 sits within a groove 397*g* formed in an outer wall of the block 397, and engages one end wall 397*e* of that groove 397*g* when the indicator 390 is in the translating position. The pin 397*g* can be configured to engage an opposed end wall 397*f* of the groove 397*g* when the indicator is in the locked position. In other embodiments, the pin 399 does not necessarily engage end walls 397*f*, 397*g* when in either or both of the translating or locked positions.

The location of the button 394 and the inner wall 397*w* thereof can depend, at least in part, on the configuration of the shaft 382 along which the indicator 390 is configured to translate and the location of other components of the indicator, such as the key 398. In the illustrated embodiment, when viewing a location of the button 394, the inner wall 397w, and the key 398 from a perspective of the inner wall 390i, the button 394 and the inner wall 397w are opposed from each other, about 180 degrees around the inner wall 390i from each other, while the key 398 sits about 110 degrees from each of the inner wall 397w and the button 394.

The indicator 390, and the components thereof, can have a variety of shapes and sizes, depending, at least in part, on the configuration of the shaft 382, drill pin, or other components with which it is used and the type of procedure being performed, but in the illustrated embodiment the indicator has a diameter approximately in the range of about 0.5 centimeters to about 5 centimeters, and a height H approximately in the range of about 5 millimeters to about 20 millimeters, and in one embodiment the diameter of the indicator is about Z centimeters and the height H is about 12 millimeters. Any number of materials can be used to form the indicator, including but not limited to surgical grade stainless steel, titanium, and polymers. The indicator 390 can, but does not have to, be made from the same material as the shaft 382.

Use of the Drill Pin Depth Gage and a Modular Guide

When the indicator 390 is coupled to the shaft 382, they can be used to associate a measured bone stock with a drill pin such that a length of the drill pin extending from a drill is no longer than necessary to form the bone tunnel in bone. This prevents the drill pin from passing through the bone after forming the distal end of the bone tunnel and contacting tendons or other tissue and causing undesirable damage to the same. In the illustrated embodiment, the proximal face 392p of the indicator 390 is configured to be aligned with the value or mark of the indicia 386 that is the bone stock measurement. As a result, when a drill pin is disposed in the channel 384 of the shaft 382, the distal tip of the drill pin can abut the proximal face 392p, setting that as the maximum distance of travel for the drill pin. A drill pin can then be chucked at its proximal end such that a distal portion of the drill abuts the proximal end 382p of the shaft 382. This results in a configuration in which the length of the bone stock plus the length of the bullet is equal to the length of the drill pin that is exposed beyond the chuck. An illustrated embodiment of using a drill pin depth gage to set the terminal distal travel location of the drill pin is provided in FIGS. 23A-23L, although the drawings are not to scale. These figures also illustrate using a modular guide and bullet to measure a bone stock and drill both a tibial and femoral tunnel in a knee. The surgical procedure illustrated in FIGS. 23A-23L uses both an alternative embodiment of a drill pin depth gage, gage 480, and alternative embodiments of a modular guide 410 and bullet 470. The features and components of such devices can be similar to those described herein. Notably, although the modular guide 410 does not include a carriage and instead the bullet 470 is mated directly to a first arm 422 of the guide arm 420 of the modular guide 410, a person having skill in the art will understand how guides having carriages can also be used in conjunction with the procedure illustrated in FIGS. 23A-23L in view of the present disclosure.

Figure 23A:
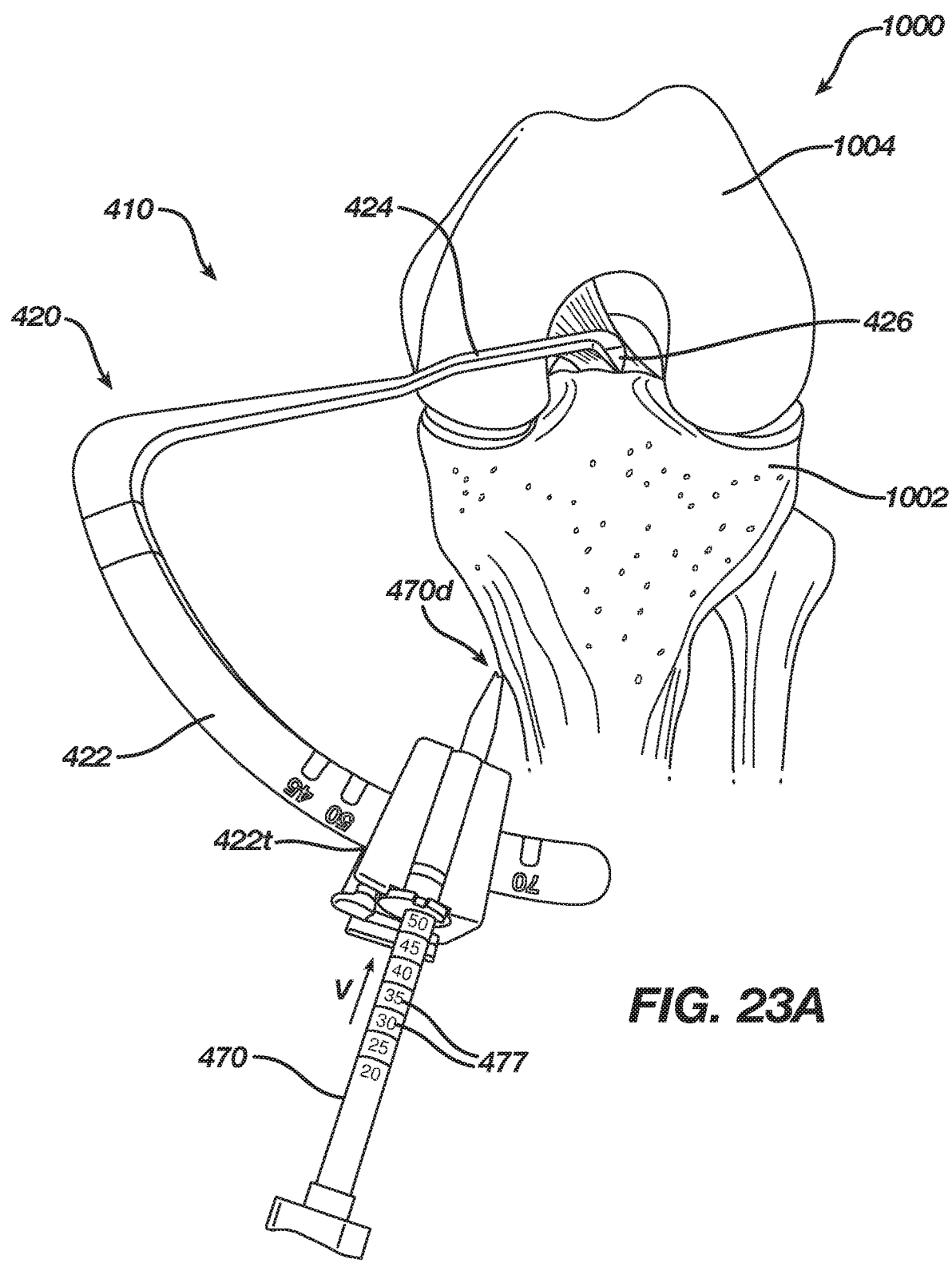
FIG. 23A is a schematic view of one exemplary embodiment of a modular guide and a bullet being used to measure a tibial bone stock of a knee.

As shown in FIG. 23A, a modular guide 410 can be operated to set a desired location of a bone tunnel to be drilled into the tibia 1002 of a knee 1000. A trajectory for the bone tunnel can be set along the first arm 422 using techniques described herein or otherwise known to those skilled in the art, and a distal tip 426 of a second arm 424 of the guide arm 420 can be positioned at a desired location for a distal end of the bone tunnel to be formed in the tibia 1002. The bullet 470 can be set in its locked position, and then can be advanced in a direction V towards the tibia until a distal tip 470d of the bullet engages the bone at a desired location for a proximal end of the bone tunnel to be formed. As the bullet 470 is advanced towards the tibia, the values on the indicia 477 formed on the shaft of the bullet 470 decrease, which is sensible because the values are indicative of a thickness of the bone to be drilled, i.e., the bone stock. The value of the indicia 477 disposed adjacent to a proximate surface 422t of the first arm is representative of the bone stock, as shown the distance between the distal tip 470d and the distal tip 426. As shown in FIGS. 23A and 23B, the measured bone stock is about 45 millimeters.

The measured bone stock can be indicated on the drill pin depth gage 480. As shown in FIG. 23C, an indicator 490 is locked with respect to a shaft 482 such that a proximal face 492p of the indicator 490 is located at the 45 millimeter mark of the indicia 486 formed on the shaft 482 to indicate the maximum drill pin length. More particularly, a rotatable knob 496 of the indicator 490 can be rotated to have an engagement mechanism (not shown) engage the shaft 482 and lock the location of the indicator 490. The knob 496 can likewise be rotated to unlock the indicator 490 and set other locations for the maximum drill pin length. The shaft 482 can be of a construction similar to the shaft 382 of the drill pin depth gage 380. While the indicator 490 has a different locking mechanism associated with it, the indicator 490 can generally operate in a nature similar to the indicator 390 of the drill pin depth gage 380.

During the course of a surgical procedure, the measurement of the bone stock and respective indication of the same on the drill pin depth gage can occur near simultaneously. For example, a surgeon or surgeon's assistant can measure the bone stock, announce the measurement to a second person, whether a surgeon or surgeon's assistant, who can then set the bone stock measurement on the drill pin depth gage. This allows for an expedited and accurate setting of the drill pin maximum length or distance.

Figure 23D:
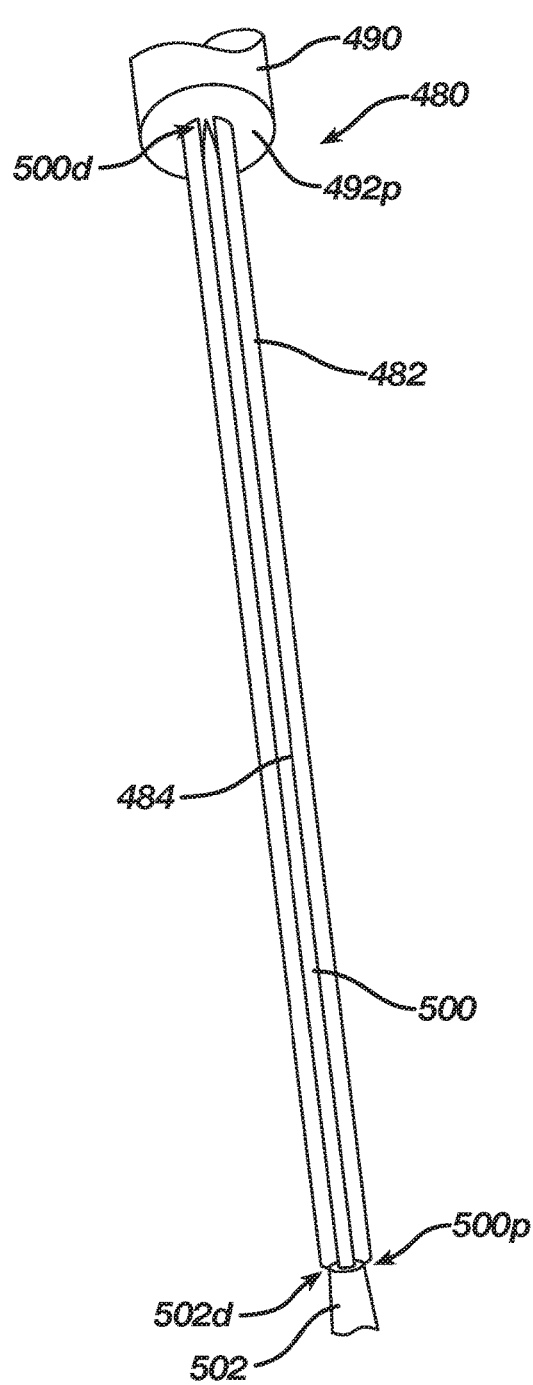
FIG. 23D is a back perspective view of the drill pin depth gage of FIG. 23C having a drill pin disposed therein.
Figure 23E:
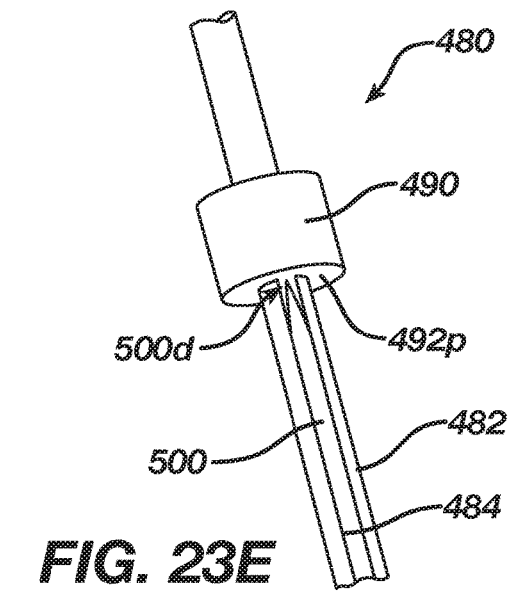
FIG. 23E is a detailed back perspective view of an indicator of the drill pin depth gage and a distal end of the drill pin of FIG. 23D.
Figure 23F:
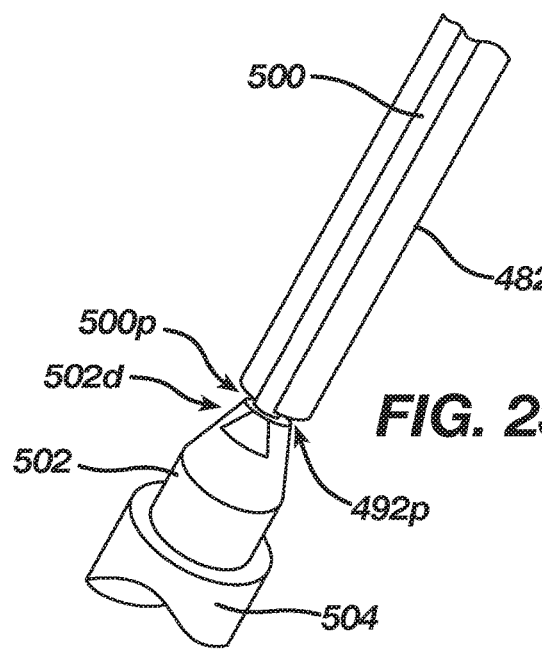
FIG. 23F is a detailed back perspective view of a proximal end of the drill pin depth gage and a proximal end of the drill pin of FIG. 23D.

FIGS. 23D-23F illustrate the insertion of a drill pin 500 into the drill pin depth gage 480. As shown, a drill pin 500 having a proximal end 500p thereof disposed within a drill chuck 502 of a drill 504 can be inserted into an elongate channel or slot 484 of the shaft 482. As shown in FIGS. 23D and 23E, the drill pin 500 can be inserted into the channel 484 and placed such that its distal end 500d engages the proximal face 492p of the indicator 492. As shown in FIGS. 23D and 23F, the chuck 502 holding the proximal end 500p of the drill pin 500 can be brought into contact with a proximal end 482p of the shaft 482. The chuck 502 can be locked to set the location of the drill pin 500 with respect to the chuck 502 once the distal end 500d of the drill pin 500 is engaged with the proximal face 492p and a distal end 502d of the chuck 502 is engaged with the proximal end 482p. Accordingly, the amount of the drill pin 500 that is exposed from the chuck 502 is equal to the length of the bone stock plus the length of the bullet.

Figure 23G:
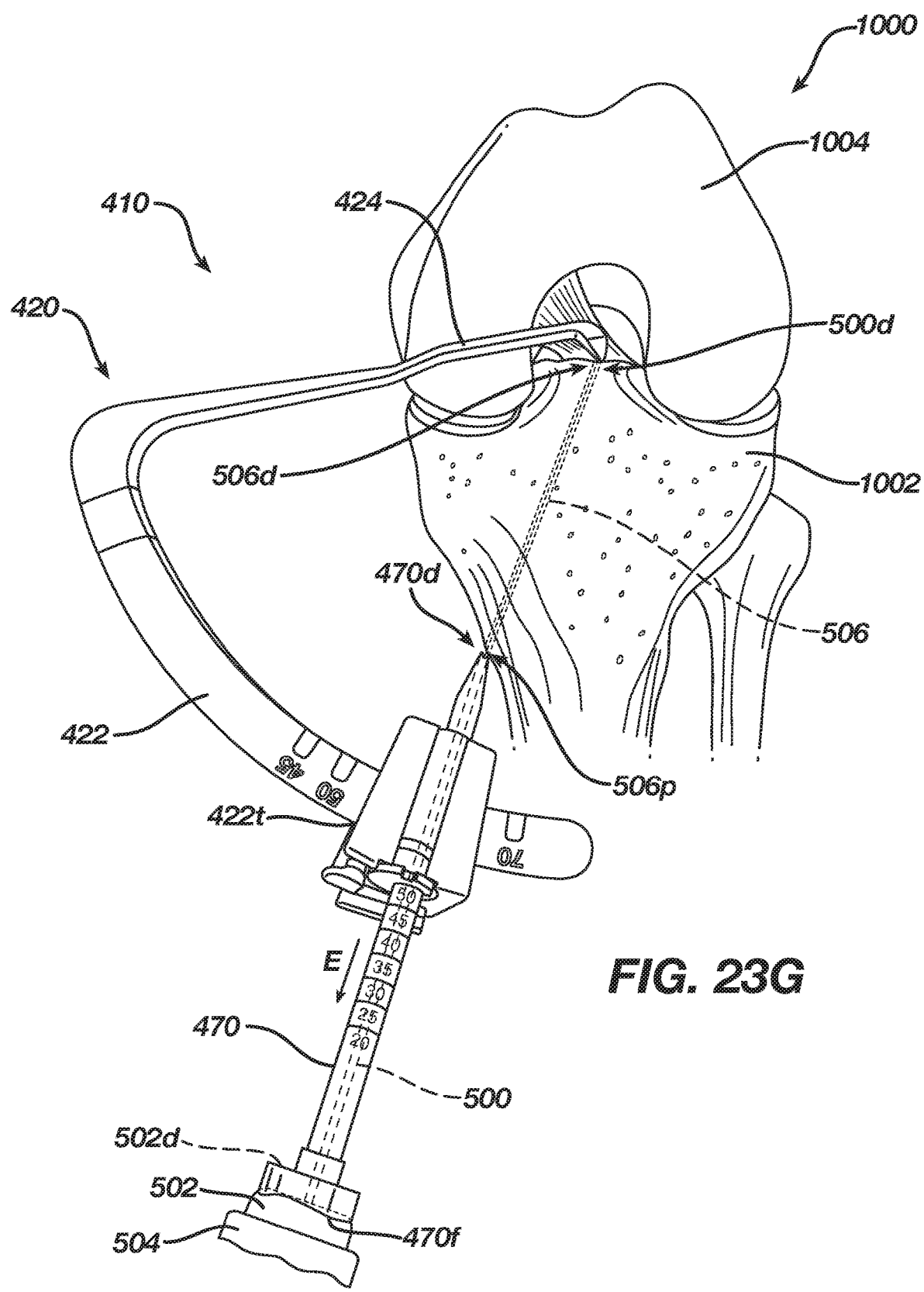
FIG. 23G is a schematic view of the knee of FIG. 23A illustrating a pilot hole drilled by the drill pin of FIG. 23D to start a tibial tunnel using the modular guide and bullet of FIG. 23A.
Figure 23H:
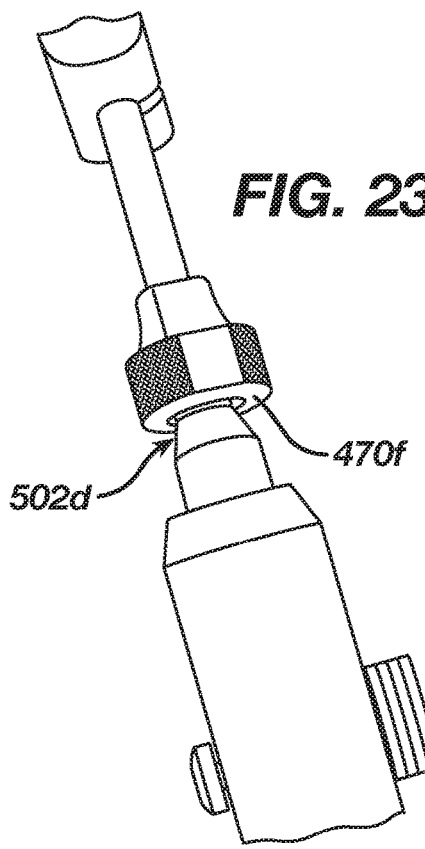
FIG. 23H is a detailed front view of the proximal end of the drill pin of FIG. 23G disposed in the bullet of FIG. 23A, which itself is disposed in the modular guide of FIG. 23A.
Figure 23I:
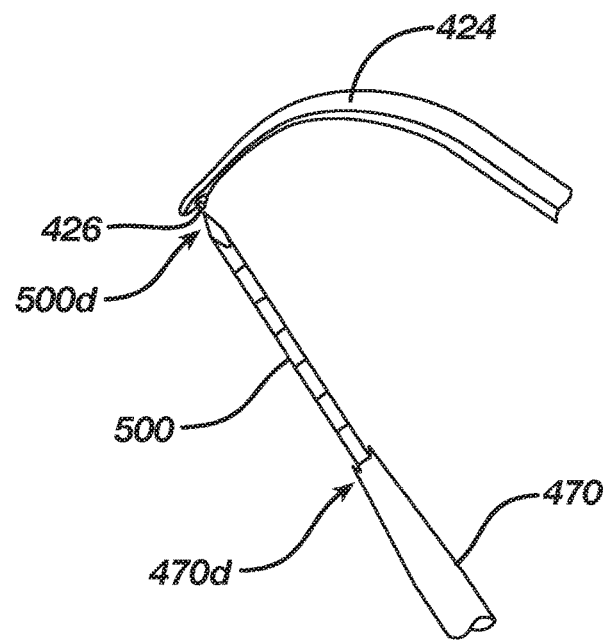
FIG. 23I is a detailed back view of a distal end of the drill pin of FIG. 23G located adjacent to a distal end of a second end of a modular guide of FIG. 23A, with the knee being removed for illustrative purposes.

After locking the drill pin 500 with respect to the chuck 502, the drill 504 can be used to drill the bone tunnel, as illustrated in FIG. 23G. The resulting bone tunnel in the illustrated embodiment is actually a pilot hole configured to be expanded later so it is suitable to receive the desired ligaments therein. The drill pin 500 can be operated and passed from the distal tip 470d of the bullet 470 and into the tibia 1002 to form a proximal end 506p of a bone tunnel 506. The drill pin 500 can then continue along the set trajectory, through the tibia 1002, to the distal tip 426 to form a distal end 506d of the bone tunnel 506. As shown in FIG. 23H, as the distal tip 500d of the drill pin 500 forms the distal end 506d of the bone tunnel 506 and reaches the tip 426, a distal portion of the drill engages the proximal face 470f of the bullet 470, thereby preventing further advancement of the drill pin 500. This results in the configuration illustrated in FIGS. 23G and 23I, in which the distal tip 500d is proximate to the tip 426. In the embodiment illustrated in FIG. 23I, the knee has been removed so the proximity of the distal tip 500d to the tip 426 can be easily viewed. A distance from the distal end 502d of the chuck 502 to the distal tip 500d of the drill pin 500 can be equal to a length between the proximal face 470f of the bullet and the terminal distal travel location.

Upon completion of the formation of the pilot hole, any number of techniques described herein or otherwise known to those skilled in the art can be performed to expand the pilot hole into a tunnel suitable for receiving ligament grafts therein. In one exemplary embodiment, the drill pin 500 is part of a retrograde reamer that has an additional cutting component or reamer 500r (FIG. 23J) disposed proximate to the distal tip 500d that can be deployed outward from the shaft of the drill pin 500 and operated to form a larger bone tunnel. Some non-limiting exemplary embodiments of such drilling devices, and procedures associated with using the same, are provided for in U.S. patent application Ser. No. 14/300,481, entitled "Retro-Cutting Instrument with Adjustable Limit Setting," filed Jun. 10, 2014, the content of which is hereby incorporated by reference in its entirety.

Prior to performing the retrograde cut to expand the diameter of the bone tunnel, it can be advantageous to disassociate the bullet 470 from the modular guide 410. The guide 410 is no longer needed now that the path for forming the initial bore has been defined and the pilot hole subsequently formed. Removing the guide 410 frees up space and hands to perform other tasks during the procedure. While many techniques can be used to disassociate the bullet 470 from the guide 410, including techniques described herein or otherwise known to those skilled in the art, in embodiments in which a side-loading carriage like the carriages 240, 240' are used as part of the modular guide, the bullet 470 can exit through the side of the carriage and the guide arm and carriage can be removed from the surgical site. In the illustrated embodiment, no carriage is provided, and thus the bullet 470 can be disassociated from the guide 410 by pulling the bullet 470 away from the tibia 1002 in a direction E until the distal tip 470d passes the top surface 422t. As described above, such a configuration may not be as preferable as a side-loading carriage because the drill pin 500 must be long enough to allow the bullet 470 to be disposed as described, while maintaining the drill pin 500 in the bullet 470, thereby increasing the possibility of divergence.

Figure 23J:
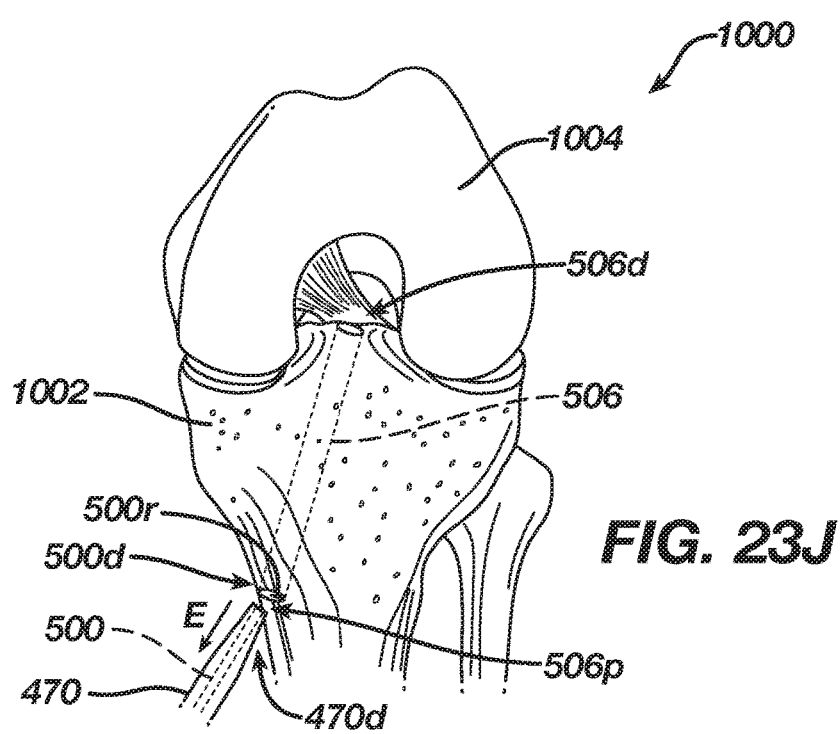
FIG. 23J is a schematic view of the knee of FIG. 23G illustrating an expanded tibial tunnel using a retrograde reamer and the bullet of FIG. 23A.

After the bullet 470 is disassociated from the guide 410, if necessary, the bullet can be returned to a location in which the distal tip 470d engages the tibia 1002. In some instances, the bullet may still be at this location. This positioning allows the bullet 470 to help maintain the trajectory for the drill pin 500 as the reamer 500r is operated and advanced proximally in the direction E from the distal end 506d to the proximal end 506p to expand the diameter of the bore 506, as shown in FIG. 23J. Once the reamer 500r has been operated to expand the bore 506, each of the drill pin 500 and bullet 470 can be removed from the location near the tibia 1002.

Figure 23K:
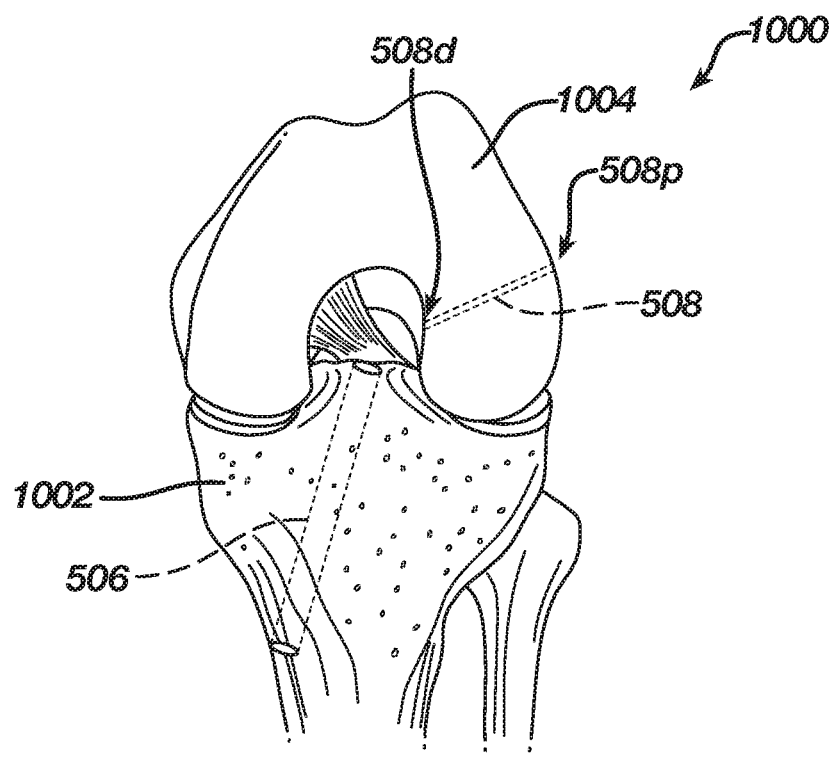
FIG. 23K is a schematic view of the knee of FIG. 23J illustrating a pilot hole drilled by a drill pin to start a femoral tunnel using the modular guide and bullet of FIG. 23A.
Figure 23L:
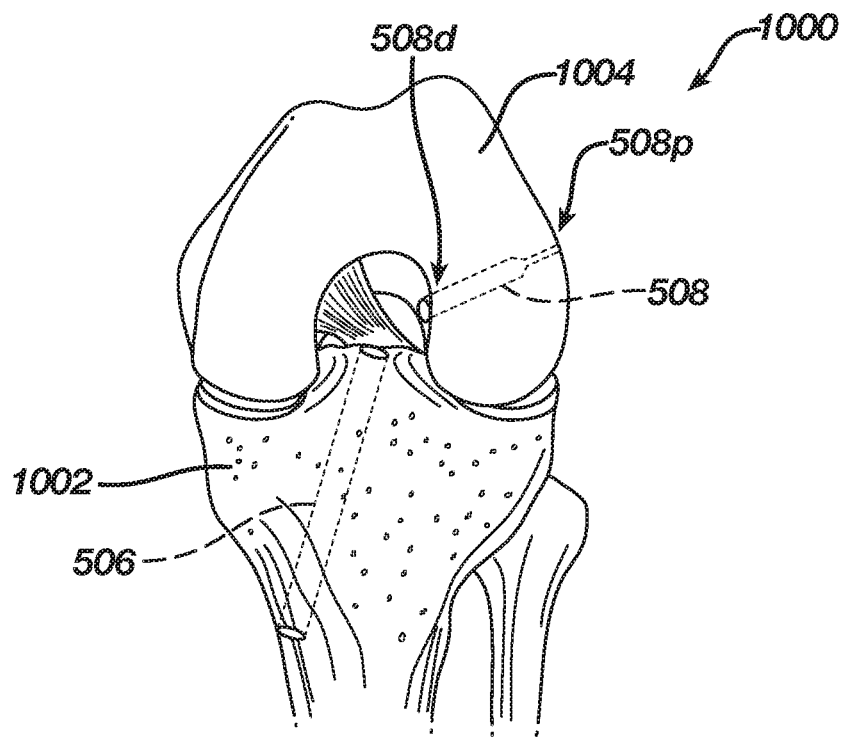
FIG. 23L is a schematic view of the knee of FIG. 23K illustrating an expanded femoral tunnel formed using a retrograde reamer and the bullet of FIG. 23A.

A bone tunnel 508 can likewise be formed in the femur 1004 using a similar technique. The bone tunnel 508 that initially starts as a pilot hole is illustrated in FIG. 23K. Just as with the formation of the bone tunnel 506, a modular guide can be operated to define the path for the tunnel to be formed in the femur 1004. As discussed herein, the modular guide can be similar to that used for the tibia, although typically a different guide arm is used because of the different location and typical desired trajectory associated with the femur.

A bone stock for the femur 1004 can be measured, and a drill pin depth can be set using a drill pin depth gage. A drill pin can the passed through the tibia to first form a proximal end 508p of the bone tunnel 508 and then form a distal end 508d of the bone tunnel 508. The distance traveled by the drill pin can be limited due to the setting of the drill pin depth, thereby preventing unintended contact by the drill pin with tendons and other components located proximate to the distal end 508d. The modular guide can be disassociated from a bullet in which the drill pin is disposed, the bullet returned to a location where it can be used to help guide the drill pin during a retrograde procedure (if it is not already located at the desired location), and then a reamer on the drill pin can be operated expand the size of the bone tunnel, resulting in the tunnel illustrated in FIG. 23L. As shown, the reamer is only operated to expand a portion of the bone tunnel 508, leaving a portion having the smaller diameter. A person having skill in the art will recognize that a variety of other bone tunnel configurations are possible. As discussed herein, when a universal guide system like those described herein is used to form the tunnels 506 and 508, a surgeon performing this procedure can use the same system without having to make separate accommodations, regardless of whether the surgeon is right hand or left handed.

One skilled in the art will appreciate further features and advantages of the invention based on the above-described embodiments. Accordingly, the invention is not to be limited by what has been particularly shown and described, except as indicated by the appended claims. For example, to the extent the disclosures provided for herein describe devices, systems, and methods used in conjunction with ACL and PCL ligament repairs, a person having skill in the art would be able to apply these disclosures to surgical procedures performed with other ligaments, such as the MCL, and with other anatomies and in other locations of the body without departing from the spirit of the present disclosure. All publications and references cited herein are expressly incorporated herein by reference in their entirety.

What is claimed is:

1. A surgical instrument, comprising:
   a guide arm having a first portion configured to define an angle at which a bore is to be drilled into bone and a second portion configured to define a location of a distal end of the bore to be drilled into bone, the distal end of the bore to be drilled into bone corresponding to an exit face of the bore to be drilled into bone, wherein an angle extending between the first portion and the second portion is approximately 110 degrees or less; and
   a carriage disposed on the first portion of the guide arm, the carriage having a length that is greater than a width or a thickness thereof, and the length of the carriage extending substantially transverse to a length of the first portion of the guide arm, and the carriage being configured to translate along a length of the first portion and to be selectively locked at different locations along the length to set the angle at which the bore is to be drilled into bone.

2. The surgical instrument of claim 1, wherein the carriage includes a bullet-receiving opening formed therein that is configured to receive a bullet.

3. The surgical instrument of claim 2, further comprising a bullet configured to be removably coupled to the carriage and, when coupled to the carriage, configured to define a location of a proximal end of the bore to be drilled into bone.

4. The surgical instrument of claim 2,
wherein the first portion of the guide arm includes opposed first and second flat surfaces and first and second sidewalls extending between the first and second flat surfaces, the surface areas of the flat surfaces being substantially larger than the surface areas of the sidewalls,
wherein the carriage includes first and second opposed facial surfaces and first and second side surfaces extending between the first and second facial surfaces, the first and second flat surfaces of the first portion of the guide arm and the first and second facial surfaces of the carriage extending substantially parallel to each other, with the first facial surface of the carriage facing away from the first flat surface of the first portion of the guide arm,
wherein the bullet-receiving opening is formed in the first facial surface of the carriage.

5. The surgical instrument of claim 4, wherein the carriage is configured such that a bullet received by the bullet-receiving opening is held at an angle with respect to the second flat surface such that a distal tip of a drill pin extending through the bullet disposed in the bullet receiving opening is configured to engage a distal end of the second portion of the guide arm that defines the location of the distal end of the bore to be drilled into bone.

6. The surgical instrument of claim 1, wherein the first portion is not movable with respect to the second portion when the first and second portions are coupled together.

7. The surgical instrument of claim 1, wherein the first portion of the guide arm includes a plurality of slots formed therein, each slot being indicative of an intended angle at which the bore is to be drilled into bone.

8. The surgical instrument of claim 7, wherein the carriage includes a passive locking mechanism configured to passively engage a slot of the plurality of slots to set the angle at which the bore is to be drilled into bone.

9. The surgical instrument of claim 8, wherein the passive locking mechanism comprises a selectively deployable key having a configuration that is complementary to the plurality of slots such that when the selectively deployable key is disposed in a slot, the location of the carriage is fixed with respect to the first portion of the guide arm.

10. The surgical instrument of claim 9, wherein the passive locking mechanism further comprises a button configured to disengage the selectively deployable key from a slot of the plurality of slots to allow the carriage to translate along a length of the first portion.

11. The surgical instrument of claim 1, wherein the second portion includes a distal tip disposed at a terminal end thereof, the tip being configured to engage bone at an intended location of the distal end of the bore to be drilled into bone.

12. A surgical guide for use in conjunction with drilling a bore in bone, comprising:
a first arcuate arm having a first end, a second end, and an intermediate portion extending therebetween, the intermediate portion having indicia formed thereon to indicate an intended angle at which a bore is to be drilled into bone;
a second arm having a first end, a second end, and an intermediate portion extending therebetween, the first end of the second arm being directly connected to the second end of the first arm to form a unitary construction of the guide such that the second arm is substantially stationary with respect to the first arm, and an angle extending between the first and second arms is approximately 110 degrees or less; and
a bullet configured to be removably associated with the first arcuate arm such that a location of the bullet with respect to the indicia reflects an intended angle at which a distal tip of the bullet is to form with the bone in which the bore is to be drilled, and in turn defining the intended angle of the bore to be drilled into the bone,
wherein the first arm and the second arm are not moved with respect to one another to adjust the intended angle of the bore to be drilled into the bone.

13. The guide of claim 12, wherein the indicia further comprise a plurality of engagement features formed in a surface of the first arcuate arm.

14. The guide of claim 12, wherein the second end of the second arm includes a distal tip configured to engage bone at an intended location of a distal end of the bore to be drilled into the bone.

15. The guide of claim 12, wherein the first arm includes opposed first and second flat surfaces and first and second sidewalls extending between the first and second flat surfaces, the surface areas of the flat surfaces being substantially larger than the surface areas of the sidewalls.

16. The guide of claim 12, further comprising a carriage configured to receive the bullet, translate along a length of the first arm, and be selectively locked with respect to the indicia to set the intended angle at which the distal tip of the bullet is intended to form with the bone in which the bore is being drilled.

17. The guide of claim 16, wherein the carriage includes first and second opposed facial surfaces and first and second side surfaces extending between the first and second facial surfaces, the first facial surface of the carriage facing away from the first arcuate arm.

18. The guide of claim 17, wherein the carriage is configured such that the bullet received by the carriage is held at an angle with respect to the first arcuate arm such that a distal tip of a drill pin extending through the bullet is configured to engage a distal tip of the second arm.

19. The guide of claim 16,
wherein the indicia further comprise a plurality of slots formed in a surface of the first arcuate arm, and
wherein the carriage includes a passive locking mechanism configured to passively engage a slot of the plurality of slots to set the intended angle of the bore to be drilled into the bone.

20. A surgical instrument, comprising:
a guide arm having a first portion configured to define an angle at which a bore is to be drilled into bone and a second portion having a distal tip disposed at a terminal end thereof, the distal tip configured to be positioned at a location of a distal end of the bore to be drilled into bone, wherein an angle extending between the first portion and the second portion is approximately 110 degrees or less; and
a carriage disposed on the first portion of the guide arm, the carriage having a length that is greater than a width or a thickness thereof, and the length of the carriage extending substantially transverse to a length of the first portion of the guide arm, and the carriage being configured to translate along a length of the first portion and to be selectively locked at different locations along the length to set the angle at which the bore is to be drilled into bone.

21. The surgical instrument of claim 20, wherein the carriage includes a bullet-receiving opening formed therein that is configured to receive a bullet.

22. The surgical instrument of claim 21, further comprising a bullet configured to be removably coupled to the carriage and, when coupled to the carriage, configured to define a location of a proximal end of the bore to be drilled into bone.

23. The surgical instrument of claim 22,
wherein the first portion of the guide arm includes opposed first and second flat surfaces and first and second sidewalls extending between the first and second flat surfaces, the surface areas of the flat surfaces being substantially larger than the surface areas of the sidewalls,
wherein the carriage includes first and second opposed facial surfaces and first and second side surfaces extending between the first and second facial surfaces, the first and second flat surfaces of the first portion of the guide arm and the first and second facial surfaces of the carriage extending substantially parallel to each other, with the first facial surface of the carriage facing away from the first flat surface of the first portion of the guide arm,
wherein the bullet-receiving opening is formed in the first facial surface of the carriage.

24. The surgical instrument of claim 23, wherein the carriage is configured such that the bullet received by the bullet-receiving opening is held at an angle with respect to the second flat surface such that a distal tip of a drill pin extending through a bullet disposed in the bullet receiving opening is configured to engage the distal end of the second portion of the guide arm that defines the location of the distal end of the bore to be drilled into bone.

25. The surgical instrument of claim 20, wherein the first portion of the guide arm includes a plurality of slots formed therein, each slot being indicative of an intended angle at which the bore is to be drilled into bone.

26. A surgical guide for use in conjunction with drilling a bore in bone, comprising:
a first arcuate arm having a first end, a second end, and an intermediate portion extending therebetween, the intermediate portion having indicia formed thereon to indicate an intended angle at which a bore is to be drilled into bone;
a second arm having a first terminal end, a second end, and an intermediate portion extending therebetween, the first terminal end of the second arm being directly connected to the second end of the first arm to form a unitary construction of the guide such that the second arm is substantially stationary with respect to the first arm, and an angle extending between the first and second arms is approximately 110 degrees or less; and
a bullet configured to be removably associated with the first arcuate arm such that a location of the bullet with respect to the indicia reflects an intended angle at which a distal tip of the bullet is to form with the bone in which the bore is to be drilled, and in turn defining the intended angle of the bore to be drilled into the bone.

27. The guide of claim 26, wherein the indicia further comprise a plurality of engagement features formed in a surface of the first arcuate arm.

28. The guide of claim 26, wherein the second end of the second arm includes a distal tip configured to engage bone at an intended location of a distal end of the bore to be drilled into the bone.

29. The guide of claim 26, wherein the first arm includes opposed first and second flat surfaces and first and second sidewalls extending between the first and second flat surfaces, the surface areas of the flat surfaces being substantially larger than the surface areas of the sidewalls.

30. The guide of claim 26, further comprising a carriage configured to receive the bullet, translate along a length of the first arm, and be selectively locked with respect to the indicia to set the intended angle at which the distal tip of the bullet is intended to form with the bone in which the bore is being drilled.

\* \* \* \* \*